United States Patent
Uto et al.

(10) Patent No.: US 9,670,173 B2
(45) Date of Patent: *Jun. 6, 2017

(54) DICARBOXYLIC ACID COMPOUND

(71) Applicant: DAIICHI SANKYO COMPANY, LIMITED, Tokyo (JP)

(72) Inventors: Yoshikazu Uto, Tokyo (JP); Mikio Kato, Tokyo (JP); Hidenori Takahashi, Tokyo (JP); Yasuyuki Ogawa, Tokyo (JP); Osamu Iwamoto, Tokyo (JP); Hiroko Kono, Tokyo (JP); Kazumasa Aoki, Tokyo (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/282,384

(22) Filed: Sep. 30, 2016

(65) Prior Publication Data

US 2017/0015641 A1 Jan. 19, 2017

Related U.S. Application Data

(63) Continuation of application No. 14/784,187, filed as application No. PCT/JP2014/061390 on Apr. 23, 2014.

(30) Foreign Application Priority Data

Apr. 24, 2013 (JP) ................. 2013-091090

(51) Int. Cl.
| | | |
|---|---|---|
| A61K 31/196 | (2006.01) | |
| C07D 213/75 | (2006.01) | |
| C07D 295/155 | (2006.01) | |
| C07D 213/82 | (2006.01) | |
| C07C 311/20 | (2006.01) | |
| C07D 295/14 | (2006.01) | |

(52) U.S. Cl.
CPC ........ *C07D 295/155* (2013.01); *C07C 311/20* (2013.01); *C07D 213/75* (2013.01); *C07D 213/82* (2013.01); *C07D 295/14* (2013.01); *C07C 2101/02* (2013.01); *C07C 2101/14* (2013.01)

(58) Field of Classification Search
CPC  C07D 295/155; C07D 295/14; C07D 213/82; C07D 213/75; C07C 2101/02; C07C 2101/14; C07C 311/20
USPC ....................................................... 546/184
See application file for complete search history.

(56) References Cited

U.S. PATENT DOCUMENTS

| 5,071,841 A | 12/1991 | Sohda et al. |
| 2006/0217426 A1 | 9/2006 | Eto et al. |
| 2011/0130445 A1 | 6/2011 | Lampe et al. |
| 2013/0029973 A1 | 1/2013 | Hachiya et al. |
| 2013/0053369 A1 | 2/2013 | Hachiya et al. |
| 2013/0336920 A1 | 12/2013 | Lewis et al. |
| 2014/0023611 A1 | 1/2014 | Lewis et al. |
| 2015/0031727 A1 | 1/2015 | Miura et al. |

FOREIGN PATENT DOCUMENTS

| CN | 1045106 A | 9/1990 |
| CN | 1210856 A | 3/1999 |
| CN | 102712577 A | 10/2012 |
| CN | 102869656 A | 1/2013 |
| EP | 0 376 197 A1 | 7/1990 |
| EP | 0 899 262 A2 | 3/1999 |
| JP | 2013-509369 A | 3/2013 |
| WO | WO-2009/157418 A1 | 12/2009 |
| WO | WO-2011/051165 A1 | 5/2011 |
| WO | WO-2011/136269 A1 | 11/2011 |
| WO | WO-2012/006475 A1 | 1/2012 |
| WO | WO-2013/082751 A1 | 6/2013 |
| WO | WO-2013/082756 A1 | 6/2013 |
| WO | WO-2014/003153 A1 | 1/2014 |
| WO | WO2014175317 | * 10/2014 |
| WO | WO-2016/047613 A1 | 3/2016 |

OTHER PUBLICATIONS

Columbian Office Action issued in application No. 15.251845 mailed Dec. 2, 2015.
F. Malberti, "Hyperphosphataemia: Treatment Options," Drugs 73:673-688 (2013).
F. Verbeke et al., "Prognostic Value of Aortic Stiffness and Calcification for Cardiovascular Events and Mortality in Dialysis Patients: Outcome of the Calcification Outcome in Renal Disease (CORD)Study," Clinical Journal of the American Society of Nephrology vol. 6, Jan. 2011 153-159.
First Office Action issued in Chinese Patent Application No. 201480022830.2 mailed May 10, 2016.
H. Murer, et al. "The Sodium Phosphate Cotransporter Family SLC34," Pflugers Arch-Eur J Physiol (2004) 447: 763-767.
International Search Report issued in corresponding application No. PCT/JP2014/061390 mailed Jul. 15, 2014.
M.R. Wills et al., "Aluminum Poisoning: Dialysis Encephalopathy, Osteomalacia, and Anaemia," The Lancet, Jul. 2, 1983, 29-34.
N. Eto et al., "Nicotinamide prevents the development of hyperphosphataemia by suppressing intestinal sodium-dependent phosphate transporter in rats with adenine-induced renal failure," Nephrol Dial Transplant 20:1378-1384 (2005).
S. C. Schiavi et al., "Npt2b Deletion Attenuates Hyperphosphatemia Associated with CKD," J Am Soc Nephrol 23: 1691-1700, 2012.
T. Kakuta et al., "Effect of Sevelamer and Calcium-Based Phosphate Binders on Coronary Artery Calcification and Accumulation of Circulating Advanced Glycation End Products in Hemodialysis Patients," Am J Kidney Dis. 2011; 57(3): 422-431.
T. Maruyama et al., "To Facilitate the Compliance of Phosphate Binder for the Control of Hyperphosphatemia in Chronic Kidney Disease Patients," Clinical Calcium vol. 19, No. 2, 2009, 100 (248).
Y. Sabbagh et al., "Intestinal Npt2b Plays a Major Role in Phosphate Absorption and Homeostasis," J Am Soc Nephrol 20:2348-2358 (2009).

* cited by examiner

*Primary Examiner* — Noble Jarrell
*Assistant Examiner* — Daniel Carcanague
(74) *Attorney, Agent, or Firm* — Foley & Lardner LLP

(57) ABSTRACT

It is an object of the present invention to provide a medicament for preventing or treating hyperphosphatemia. Solution: A compound represented by a general formula (I) or a pharmacologically acceptable salt thereof. (In the formula, $R^1$: a methyl group or the like, $R^2$: a hydrogen atom or the like, $R^3$: a hydrogen atom or the like, A: a cyclohexyl ring or the like, X: CH or the like, Y: CH or the like, Z: CH or the like, and n: 2 or the like).

10 Claims, No Drawings

DICARBOXYLIC ACID COMPOUND

CROSS-REFERENCE TO RELATED APPLICATIONS

The present application is a continuation of U.S. patent application Ser. No. 14/784,187, filed on Oct. 13, 2015, which is a U.S. national stage application of International Patent Application No. PCT/JP2014/061390, filed on Apr. 23, 2014, which claims the benefit of priority to Japanese Patent Application No. 2013-091090, filed Apr. 24, 2013, the entireties of which are hereby incorporated by reference.

TECHNICAL FIELD

The present invention relates to a compound that is useful for preventing or treating hyperphosphatemia or disease associated with hyperphosphatemia, or a pharmacologically acceptable salt thereof.

BACKGROUND ART

Phosphorus is present in a living body in various forms as constitutional elements important for the body, such as DNA, RNA or bone, and plays an important role in life-sustaining activities.

Phosphoric acid is mainly absorbed from food through the digestive tract in the form of inorganic phosphorus, and it is then eliminated through the kidney in the form of urine (Non Patent Literature 1).

Absorption of phosphorus through the digestive tract, elimination thereof through the kidney, and absorption and/or metabolism thereof from the bone are controlled by the action of vitamin D, parathyroid hormone (PTH), etc., and thus, the blood level of phosphorus is maintained constant.

In the case of renal failure, hyperphosphatemia in which the blood level of phosphorus shows an extremely high value is developed in many cases due to a reduction in elimination of phosphoric acid from the kidney. An excessive amount of phosphoric acid binds to blood calcium, and it causes ectopic calcification in the cardiovascular system, so that it seems to become a risk factor for cardiovascular diseases such as myocardial infarction (Non Patent Literature 2).

Moreover, hyperphosphatemia secondarily causes hypocalcemia, and in compensation, hyperparathyroidism characterized by an increase in the blood PTH level is developed. This also becomes a main factor for developing renal osteodystrophy. As mentioned above, hyperphosphatemia in chronic renal failure patients reduces the QOL of the patients due to bone fracture, bone pain, etc., and at the same time, it becomes a main factor for the death of chronic renal failure patients.

At present, as a therapeutic drug for hyperphosphatemia, there is used a phosphate adsorbent that adsorbs phosphoric acid in the digestive tract and thereby suppresses the absorption thereof, as well as diet restriction. As oral adsorbents, various medicaments such as calcium preparations (precipitated calcium carbonate, etc.), polymer preparations (sevelamer hydrochloride), and metallic salt preparations (aluminum hydroxide and lanthanum carbonate) have been used. It is pointed out that individual preparations have problems.

Regarding the calcium preparations, it has been demonstrated that vascular calcification is promoted due to hypercalcemia (Non Patent Literature 3), and the polymer preparations are problematic in terms of drug compliance caused by administration at a dose of several grams per day and digestive symptoms such as constipation and/or diarrhea (Non Patent Literature 4).

Moreover, regarding the metallic salt preparations, the risk of being accumulated in the body is pointed out (Non Patent Literature 5). Thus, sufficient therapeutic drugs for hyperphosphatemia have not yet been developed.

It has been reported that a sodium-dependent phosphate transporter expressed in small intestinal epithelial cells plays an important role in absorption of inorganic phosphate through the digestive tract (Non Patent Literature 6). It is anticipated that a compound that specifically inhibits the active transport of phosphate can suppress absorption of phosphorus through the digestive tract, more efficiently than oral adsorbents, and that it can improve the drug compliance that has been the problem of oral adsorbents and can solve the problems such as digestive symptoms and accumulation.

Under the aforementioned circumstances, it has been desired to develop a novel preparation for preventing or treating hyperphosphatemia or disease associated with hyperphosphatemia.

The compound described in WO2011/136269 is relevant to the compound of the present invention. However, this compound differs from the compound of the present invention in terms of essential partial structure.

CITATION LIST

Patent Literature

Patent Literature 1: WO2011/136269

Non Patent Literature

Non Patent Literature 1: H. Murer et al., Pflugers Arch—Eur J Physiol (2004) 447: 763-767

Non Patent Literature 2: F. Verbeke et al., Clinical Journal of the American Society of Nephrology 6, 153 (2011)

Non Patent Literature 3: T. Kakuta et al., Am J Kidney Dis. 57(3): 422 (2011)

Non Patent Literature 4: T. Maruyama et al., CLINICAL CALCIUM 19, 2, 100(248), (2009)

Non Patent Literature 5: M. R. Wills, J. Savory J. Lancet 2, 29 (1983)

Non Patent Literature 6: S. C. Schiavi et al., J Am Soc Nephrol 23: 1691, 2012

SUMMARY OF INVENTION

Technical Problem

It is an object of the present invention to provide a compound that is useful as an active ingredient for preventing and treating hyperphosphatemia, or a pharmacologically acceptable salt thereof.

Solution to Problem

The present inventors have conducted intensive studies directed towards developing a compound that is useful as an active ingredient for preventing and treating hyperphosphatemia. As a result, the inventors have completed the present invention. Specifically, the present invention is as described below.

[1]

A compound represented by a general formula (I) or a pharmacologically acceptable salt thereof:

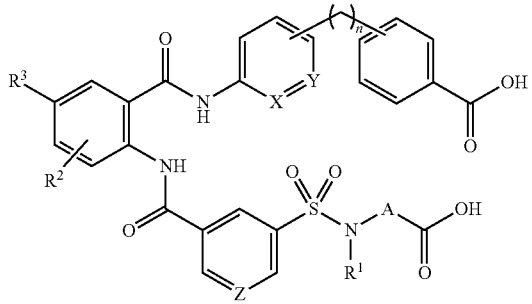

wherein each substituent is as defined below:

$R^1$: a C1-6 alkyl group, a C1-6 alkoxy C1-6 alkyl group, a C3-6 cycloalkyl group, or a C3-6 cycloalkyl C1-6 alkyl group, $R^2$: a hydrogen atom or a halogen group, $R^3$: a hydrogen atom, a halogen group, a halogeno C1-6 alkyl group, a halogeno C1-6 alkoxy group, a saturated cyclic amino group, a dialkylamino group, a C3-6 cycloalkyl C1-6 alkoxy group, or an alkoxy group, A: a C3-6 cycloalkyl ring, X: CH or N, Y: CH or N, Z: CH or N, and n: an integer selected from 1, 2, 3, and 4.

[2]

The compound according to [1] above or a pharmacologically acceptable salt thereof, wherein the compound represented by the general formula (I) is a compound represented by a general formula (I'):

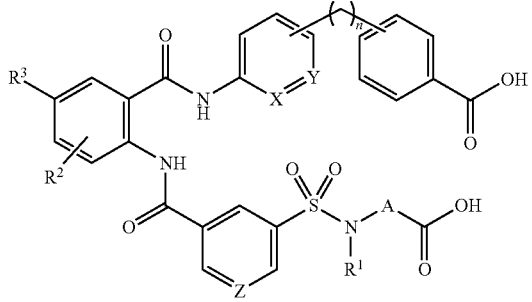

[3]

The compound according to [1] or [2] above, or a pharmacologically acceptable salt thereof, wherein $R^1$ represents a methyl group, an ethyl group, a methoxyethyl group, a cyclopropyl group, or a cyclopropylmethyl group.

[4]

The compound according to any one selected from [1] to [3] above, or a pharmacologically acceptable salt thereof, wherein $R^2$ represents a hydrogen atom, a chlorine atom, or a bromine atom.

[5]

The compound according to any one selected from [1] to [4] above, or a pharmacologically acceptable salt thereof, wherein $R^3$ represents a hydrogen atom, a fluorine atom, a chlorine atom, a bromine atom, a trifluoromethyl group, a 2,2,2-trifluoroethoxy group, a pyrrolidin-1-yl group, a piperidin-1-yl group, a diethylamino group, a cyclopropylmethoxy group, or a methoxy group.

[6]

The compound according to any one selected from [1] to [5] above, or a pharmacologically acceptable salt thereof, wherein A represents a cyclohexane ring.

[7]

The compound according to any one selected from [1] to [6] above, or a pharmacologically acceptable salt thereof, wherein X, Y, and Z each represent CH.

[8]

The compound according to any one selected from [1] to [7] above, or a pharmacologically acceptable salt thereof, wherein n is 2.

[9]

The compound according to [1] or [2] above, or a pharmacologically acceptable salt thereof, wherein each substituent is any one selected from the following substituent group:

$R^1$: a methyl group, an ethyl group, a methoxyethyl group, a cyclopropyl group, and a cyclopropylmethyl group, $R^2$: a hydrogen atom, a chlorine atom, and a bromine atom, $R^3$: a hydrogen atom, a fluorine atom, a chlorine atom, a bromine atom, a trifluoromethyl group, a 2,2,2-trifluoroethoxy group, a pyrrolidin-1-yl group, a piperidin-1-yl group, a diethylamino group, a cyclopropylmethoxy group, and a methoxy group, A: a cyclohexane ring, X: CH and N, Y: CH and N, Z: CH and N, and n: 2 and 3.

[10]

Any one compound selected from the following compound group or a pharmacologically acceptable salt thereof:

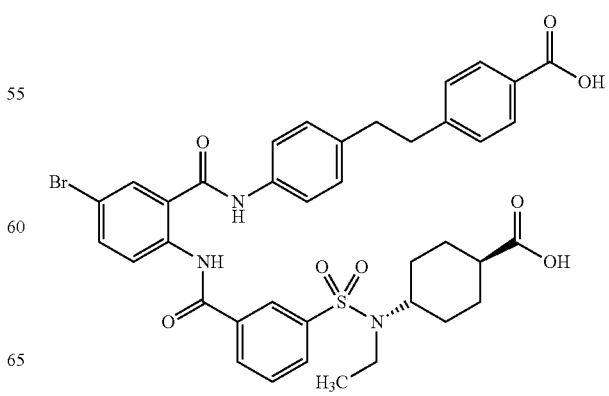

-continued
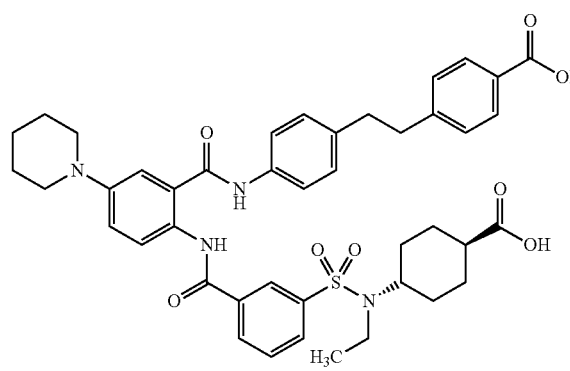
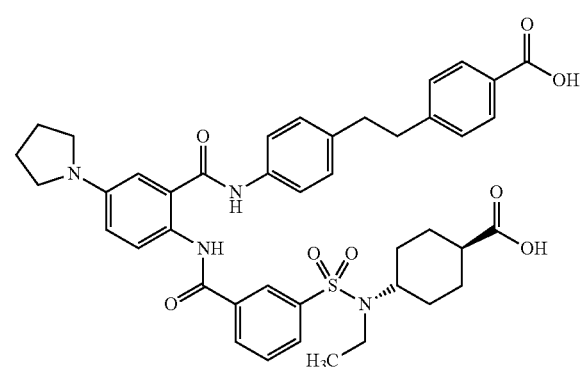
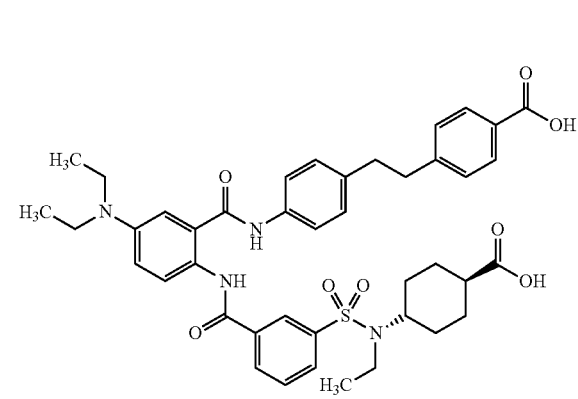
-continued
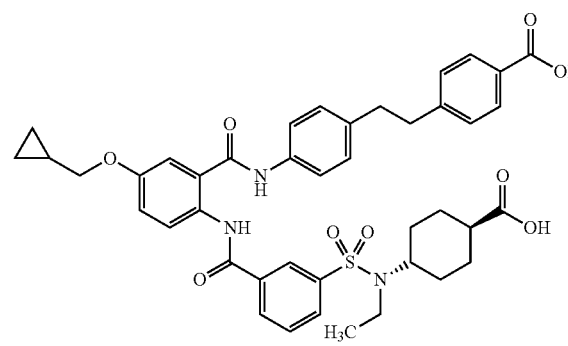
[11]
A compound represented by the following formula or a pharmacologically acceptable salt thereof:
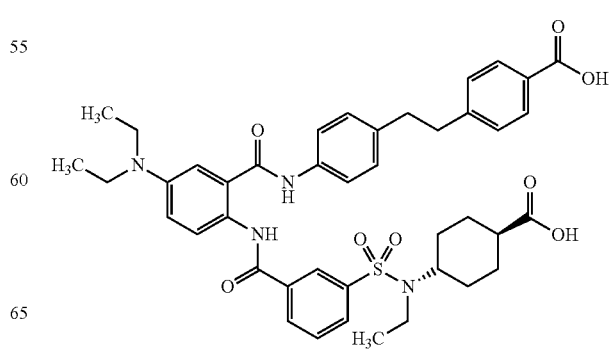
[12]
A compound represented by the following formula or a pharmacologically acceptable salt thereof:

[13]

A compound represented by the following formula or a pharmacologically acceptable salt thereof:

[Structural formula]

[14]

A compound represented by the following formula or a pharmacologically acceptable salt thereof:

[Structural formula]

[15]

The pharmacologically acceptable salt according to any one selected from [10] to [14] above, which is a dipotassium salt.

[16]

The pharmacologically acceptable salt according to any one selected from [10] to [14] above, which is a disodium salt.

[17]

The pharmacologically acceptable salt according to [15] or [16] above, which is a hydrate thereof.

[18]

A pharmaceutical composition comprising the compound according to any one selected from [1] to [17] above, or a pharmacologically acceptable salt thereof.

[19]

The pharmaceutical composition according to [18] above, which is used to inhibit the uptake of phosphorus.

[20]

The pharmaceutical composition according to [18] above, which is used to prevent or treat hyperphosphatemia.

[21]

Use of the compound according to any one selected from [1] to [17] above or a pharmacologically acceptable salt thereof for the production of a pharmaceutical composition for preventing or treating hyperphosphatemia.

[22]

Use of the compound according to any one selected from [1] to [17] above or a pharmacologically acceptable salt thereof for the prevention or treatment of hyperphosphatemia.

[23]

A method for preventing or treating hyperphosphatemia, which comprises administration of an effective amount of the compound according to any one selected from [1] to [17] above or a pharmacologically acceptable salt thereof.

Advantageous Effects of Invention

The compound represented by the general formula (I) of the present invention or a pharmacologically acceptable salt thereof can be used as a preventive and/or therapeutic agent for hyperphosphatemia and the like.

DESCRIPTION OF EMBODIMENTS

Hereinafter, the present invention will be described in detail.

The terms such as substituents used in the present description have the following meanings.

Halogen Group:

The halogen group is a fluorine atom, a chlorine atom, or a bromine atom.

C1-6 Alkyl Group:

The C1-6 alkyl group is a linear or branched alkyl group containing 1 to 6 carbon atoms, and preferred examples include
a methyl group, an ethyl group, a propyl group, and an isopropyl group.

Halogeno C1-6 Alkyl Group:

The halogeno C1-6 alkyl group is a linear or branched alkyl group containing 1 to 6 carbon atoms that is substituted with a halogen group, and preferred examples include a trifluoromethyl group, a difluoromethyl group, a 1,1-difluoroethyl group, a 2,2-difluoroethyl group, and a 2,2,2-trifluoroethyl group.

Halogeno C1-6 Alkoxy Group:

The halogeno C1-6 alkoxy group is a linear or branched alkoxy group containing 1 to 6 carbon atoms that is substituted with a halogen group, and preferred examples include a trifluoromethyl group, a difluoromethyl group, a 1,1-difluoroethyl group, a 2,2-difluoroethyl group, and a 2,2,2-trifluoroethyl group.

C1-6 Alkoxy Group:

The C1-6 alkoxy group is a C1-6 alkyl group to which an oxygen atom is bound, and preferred examples include a methoxy group, an ethoxy group, a propoxy group, and an isopropoxy group.

C2-5 Saturated Cyclic Amino Group:

The C2-5 saturated cyclic amino group is a 3-6 membered cyclic saturated group having a nitrogen atom as an atom constituting the ring, and preferred examples include an azetidine group, a pyrrolidine group, a piperidine group, a morpholine group, and a piperazine group.

C1-6 Alkoxy C1-6 Alkyl Group:

The C1-6 alkoxy C1-6 alkyl group is a C1-6 alkyl group substituted with a C1-6 alkoxy group, and preferred examples include a methoxymethyl group, a methoxyethyl group, a methoxypropyl group, an ethoxymethyl group, and an ethoxyethyl group.

C3-6 Cycloalkyl Group:

The C3-6 cycloalkyl group is a 3-6 membered cyclic alkyl group, and preferred examples include a cyclopropyl group, a cyclobutyl group, a cyclopentyl group, and a cyclohexyl group.

C3-6 Cycloalkyl Ring:

The C3-6 cycloalkyl ring is a 3-6 membered cyclic alkyl ring. Preferred examples include a cyclopropyl ring, a cyclobutyl ring, a cyclopentyl ring, and a cyclohexyl ring. More preferred examples include a cyclobutyl ring having a bond in the 1,3 position, a cyclopentyl ring having a bond in the 1,3 position, and a cyclohexyl ring having a bond in the 1,4 position.

C3-6 Cycloalkyl C1-6 Alkyl Group:

The C3-6 cycloalkyl C1-6 alkyl group is a C3-6 cycloalkyl group to which a C1-6 alkyl group is bound, and preferred examples include a cyclopropylmethyl group, a cyclobutylmethyl group, a cyclopentylmethyl group, a cyclohexylmethyl group, a cyclopropylethyl group, a cyclobutylethyl group, a cyclopentylethyl group, and a cyclohexylethyl group.

C3-6 Cycloalkyl C1-6 Alkoxy Group:

The C3-6 cycloalkyl C1-6 alkoxy group is a C3-6 cycloalkyl group to which a C1-6 alkoxy group is bound, and preferred examples include a cyclopropylmethoxy group, a cyclobutylmethoxy group, a cyclopentylmethoxy group, a cyclohexylmethoxy group, a cyclopropylethoxy group, a cyclobutylethoxy group, a cyclopentylethoxy group, and a cyclohexylethoxy group.

C1-6 Dialkylamino Group:

The C1-6 dialkylamino group is an amino group substituted with two C1-6 alkyl groups, and preferred examples include a dimethylamino group, a methylethylamino group, a diethylamino group, an ethylpropylamino group, and a dipropylamino group.

Preferred examples of the compound represented by the general formula (I) include the compounds described in Examples, and more preferred examples include the following compounds:

4-[2-(4-{[5-bromo-2-({3-[(trans-4-carboxycyclohexyl)(ethyl)sulfamoyl]benzoyl}amino)benzoyl]amino}phenyl)ethyl]benzoic acid, 4-[2-(4-{[2-({3-[(trans-4-carboxycyclohexyl)(ethyl)sulfamoyl]benzoyl}amino)-5-(pyrrolidin-1-yl)benzoyl]amino}phenyl)ethyl]benzoic acid, 4-[2-(4-{[2-({3-[(trans-4-carboxycyclohexyl)(ethyl)sulfamoyl]benzoyl}amino)-5-(piperidin-1-yl)benzoyl]amino}phenyl)ethyl]benzoic acid, 4-[2-(4-{[2-({3-[(trans-4-carboxycyclohexyl)(ethyl)sulfamoyl]benzoyl}amino)-5-(diethylamino)benzoyl]amino}phenyl)ethyl]benzoic acid, 4-[2-(4-{[2-({3-[(cis-4-carboxycyclohexyl)(ethyl)sulfamoyl]benzoyl}amino)-5-(piperidin-1-yl)benzoyl]amino}phenyl)ethyl]benzoic acid, 4-[2-(4-{[2-({3-[(trans-4-carboxycyclohexyl)(ethyl)sulfamoyl]benzoyl}amino)-5-(cyclopropylmethoxy)benzoyl]amino}phenyl)ethyl]benzoic acid, and 4-[2-(4-{[2-({3-[(trans-4-carboxycyclohexyl)(cyclopropyl)sulfamoyl]benzoyl}amino)-5-(piperidin-1-yl)benzoyl]amino}phenyl)ethyl]benzoic acid.

The structural formulae of these compounds are the following.

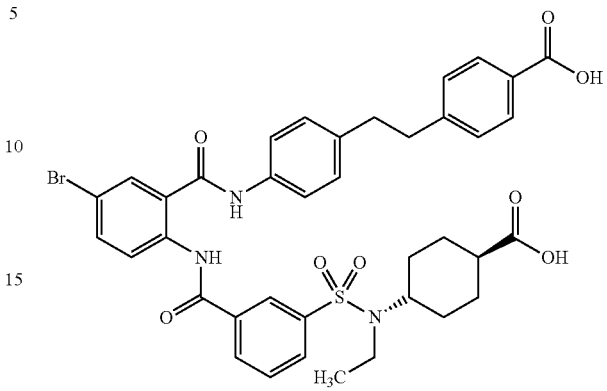

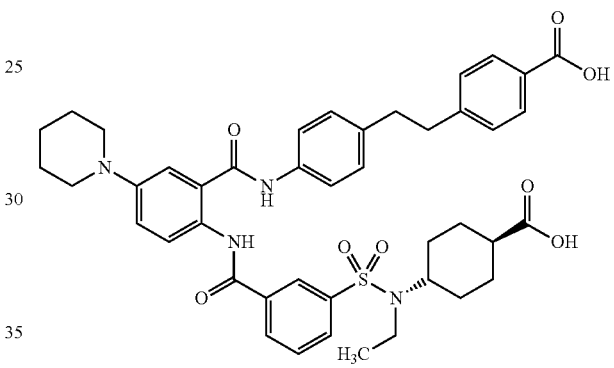

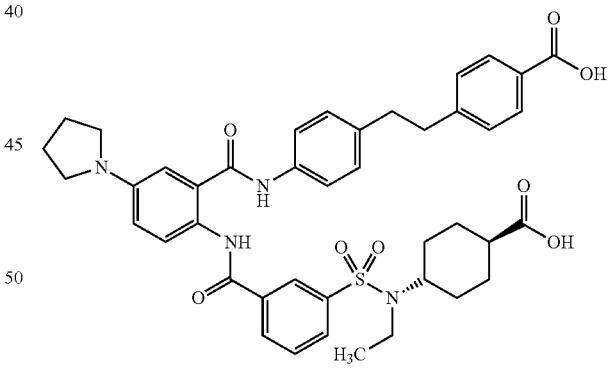

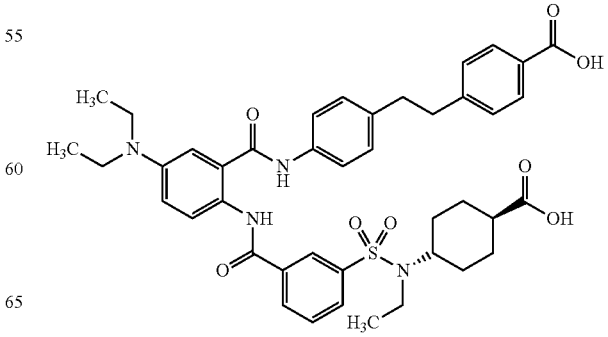

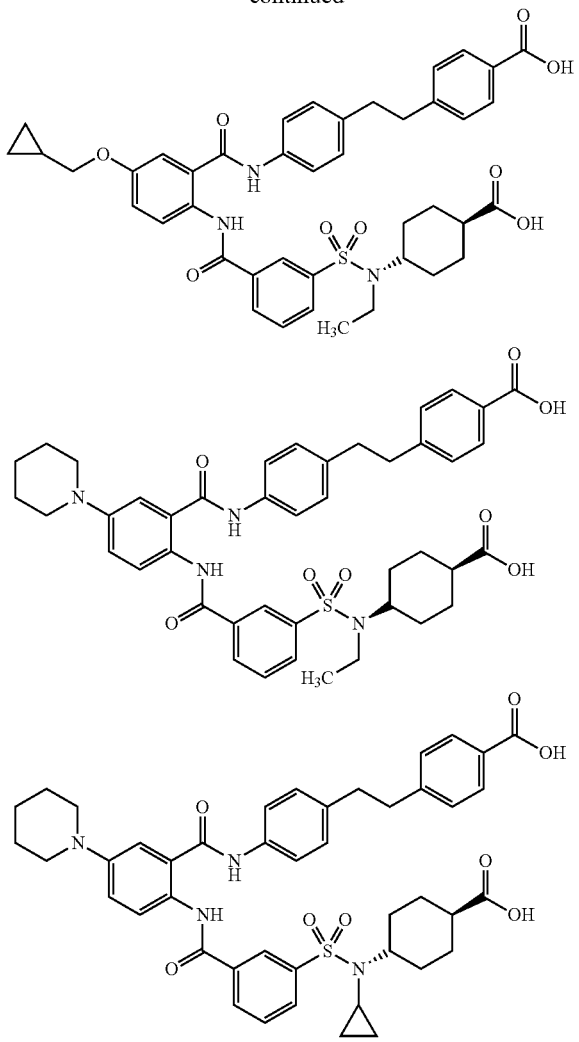

(Pharmacologically Acceptable Salt)

The term "pharmacologically acceptable salt thereof" indicates a salt that can be used as a medicament. When a compound has an acidic group or a basic group, a "salt with a base" or an "acid-added salt" can be formed by allowing the compound to react with a base or an acid. The term "pharmacologically acceptable salt thereof" indicates the thus formed salt.

In addition, the "pharmacologically acceptable salt thereof" also includes a hydrate thereof.

Preferred examples of the pharmacologically acceptable "salt with a base" of the compound include: alkali metal salts such as a sodium salt, a potassium salt, or a lithium salt; alkaline-earth metal salts such as a magnesium salt or a calcium salt; organic basic salts such as an N-methylmorpholine salt, a triethylamine salt, a tributylamine salt, a diisopropylethylamine salt, a dicyclohexylamine salt, an N-methylpiperidine salt, a pyridine salt, a 4-pyrrolidinopyridine salt, or a picoline salt; and amino acid salts such as a glycine salt, a lysine salt, an arginine salt, an ornithine salt, a glutamate, or an aspartate. Preferred examples include alkali metal salts and alkaline-earth metal salts.

Preferred examples of the pharmacologically acceptable "acid-added salt" of the compound include: inorganic acid salts including hydrohalides such as a hydrofluoride, a hydrochloride, a hydrobromide or a hydroiodide, a nitrate, a perchlorate, a sulfate, and a phosphate; organic acid salts including lower alkanesulfonates such as methanesulfonate, trifluoromethanesulfonate or ethanesulfonate, arylsulfonates such as benzenesulfonate or p-toluenesulfonate, an acetate, a malate, a fumarate, a succinate, a citrate, a ascorbate, a tartrate, an oxalate, and a maleate; and amino acid salts such as a glycine salt, a lysine salt, an arginine salt, an ornithine salt, a glutamate, and an aspartate. Among others, hydrohalides (in particular, a hydrochloride) are most preferable.

(Hydrate, Etc.)

When the compound of the present invention or a pharmacologically acceptable salt thereof is left in the air or is recrystallized, there is a case in which the compound or a salt thereof absorbs water content and thereby contains adsorbed water, or it is converted to a hydrate. The present invention includes various types of such hydrates, solvates, and crystalline polymorphisms.

(Isomer)

The compound of the present invention includes tautomers or geometric isomers, depending on the types of substituents. In the present description, the compound of the present invention is described only as a form of an isomer. However, the present invention also includes other isomers, and further, it includes separated isomers or a mixture thereof.

There is a case in which the compound of the present invention has asymmetric carbon atoms or axially chiral, and thus, optical isomers may be present based on these. The present invention also includes separated optical isomers or a mixture thereof.

(Isotope)

The compound of the present invention includes a labeled form, namely, a compound, one or two or more atoms of which are substituted with isotopes (e.g. $^2$H, $^3$H, $^{13}$C, $^{14}$C, $^{35}$S, etc.).

(Prodrug)

The present invention includes a pharmacologically acceptable prodrug of the compound of the present invention. The pharmacologically acceptable prodrug is a compound having a group that can be converted to an amino group, a hydroxyl group, a carboxyl group, or the like by solvolysis or under physiological conditions. Examples of such a group forming a prodrug include the groups described in Prog. Med., 5, 2157-2161 (1985).

More specific examples of the prodrug include:
when compounds have amino groups,
compounds whose amino groups are acylated, alkylated, or phosphorylated (e.g., compounds whose amino groups are eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated);
when compounds have hydroxyl groups,
compounds whose hydroxyl groups are acylated, alkylated, phosphorylated, or borated (e.g., compounds whose hydroxyl groups are acetylated, palmitoylated, propanoylated, pivaloylated, succinylated, fumarylated, alanylated, or dimethylaminomethylcarbonylated); and
when compounds have carboxy groups,
compounds whose carboxy groups are esterified or amidated (e.g. compounds whose carboxy groups are ethyl-esterified, phenyl-esterified, carboxymethyl-esterified, dimethylaminomethyl-esterified, pivaloyloxymethyl-esterified, ethoxycarbonyloxyethyl-esterified, amidated, or methylamidated).

(Production Method)

The compound of the present invention and a pharmacologically acceptable salt can be produced by applying various known synthetic methods, utilizing characteristics based on the basic structure thereof or the types of substituents.

Upon production, there is a case in which it is effective in terms of manufacturing technology that a functional group is substituted with a suitable protecting group (a group that can be easily converted to the functional group) during a stage from a raw material to an intermediate, depending on the type of the functional group. Examples of such a protecting group include the protecting groups described in P. G. M. Wuts and T. W. Greene, Greene's Protective Groups in Organic Synthesis (4th edition, 2006). These protecting groups may be appropriately selected and used, depending on reaction conditions.

In such a method, after the protecting group has been introduced and the reaction has been then performed, a desired compound can be obtained by removing the protecting group, as necessary. Moreover, as in the case of the aforementioned protecting group, the prodrug of the compound of the present invention can be produced by introducing a specific group during a stage from a raw material to an intermediate, or then further performing a reaction using the obtained compound. The reaction can be carried out by applying common methods such as esterification, amidation or dehydration.

Hereinafter, methods for producing the compound will be described. However, the production method is not limited to the following methods.

[Method A]

Method A is a method for producing the compounds (A-II) and (A-III) of the present invention.

Method A

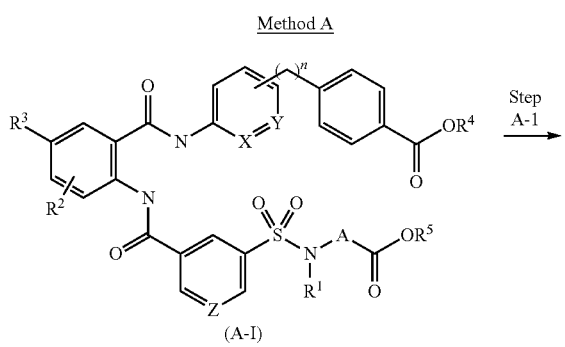

(A-I)

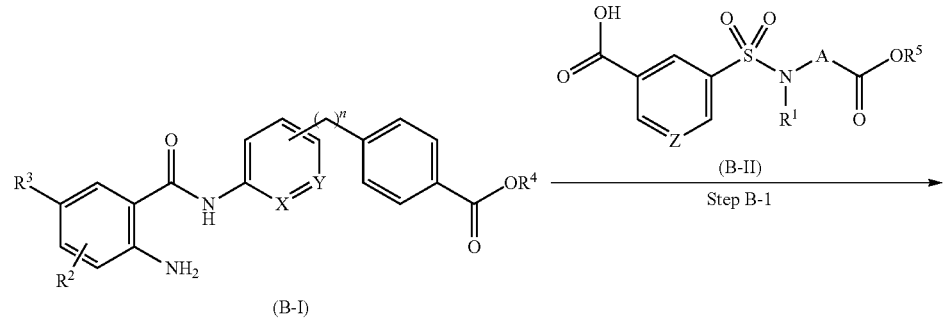

wherein $R^1$, $R^2$, $R^3$, A, X, Y, Z, and n are as defined above, $R^4$ and $R^5$, which are the same or different, each represent any group selected from C1-6 alkyl groups, and M represents a metal that forms a salt with a carboxy group.

(Step A-1) Step of Hydrolyzing Ester

This is a step of hydrolyzing an ester of the compound (A-I) in the presence of a base in a solvent to obtain the compound (A-II).

Preferred examples of the base used herein include alkali metal hydroxides such as sodium hydroxide or lithium hydroxide. A preferred example of the solvent used herein is a mixed solvent of water and tetrahydrofuran/methanol.

The reaction temperature is generally approximately 20° C. to 60° C., and the reaction time is generally approximately 1 to 10 hours.

(Step A-2) Step of Converting Carboxylic Acid into Salt

This is a step of treating the compound (A-II) with alkali metal alkoxide such as t-butoxy potassium to convert it into a salt. By the same method, various inorganic and organic salts can be produced.

For example, the compound (A-II) is dissolved in a solution such as tetrahydrofuran, and t-butoxy potassium is then added to the solution at a temperature of approximately 0° C. to 40° C., so that the compound is converted into a salt, thereby obtaining a potassium salt.

[Method B]

Method B is a method for producing a compound (B-III) that corresponds to the compound (A-I) used in Method A.

Method B

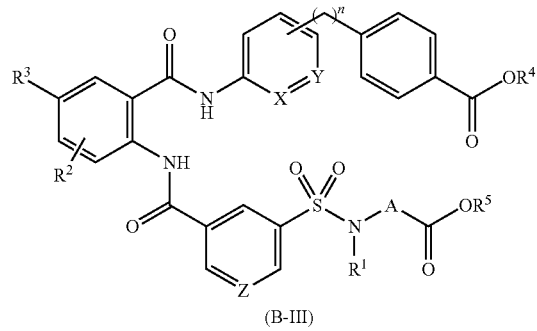

(B-III)

wherein $R^1$, $R^2$, $R^3$, A, X, Y, Z, and n are as defined above, $R^4$ and $R^5$, which are the same or different, each represent any groups selected from C1-6 alkyl groups.

(Step B-1) Step of Forming Amide by Condensation

This is a step of producing the compound (B-III) by (i) allowing a carboxylic acid of the compound (B-II) to react with oxalyl chloride to activate it and then allowing the resulting compound (B-II) to react with the compound (B-I), or by (ii) allowing the compound (B-II) to react with the compound (B-I) in the presence of a condensation agent.

In the case of (i), for example, oxalyl chloride and a small amount of dimethylformamide are added into a solution of the compound (B-II) in methylene chloride at a temperature of 0° C. to room temperature, and the obtained mixture is then left for a while, and thereafter, the compound (B-I) and a base such as pyridine are added to the reaction solution at a temperature of 0° C. to room temperature. In general, the reaction temperature is set at approximately room temperature to approximately 80° C., and the reaction time is set at approximately 1 to 24 hours.

In the case of (ii), for example, a base and a condensation agent are added to a solution of the compound (B-I) and the compound (B-II) in dimethylformamide or methylene chloride, and a reaction is then carried out. In general, the reaction temperature is approximately room temperature to approximately 80° C., and the reaction time is approximately 1 to 24 hours.

As a base used herein, a tertiary amine such as diisopropylethylamine is preferable.

Examples of the condensation agent used herein include:
1-[bis(dimethylamino)methylene]-1H-benzotriazolium-3-oxide hexafluorophosphate (hereinafter also referred to as "HBTU"),
2-(1H-7-azabenzotriazol-1-yl)-1,1,3,3-tetramethyluronium hexafluorophosphate (hereinafter also referred to as "HATU"),
4-(4,6-dimethoxy-1,3,5-triazin-2-yl)-4-methylmorpholinium chloride n-hydrate (hereinafter also referred to as "DMT-MM"), and
1-ethyl-3-(3-dimethylaminopropyl)carbodiimide hydrochloride (hereinafter also referred to as "WSC" or "EDCI").

[Method C]

Method C is a method for producing a compound (C-IV) that corresponds to the compound (B-I) used in Method B.

In Step C-1, when the reaction is carried out using a compound (C-I) whose nitro group is substituted with an amino group, the compound (C-IV) can be produced without performing Step C-2.

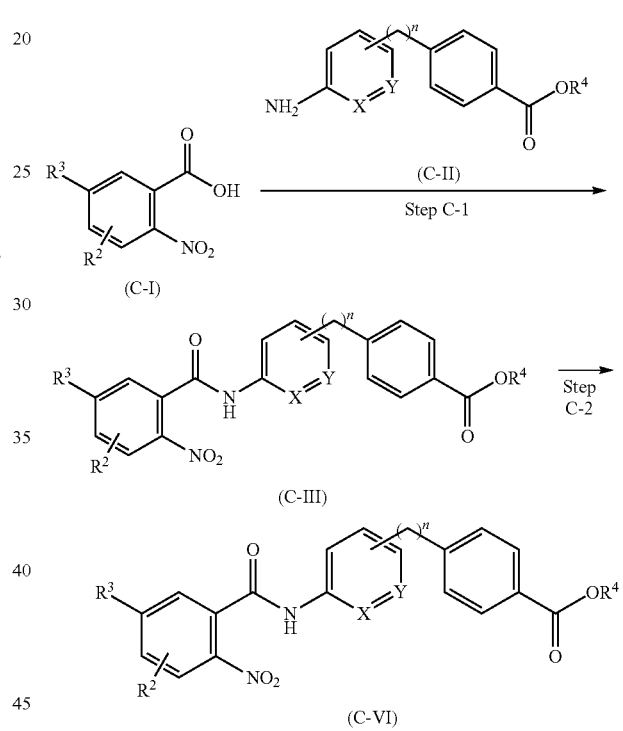

wherein $R^2$, $R^3$, X, Y, and n are as defined above, and $R^4$ represents any group selected from C1-6 alkyl groups.

(Step C-1) Step of Forming Amide by Condensation

This is a step of producing an amide under the same conditions as those in Step B-2 of Method B.

(Step C-2) Step of Reducing Nitro Group to Form Amino Group

This is a step of reacting a solution of the compound (C-III) under the hydrogen atmosphere in the presence of a metal catalyst such as 10% palladium carbon.

Preferred examples of the solvent used herein include ethers such as tetrahydrofuran, alcohols such as ethanol, and a mixed solvent of tetrahydrofuran/ethanol.

In general, the reaction temperature is approximately room temperature to approximately 60° C., and the reaction time is approximately 1 to 10 hours.

In addition, the present step can also be carried out by performing the reduction reaction using iron powder and ammonium chloride by heating them to reflux in an ethanol/water solvent.

[Method D]

Method D is a method for producing a compound (D-IV) that corresponds to the compound (C-III) used in Method C. In Method C, a substituent corresponding to $R^3$ has already been introduced during the initial step. When the substituent corresponding to $R^3$ is a group such as a saturated cyclic amino group or a dialkylamino group, $R^3$ can be introduced by performing steps such as Step D-1 and Step D-2, as in the case of Method D. Herein, a compound having a piperidine group is exemplified as a group such as a saturated cyclic amino group or a dialkylamino group.

Method D

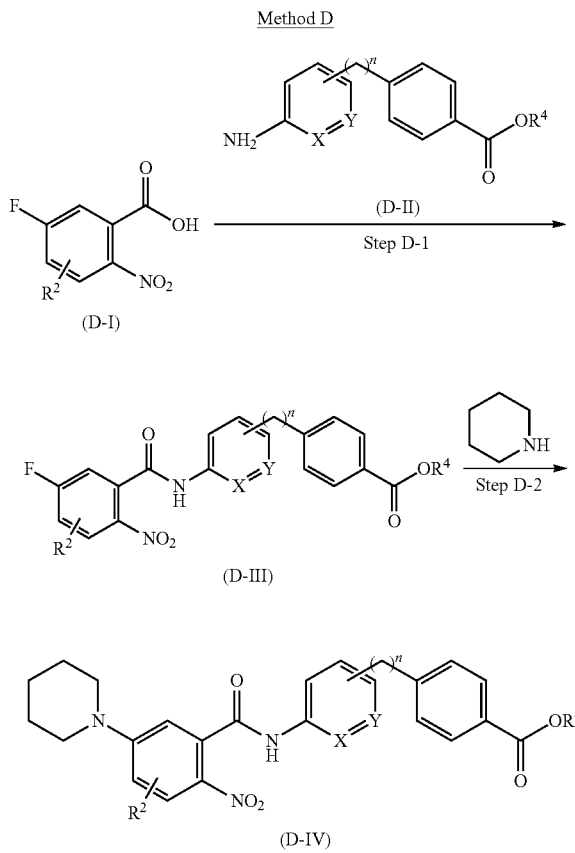

wherein $R^2$, X, Y, and n are as defined above, and $R^4$ represents any group selected from C1-6 alkyl groups.

(Step D-1) Step of Forming Amide by Condensation

This is a step of producing an amide under the same conditions as those in Step C-1 of Method C.

(Step D-2) Step of Introducing Substituent on Benzene Ring by Substitution Reaction This is a step of adding a saturated cyclic amine such as pyrrolidine, piperidine or diethylamine, or dialkylamine, to a solution of the compound (D-III), and then performing a reaction.

As a solvent used herein, ethers such as tetrahydrofuran are preferable.

The reaction temperature is generally room temperature to 80° C., and the reaction time is approximately 1 to 24 hours.

[Method E]

In general, a compound corresponding to the compound (C-II) used in Method C can be easily produced according to a known method. As an example, in Method E, a method for producing a compound (E-IV) that corresponds to the compound (C-II) will be described.

Method E

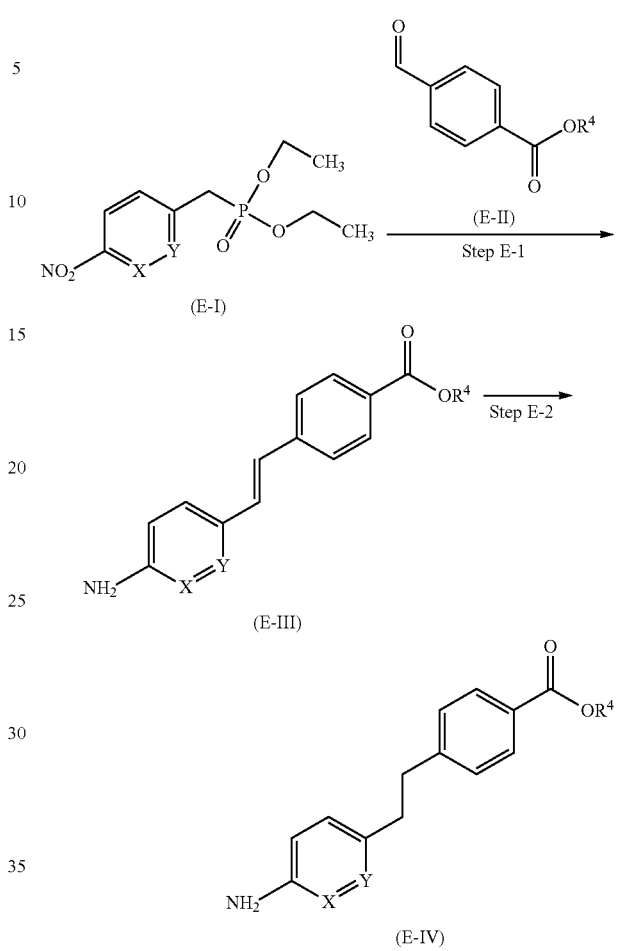

wherein X and Y are as defined above, and $R^4$ represents any group selected from C1-6 alkyl groups.

(Step E-1) Step of Forming Double Bond by Coupling Reaction

This is a step of treating the compound (E-I) with a base and then allowing the treated compound (E-I) to react with the compound (E-II) to obtain the compound (E-III).

As a base used herein, in addition to alkali metal hydride such as sodium hydride, bases that are generally used in this type of reaction may be used.

As a solvent used herein, ethers such as tetrahydrofuran are preferable.

The reaction temperature is generally 0° C. to 80° C., and the reaction time is approximately 1 to 24 hours.

(Step E-2) Step of Reducing Double Bond by Hydrogenation Reaction

This is a step of producing the compound (E-IV) under the same conditions as those in Step C-2 of Method C.

[Method F]

Method F is a method for producing a compound (F-VII) corresponding to the compound (D-IV) used in Method D. Method F is characterized in that a portion corresponding to the compound (D-II) in Method D is produced in the subsequent step (Step F-3).

Method F

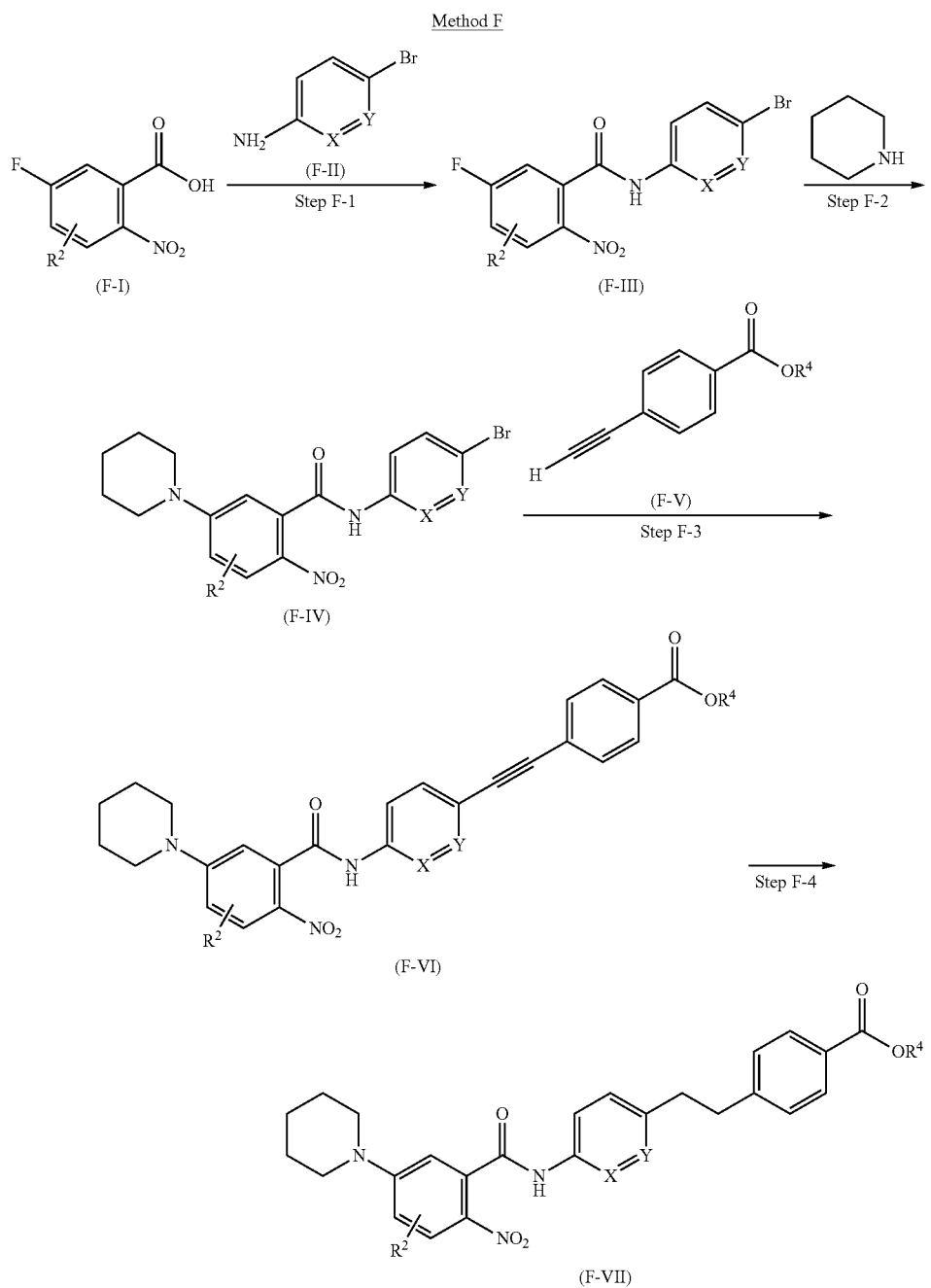

wherein $R^2$, X, and Y are as defined above, and $R^4$ represents any group selected from C1-6 alkyl groups.

(Step F-1) Step of Forming Amide by Condensation

This is a step of producing the compound (F-III) under the same conditions as those in Step C-1 of Method C.

(Step F-2) Step of Introducing Substituent on Benzene Ring by Substitution Reaction This is a step of producing the compound (F-IV) under the same conditions as those in Step D-2 of Method D.

(Step F-3) Step of Performing Coupling Reaction Using Transition Metal Catalyst

This is a step of subjecting the compound (F-IV) to a coupling reaction with the compound (F-V) to produce the compound (F-VI). For example, the compound (F-IV) is dissolved in ether such as tetrahydrofuran, and a catalyst such as copper(I) iodide or bis(triphenylphosphine)palladium(II) chloride and amine such as triethylamine are then added to the obtained solution. Thereafter, a reaction is carried out at a temperature of approximately room temperature to approximately 60° C. for approximately 1 to 24 hours.

As a solvent used herein, in addition to ethers, various solvents such as dimethylformamide, toluene, acetonitrile or ethanol can be used.

As a catalyst used herein, in addition to bis(triphenylphosphine)palladium(II) chloride, catalysts consisting of various transition metals and various ligands, such as tetrakis(triphenylphosphine)palladium(0), can be used.

As an amine used herein, in addition to triethylamine, various amines such as diisopropylethylamine, diethylamine or diisopropylamine can be used.

(Step F-4) Step of Reducing Triple Bound by Hydrogenation Reaction

This is a step of producing the compound (F-VII) under the same conditions as those in Step C-2 of Method C.

[Method G]

Method G is a method for producing a compound (G-IV) corresponding to the compound (B-II) used in Method B.

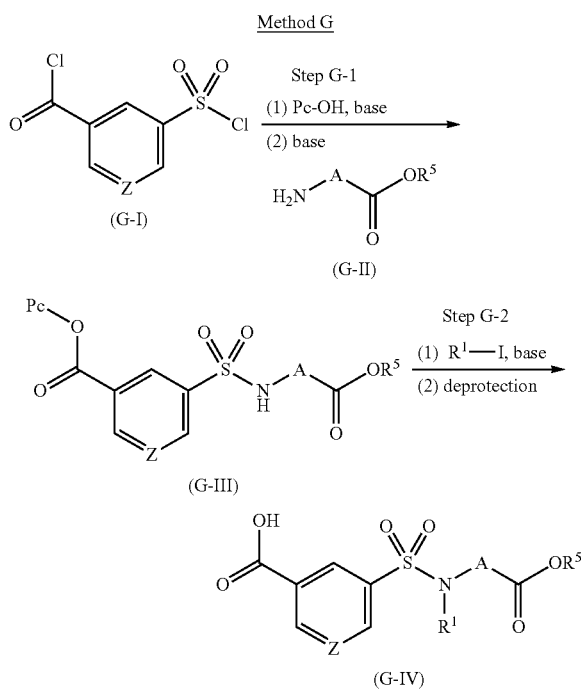

Method G wherein $R^1$, $R^5$, A, and Z are as defined above, and Pc represents a protecting group for carboxy groups, such as a trimethylsilylethyl group, a benzyl group or a t-butyl group.

(Step G-1) Steps of Esterification and Sulfonamidation (1) This is a step of allowing the compound (G-I) to react with 2-TMS-ethanol, benzyl alcohol or the like in the presence of a base to esterify it (wherein TMS indicates a trimethylsilyl group).

As a base, pyridine, diisopropylethylamine or the like is preferable, and as a solvent, methylene chloride is generally used.

The reaction temperature is generally 0° C. to room temperature, and the reaction time is generally approximately 2 hours.

(2) This is a step of allowing the resulting compound (G-I) to further react with the compound (G-II) in the presence of a base to obtain the compound (G-III).

As a base, pyridine is preferable, and as a solvent, methylene chloride is generally used.

The reaction temperature is generally approximately 0° C. to 40° C., and the reaction time is generally approximately 2 hours.

(Step G-2) Steps of N-Alkylation and Deprotection (1) This is a step of allowing the compound (G-III) to react with $R^1$—I in the presence of a base to N-alkylate it.

As a base, potassium carbonate is preferable, and as a solvent, dimethylformamide is generally used.

The reaction temperature is generally approximately room temperature to approximately 60° C., and the reaction time is generally approximately 1 hour to 3 days.

(2) This is a step of further performing a reaction under conditions for common deprotection of a carboxy group to obtain the compound (G-IV).

When the protecting group is a TMS-ethyl group, tetrabutylammonium fluoride is generally added to a tetrahydrofuran solution, and the reaction is then carried out.

The reaction temperature is generally approximately room temperature, and the reaction time is generally approximately 1 hour.

When the protecting group is a benzyl group, the reaction is generally carried out in an ethyl acetate solution under the hydrogen atmosphere and in the presence of a catalyst such as 10% palladium/carbon.

The reaction temperature is generally approximately room temperature, and the reaction time is generally approximately 4 hours.

When the protecting group is a t-butyl group, in general, trifluoroacetic acid is added, and the reaction is carried out in a methylene chloride solution.

The reaction temperature is generally approximately room temperature, and the reaction time is generally approximately 1 hour.

The compound produced by the above described method can be isolated and purified according to a known method such as extraction, precipitation, distillation, chromatography, fractional recrystallization, or recrystallization.

Moreover, when the compound or a production intermediate has asymmetric carbon, optical isomers are present. These optical isomers can be each isolated and purified by an ordinary method such as fractional recrystallization (salt fractionation) involving recrystallization with an appropriate salt, or column chromatography. A reference document for a method of fractionating an optical isomer from a racemate can be J. Jacques et al., "Enantiomers, Racemates and Resolution, John Wiley And Sons, Inc."

The pharmacological activity of the compound of the present invention was confirmed by the following test.

(Test Example) Rat $^{33}$P Phosphate Oral Challenge Test (Intestinal Phosphate Absorption Suppression Test)

Using male SD rats (5-7 week old) that had been fasted on the previous day, the compound described in Examples was suspended or dissolved in a solvent such as 0.5% methyl cellulose (3-6 mg/mL), and the thus obtained solution was administered to each rat at a dose of 30 mg/kg by a forcible oral administration. On the other hand, regarding a control group, the solvent was administered to each rat at a dose of 5 mL/kg. Thirty minutes after the administration, a $^{33}$P phosphate solution (8.3 mM $NaH_2PO_4$, 0.35 MBq/mL) was administered to the rats at a dose of 7.2 mL/kg by a forcible oral administration. Then, 15, 30, 60, and 120 minutes after the administration, blood was collected from the jugular vein of each rat under anesthesia with isoflurane. The radioactivity in 50 μL of serum was measured using a liquid scintillation counter, and the $AUC_{0-60min}$ was then calculated from the radioactivity value. The obtained value was defined as an amount of phosphate absorbed. The phosphate absorption-inhibiting activity of the compound was calculated according to the following expression.

Phosphate absorption-inhibiting activity (%)=[(100−the amount of phosphate absorbed of the compound administration group)/the amount of phosphate absorbed of the control group]×100

TABLE 1

| Example No. | Phosphorus absorption-inhibiting activity (%) |
|---|---|
| 4 | 42 |
| 10 | 53 |
| 12 | 79 |
| 14 | 76 |
| 15 | 82 |
| 26 | 60 |
| 27 | 57 |
| 28 | 60 |
| 29 | 72 |
| 30 | 69 |

(Dosage Form)

The administration may be carried out, either by oral administration using a tablet, a pill, a capsule, a granule, a powder, a liquid or the like, or by parenteral administration using an injection such as an intraarticular injection, an intravenous injection or an intramuscular injection, a suppository, an ophthalmic preparation, an eye ointment, a transdermal liquid, an ointment, a transdermal patch, a transmucosal liquid, a transmucosal patch, an inhalant, or the like.

As a solid composition for oral administration, a tablet, a powder, a granule or the like can be used. In such a solid composition, one or two or more active ingredients are mixed with at least one inactive excipient, for example, with lactose, mannitol, glucose, hydroxypropyl cellulose, microcrystalline cellulose, starch, polyvinyl pyrrolidone, and/or magnesium aluminometasilicate. The composition may comprise inactive additives, for example, a lubricant such as magnesium stearate, a disintegrant such as carboxymethyl starch sodium, a stabilizing agent, and a dissolution aid according to an ordinary method. The tablet or pill may be coated with a sugar-coated film, or a film of a gastric or enteric substance, as necessary.

A liquid composition for oral administration comprises a pharmaceutically acceptable emulsion, solution, suspension, syrup, elixir, etc., and it also comprises a commonly used inactive diluent, such as purified water or ethanol. The liquid composition may also comprise an adjuvant such as a solubilizing agent, a wetting agent, or a suspending agent, a sweetening agent, a flavoring agent, an aromatic, and an antiseptic, as well as an inactive diluent.

An injection for parenteral administration comprises an aseptic aqueous or non-aqueous solution, suspension, or emulsion. Examples of the aqueous solvent include distilled water for injection and normal saline. Examples of the non-aqueous solvent include propylene glycol, polyethylene glycol, vegetable oils such as olive oil, alcohols such as ethanol, and polysorbate 80. Such a composition may further comprise a tonicity agent, an antiseptic, a wetting agent, an emulsifying agent, a dispersing agent, a stabilizing agent, or a dissolution aid. These are sterilized, for example, by filtration using a bacteria-holding filter, or blending of a bactericide or irradiation. Moreover, it is also possible that an aseptic solid composition is produced, and that the solid composition is dissolved or suspended in sterile water or an aseptic solvent for injection before use, and is then used.

Examples of an external agent include an ointment, a plaster, a cream, a jelly, a cataplasm, a spray, a lotion, an ophthalmic preparation, and an eye ointment. The external agent comprises a commonly used ointment base, lotion base, aqueous or non-aqueous liquid, suspension, emulsion, etc. Examples of such an ointment or lotion base include polyethylene glycol, propylene glycol, white Vaseline, bleached beeswax, polyoxyethylene hydrogenated castor oil, glyceryl monostearate, stearyl alcohol, cetyl alcohol, lauromacrogol, and sorbitan sesquioleate.

As a transmucosal agent such as an inhalant or a transnasal agent, a solid, liquid, or semi-solid type is used, and it can be produced according to a conventionally known method. For example, a known excipient, and further, a pH adjusting agent, an antiseptic, a surfactant, a lubricant, a stabilizing agent, a thickening agent, etc. may be added, as appropriate. For administration, a device for appropriate inhalation or insufflation can be used. For instance, using a known device such as a metered-dose inhaler, or a sprayer, the compound can be administered alone, or in the form of a powder of a prescribed mixture thereof, or in combination with a pharmaceutically acceptable carrier and in the form of a solution or a suspension. A dry powder inhaler or the like may be used for single administration or multiple administration, and a dry powder or a powder-containing capsule can be used. Alternatively, the transmucosal agent may also have the form of a pressurized aerosol spray or the like, in which a suitable ejector, for example, chlorofluoroalkane, hydrofluroalkane or a preferred gas such as carbon dioxide is used.

(Dose)

In the case of general oral administration, it is adequate that the dose per day is approximately 0.001-100 mg/kg, preferably 0.1-30 mg/kg, more preferably 0.1-10 mg/kg per body weight. The oral agent is administered once or divided over two or more administrations. In the case of intravenous administration, the dose per day is suitably approximately 0.0001-10 mg/kg per body weight, and such a dose of compound is administered once a day or divided over several administrations. Moreover, a transmucosal agent is administered at a dose of approximately 0.001-100 mg/kg per body weight once a day or divided over several administrations. Taking into consideration symptoms, age, sex, etc., the applied dose is determined, as appropriate, depending on individual case.

(Combined Use)

The compound of the present invention can be used in combination with various therapeutic agents or preventive agents for diseases, to which the present compound is considered to exhibit effectiveness. In the combined use, the present compound and other agents may be coadministered, or the present compounds and the other agents may be administered separately, continuously or with desired intervals. The preparations for coadministration may be either combination drugs, or preparations that are formulated separately.

(Formulation Example 1) Powder 5 g of the compound of the present invention, 895 g of lactose and 100 g of corn starch are mixed using a blender to obtain a powder.

(Formulation Example 2) Granule 5 g of the compound of the present invention, 865 g of lactose and 100 g of low substituted hydroxypropyl cellulose are mixed, and thereafter 300 g of a 10% hydroxypropyl cellulose aqueous solution is added to the mixture, followed by kneading it. The kneaded product is granulated using an extrusion granulator and is then dried to obtain a granule.

(Formulation Example 3) Tablet 5 g of the compound of the present invention, 90 g of lactose, 34 g of corn starch, 20 g of crystalline cellulose, and 1 g of magnesium stearate are mixed using a blender, and the obtained mixture is subjected to a tablet-making machine to obtain a tablet.

EXAMPLES

Hereinafter, the present invention will be described more in detail in the following Examples and test examples. However, these examples are not intended to limit the scope of the present invention.

Elution in column chromatography performed in the Examples was carried out under observation by TLC (thin layer chromatography). In the TLC observation, Silica Gel 60F$_{254}$ manufactured by Merck was used as a TLC plate, and a solvent used as an elution solvent in the column chromatography was used as a developing solvent. As a detection method, a UV detector was adopted. As silica gel for column chromatography, silica gel SK-85 (230-400 meshes) manufactured by Merck or Chromatorex NH (200-350 meshes) manufactured by Fuji Silysia Chemical Ltd. was used. In addition to common column chromatography, an automatic chromatography apparatus (Purif-α2 or Purif-espoir2) of SHOKO SCIENTIFIC Co., Ltd. was used, as appropriate. The elution solvent was determined based on TLC observation.

Abbreviations used in the Examples have the following significances:

mg: milligram; g: gram; mL: milliliter; and MHz: megahertz

DCM: dichloromethane

DMF: N,N-dimethylformamide

THF: tetrahydrofuran

DIPEA: diisopropylethylamine

WSC: 1-ethyl-3-(3-dimethylaminopropyl)carbodiimide hydrochloride (Water Soluble Carbodiimide)

DMT-MM: 4(4,6-dimethoxy-1,3,5-triazin-2-yl)-4-methylmorpholinium chloride hydrate HBTU: 1-[bis(dimethylamino)methylene]-1H-benzotriazolium-3-oxide hexafluorophosphate HATU: 2-(1H-7-azabenzotriazol-1-yl)-1,1,3,3-tetramethyluronium hexafluorophosphate In the following Examples, nuclear magnetic resonance (which is hereinafter referred to as "$^1$H NMR") spectrum is described using tetramethylsilane as a standard substance, with a chemical shift value that is a δ value (ppm). With regard to a pattern of division, a singlet is indicated as s, a doublet is indicated as d, a triplet is indicated as t, a quartet is indicated as q, a multiplet is indicated as m, and a broad is indicated as br.

Mass spectrometry (which is hereinafter referred to as "MS") was carried out by an EI (Electron Ionization) method, an ESI (Electron Spray Ionization) method, or a FAB (Fast Atom Bombardment) method.

(Example 1) 4-[2-(4-{[2-({3-[(trans-4-Carboxycyclohexyl)(ethyl)sulfamoyl]benzoyl}amino)-5-fluorobenzoyl]amino}phenyl)ethyl]benzoic acid (1a) Methyl 4-(2-{4-[(2-amino-5-fluorobenzoyl)amino]phenyl}ethyl)benzoate WSC (370 mg) was added to a suspension of 2-amino-5-fluorobenzoic acid (200 mg) and methyl 4-[2-(4-aminophenyl)ethyl]benzoate (CAS registry number: 1346136-01-3, WO2011136269) (329 mg) in DCM (5 mL) at room temperature. The reaction mixture was stirred at room temperature for 23 hours, and thereafter, the reaction solution was diluted with a saturated ammonium chloride solution, and was then extracted with ethyl acetate. The organic layer was washed with saturated sodium hydrogen carbonate and a saturated saline, and was then dried over sodium sulfate. The resultant was filtrated and was then concentrated. The residue was purified by column chromatography to obtain 224 mg of the title compound (44%) in the form of a colorless solid.

(1b) Methyl 4-{2-[4-({2-[(3-{ethyl[trans-4-(methoxycarbonyl)cyclohexyl]sulfamoyl}benzoyl)amino]-5-fluorobenzoyl}amino)phenyl]ethyl}benzoate Oxalyl chloride (44 microL) and DMF (1 droplet) were added to a solution of 3-{ethyl[trans-4-(methoxycarbonyl)cyclohexyl]sulfamoyl}benzoic acid (CAS registry number: 1346136-17-1, WO2011136269) (100 mg) in DCM (3 mL) at room temperature. The reaction mixture was stirred at room temperature for 20 minutes, and thereafter, the reaction mixture was concentrated and was then diluted with DCM (2 mL). To this DCM solution, a solution of the compound (100 mg) obtained in Example (1a) and pyridine (51 microL) in DCM (2 mL) was added. The reaction mixture was stirred at room temperature for 3 hours, and thereafter, the reaction solution was diluted with a saturated ammonium chloride aqueous solution, and was then extracted with ethyl acetate. The organic layer was washed with a saturated sodium hydrogen carbonate aqueous solution, and was then dried over sodium sulfate. The resultant was filtrated and was then concentrated. The residue was purified by column chromatography to obtain 176 mg of the title compound (90%) in the form of a colorless solid.

(1c) 4-[2-(4-{[2-({3-[(trans-4-Carboxycyclohexyl)sulfamoyl]benzoyl}amino)-5-fluorobenzoyl]amino}phenyl)ethyl]benzoic acid A 1N NaOH aqueous solution (2 mL) was added to a solution of the compound (168 mg) obtained in Example (1b) in THF/methanol (1:1, 2 mL) at room temperature. The reaction mixture was heated to 60° C., and it was then stirred for 4 hours. Thereafter, the reaction mixture was cooled to room temperature, and 1N HCl was then added to the mixture (in an amount in which the reaction mixture became clouded). The obtained mixture was diluted with water, and was then extracted with ethyl acetate. The organic layer was washed with a saturated saline, and was then dried over sodium sulfate. The resultant was filtrated and was then concentrated. The residue was purified by column chromatography, and it was then ground in methanol to obtain 81 mg of the title compound (50%) in the form of a light pink solid.

(Example 2) 4-[2-(4-{[2-({3-[(trans-4-Carboxycyclohexyl)(ethyl)sulfamoyl]benzoyl}amino)-5-chlorobenzoyl]amino}phenyl)ethyl]benzoic acid (2a) Methyl 4-(2-{4-[(2-amino-5-chlorobenzoyl)amino]phenyl}ethyl)benzoate 186 mg of the title compound (58%) was obtained in the form of a colorless solid from 2-amino-5-chlorobenzoic acid (161 mg) and methyl 4-[2-(4-aminophenyl)ethyl]benzoate (CAS registry number: 1346136-01-3, WO2011136269) (200 mg) by the same method as that in Example (1a).

(2b) Methyl 4-{2-[4-({5-chloro-2-[(3-{ethyl[trans-4-(methoxycarbonyl)cyclohexyl]sulfamoyl}benzoyl)amino]benzoyl}amino)phenyl]ethyl}benzoate 262 mg of the title compound (80%) was obtained in the form of a colorless solid from 3-{ethyl[trans-4-(methoxycarbonyl)cyclohexyl]sulfamoyl}benzoic acid (CAS registry number: 1346136-17-1, WO2011136269) (191 mg) and the compound (176 mg) obtained in Example (2a) by the same method as that in Example (1b).

(2c) 4-[2-(4-{[2-({3-[(trans-4-Carboxycyclohexyl)(ethyl)sulfamoyl]benzoyl}amino)-5-chlorobenzoyl]amino}phenyl)ethyl]benzoic acid 209 mg of the title compound (86%) was obtained in the form of a colorless solid from the compound (252 mg) obtained in Example (2b) by the same method as that in Example (1c).

(Example 3) 4-[2-(4-{[5-Bromo-2-({3-[(trans-4-Carboxycyclohexyl)(ethyl)sulfamoyl]benzoyl}amino)benzoyl]amino}phenyl)ethyl]benzoic acid (3a) Methyl 4-(2-{4-[(2-amino-5-bromobenzoyl)amino]phenyl}ethyl)benzoate 130 mg of the title compound (62%) was obtained in the form of a colorless solid from 2-amino-5-bromobenzoic acid (100 mg) and methyl 4-[2-(4-aminophenyl)ethyl]benzoate (CAS registry number: 1346136-01-3, WO2011136269) (118 mg) by the same method as that in Example (1a).

(3b) Methyl 4-{2-[4-({5-bromo-2-[(3-{ethyl[trans-4-(methoxycarbonyl)cyclohexyl]sulfamoyl}benzoyl)amino]benzoyl}amino)phenyl]ethyl}benzoate 144 mg of the title compound (66%) was obtained in the form of a colorless solid from 3-{ethyl[trans-4-(methoxycarbonyl)cyclohexyl]sulfamoyl}benzoic acid (CAS registry number: 1346136-17-1, WO2011136269) (120 mg) and the compound (123 mg) obtained in Example (3a) by the same method as that in Example (1b).

(3c) 4-[2-(4-{[5-Bromo-2-({3-[(trans-4-carboxycyclohexyl)(ethyl)sulfamoyl]benzoyl}amino)benzoyl]amino}phenyl)ethyl]benzoic acid 22 mg of the title compound (17%) was obtained in the form of a colorless solid from the compound (132 mg) obtained in Example (3b) by the same method as that in Example (1c).

(Example 4) Dipotassium 4-[2-(4-{[5-bromo-2-({3-[(trans-4-carboxylatocyclohexyl)(ethyl)sulfamoyl]benzoyl}amino)benz oyl]amino}phenyl)ethyl]benzoate t-Butoxy potassium (327 mg) was added to a suspension of the compound (1.13 g) obtained in Example 3 in THF (10 mL) at room temperature. Methanol (5 mL) was added to the obtained reaction mixture (wherein a majority of the reaction mixture was dissolved therein but some portion remained as an insoluble matter). In order to remove such an insoluble matter, the reaction mixture was filtrated and was then concentrated. The residue was ground in diisopropyl ether, and was then filtrated. The obtained solid was purified by reverse phase column chromatography to obtain 1.12 g of the title compound (90%) in the form of a colorless solid.

(Example 5) 4-[2-(4-{[4-Bromo-2-({3-[(trans-4-carboxycyclohexyl)(ethyl)sulfamoyl]benzoyl}amino)benzoyl]amino}phenyl)ethyl]benzoic acid (5a) Methyl 4-(2-{4-[(2-amino-4-bromobenzoyl)amino]phenyl}ethyl)benzoate 209 mg of the title compound (95%) was obtained in the form of a colorless solid from 2-amino-4-bromobenzoic acid (203 mg) and methyl 4-[2-(4-aminophenyl)ethyl]benzoate (CAS registry number: 1346136-01-3, WO2011136269) (200 mg) by the same method as that in Example (1a).

(5b) Methyl 4-{2-[4-({4-bromo-2-[(3-{ethyl[trans-4-(methoxycarbonyl)cyclohexyl]sulfamoyl}benzoyl)amino]benzo yl}amino)phenyl]ethyl}benzoate 304 mg of the title compound (85%) was obtained in the form of a colorless solid from 3-{ethyl[trans-4-(methoxycarbonyl)cyclohexyl]sulfamoyl}benzoic acid (CAS registry number: 1346136-17-1, WO2011136269) (181 mg) and the compound (202 mg) obtained in Example (5a) by the same method as that in Example (1b).

(5c) 4-[2-(4-{[4-Bromo-2-({3-[(trans-4-carboxycyclohexyl)(ethyl)sulfamoyl]benzoyl}amino)benzoyl]amino}phenyl)ethyl]benzoic acid 200 mg of the title compound (70%) was obtained in the form of a light yellow solid from the compound (297 mg) obtained in Example (5b) by the same method as that in Example (1c).

(Example 6) 4-[2-(4-{[2-({3-[(trans-4-Carboxycyclohexyl)(ethyl)sulfamoyl]benzoyl}amino)-5-(trifluoromethyl)benzoyl]amino}phenyl)ethyl]benzoic acid (6a) Methyl 4-[2-(4-{[2-amino-5-(trifluoromethyl)benzoyl]amino}phenyl)ethyl]benzoate 286 mg of the title compound (83%) was obtained in the form of a colorless solid from 2-amino-5-(trifluoromethyl)benzoic acid (193 mg) and methyl 4-[2-(4-aminophenyl)ethyl]benzoate (CAS registry number: 1346136-01-3, WO2011136269) (200 mg) by the same method as that in Example (1a).

(6b) Methyl 4-{2-[4-({2-[(3-{ethyl[trans-4-(methoxycarbonyl)cyclohexyl]sulfamoyl}benzoyl)amino]-5-(trifluoromethyl)benzoyl}amino)phenyl]ethyl}benzoate 281 mg of the title compound (56%) was obtained in the form of a colorless solid from 3-{ethyl[trans-4-(methoxycarbonyl)cyclohexyl]sulfamoyl}benzoic acid (CAS registry number: 1346136-17-1, WO2011136269) (254 mg) and the compound (277 mg) obtained in Example (6a) by the same method as that in Example (1b).

(6c) 4-[2-(4-{[2-({3-[(trans-4-Carboxycyclohexyl)(ethyl)sulfamoyl]benzoyl}amino)-5-(trifluoromethyl)benzoyl]amino}phenyl)ethyl]benzoic acid 182 mg of the title compound (70%) was obtained in the form of a colorless solid from the compound (271 mg) obtained in Example (6b) by the same method as that in Example (1c).

(Example 7) Dipotassium 4-[2-(4-{[2-({3-[(trans-4-carboxylatocyclohexyl)(ethyl)sulfamoyl]benzoyl}amino)-5-(trifluoromethyl)benzoyl]amino}phenyl)ethyl]benzoate The title compound was obtained from the compound obtained in Example 6 by the same method as that in Example 4.

(Example 8) 4-[2-(4-{[2-({3-[(trans-4-Carboxycyclohexyl)(ethyl)sulfamoyl]benzoyl}amino)-4,5-dichlorobenzoyl]amino}phenyl)ethyl]benzoic acid (8a) Methyl 4-(2-{4-[(2-amino-4,5-dichlorobenzoyl)amino]phenyl}ethyl)benzoate 346 mg of the title compound (37%) was obtained in the form of a light yellow solid from 2-amino-4,5-dichlorobenzoic acid (CAS Registry Number: 20776-61-8) and methyl 4-[2-(4-aminophenyl)ethyl]benzoate (CAS registry number: 1346136-01-3, WO2011136269) (545 mg) by a method similar to that in Example (1a) (wherein DMT-MM was used instead of WSC).

(8b) Methyl 4-{2-[4-({4,5-dichloro-2-[(3-{ethyl[trans-4-(methoxycarbonyl)cyclohexyl]sulfamoyl}benzoyl)amino]benzo yl}amino)phenyl]ethyl}benzoate 365 mg of the title compound (59%) was obtained in the form of a colorless solid from 3-{ethyl[trans-4-(methoxycarbonyl)cyclohexyl]sulfamoyl}benzoic acid (CAS registry number: 1346136-17-1, WO2011136269) (432 mg) and the compound (345 mg) obtained in Example (8a) by the same method as that in Example (1b).

(8c) 4-[2-(4-{[2-({3-[(trans-4-Carboxycyclohexyl)(ethyl)sulfamoyl]benzoyl}amino)-4,5-dichlorobenzoyl]amino}phenyl)ethyl]benzoic acid 297 mg of the title compound (84%) was obtained in the form of a colorless solid from the compound (365 mg) obtained in Example (8b) by the same method as that in Example (1c).

(Example 9) 4-[2-(4-{[2-({3-[(trans-4-Carboxycyclohexyl)(ethyl)sulfamoyl]benzoyl}amino)-5-(pyrrolidin-1-yl)benzoyl]amino}phenyl)ethyl]benzoic acid (9a) Methyl 4-(2-{4-[(5-fluoro-2-nitrobenzoyl)amino]phenyl}ethyl)benzoate 6.70 g of the title compound (79%) was obtained in the form of a light yellow solid from 5-fluoro-2-nitrobenzoic acid (4.07 g) and methyl 4-[2-(4-aminophenyl)ethyl]benzoate (CAS registry number: 1346136-01-3, WO2011136269) (5.10 g) by the same method as that in Example (1a).

(9b) Methyl 4-[2-(4-{[2-nitro-5-(pyrrolidin-1-yl)benzoyl]amino}phenyl)ethyl]benzoate A solution of the compound (1.98 g) obtained in Example (9a) and pyrrolidine (1.15 mL) in THF (15 mL) was stirred at room temperature for 22 hours. Thereafter, the reaction mixture was concentrated, was then stirred in water and ethyl acetate, and was then concentrated. The residue was ground in ethanol, was then collected by filtration, and was then dried under reduced pressure to obtain 2.30 g of the title compound (quantitative yield) in the form of a yellow solid.

(9c) Methyl 4-[2-(4-{[2-amino-5-(pyrrolidin-1-yl)benzoyl]amino}phenyl)ethyl]benzoate A suspension of the compound (2.30 g) obtained in Example (9b) and palladium carbon (10 wt %, 0.46 g) in THF/ethanol (1:1, 40 mL) was stirred under the hydrogen atmosphere at 50° C. for 6 hours. Thereafter, the reaction mixture was filtrated with Celite, and was then concentrated. The residue was purified by column chromatography. The obtained solid was ground in diisopropanol, was collected by filtration, and was then dried under reduced pressure to obtain 1.70 g of the title compound (82%) in the form of a green solid.

(9d) Methyl 4-{2-[4-({2-[(3-{ethyl[trans-4-(methoxycarbonyl)cyclohexyl]sulfamoyl}benzoyl)amino]-5-(pyrrolidin-1-yl)benzoyl}amino)phenyl]ethyl}benzoate A solution of the compound (500 mg) obtained in Example (9c), 3-{ethyl[trans-4-(methoxycarbonyl)cyclohexyl]sulfamoyl}benzoic acid (CAS registry number: 1346136-17-1, WO2011136269) (500 mg), HBTU (857 mg), and DIPEA (0.500 mL) in DMF (5 mL) was stirred at room temperature for 16 hours. Thereafter, the reaction mixture was diluted with water, and was then extracted with ethyl acetate. The organic layer was washed with a saturated saline, and was then dried over magnesium sulfate. The resultant was filtrated and was then concentrated. The residue was purified by column chromatography to obtain 870 mg of the title compound (97%) in the form of a yellow solid.

(9e) 4-[2-(4-{[2-({3-[(trans-4-Carboxycyclohexyl)(ethyl)sulfamoyl]benzoyl}amino)-5-(pyrrolidin-1-yl)benzoyl]amino}phenyl)ethyl]benzoic acid 498 mg of the title compound (60%) was obtained in the form of a yellow solid from the compound (865 mg) obtained in Example (9d) by the same method as that in Example (1c).

(Example 10) Dipotassium 4-[2-(4-{[2-({3-[(trans-4-carboxylatocyclohexyl)(ethyl)sulfamoyl]benzoyl}amino)-5-(pyrrolidin-1-yl)benzoyl]amino}phenyl)ethyl]benzoate 225 mg of the title compound (quantitative yield) was obtained in the form of a green solid from the compound (200 mg) obtained in Example 9 by the same method as that in Example 4.

(Example 11) 4-[2-(4-{[2-({3-[(trans-4-Carboxycyclohexyl)(ethyl)sulfamoyl]benzoyl}amino)-5-(piperidin-1-yl)benzoyl]amino}phenyl)ethyl]benzoic acid (11a) Methyl 4-[2-(4-{[2-nitro-5-(piperidin-1-yl)benzoyl]amino}phenyl)ethyl]benzoate 10.3 g of the title compound (95%) was obtained in the form of a yellow solid from the compound (9.42 g) obtained in Example (9a) and piperidine (6.6 mL) by a method similar to that in Example (9b) (the reaction temperature: 50° C.).

(11b) Methyl 4-[2-(4-{[2-amino-5-(piperidin-1-yl)benzoyl]amino}phenyl)ethyl]benzoate 9.30 g of the title compound (96%) was obtained in the form of a green amorphous substance from the compound (10.3 g) obtained in Example (11a) by the same method as that in Example (9c).

(11c) Methyl 4-{2-[4-({2-[(3-{ethyl[trans-4-(methoxycarbonyl)cyclohexyl]sulfamoyl}benzoyl)amino]-5-(piperidin-1-yl)benzoyl}amino)phenyl]ethyl}benzoate 15.4 g of the title compound (94%) was obtained in the form of a yellow solid from 3-{ethyl[trans-4-(methoxycarbonyl)cyclohexyl]sulfamoyl}benzoic acid (CAS registry number: 1346136-17-1, WO2011136269) (9.0 g) and the compound (9.29 g) obtained in Example (11b) by the same method as that in Example (9d).

(11d) 4-[2-(4-{[2-({3-[(trans-4-Carboxycyclohexyl)(ethyl)sulfamoyl]benzoyl}amino)-5-(piperidin-1-yl)benzoyl]amino}phenyl)ethyl]benzoic acid 14.7 g of the title compound (98%) was obtained in the form of a yellow solid from the compound (15.4 g) obtained in Example (11c) by the same method as that in Example (1c).

(Example 12) Dipotassium 4-[2-(4-{[2-({3-[(trans-4-carboxylatocyclohexyl)(ethyl)sulfamoyl]benzoyl}amino)-5-(piperidin-1-yl)benzoyl]amino}phenyl)ethyl]benzoate 16.8 g of the title compound (94%) was obtained in the form of a yellow solid from the compound (16.4 g) obtained in Example 11 by the same method as that in Example 4.

(Example 13) 4-[2-(4-{[2-({3-[(trans-4-Carboxycyclohexyl)(ethyl)sulfamoyl]benzoyl}amino)-5-(diethylamino)benzoyl]amino}phenyl)ethyl]benzoic acid (13a) Methyl 4-[2-(4-{[5-(diethylamino)-2-nitrobenzoyl]amino}phenyl)ethyl]benzoate 2.12 g of the title compound (94%) was obtained in the form of a yellow solid from the compound (2.00 g) obtained in Example (9a) and diethylamine (1.5 mL) by the same method as that in Example (9b).

(13b) Methyl 4-[2-(4-{[2-amino-5-(diethylamino)benzoyl]amino}phenyl)ethyl]benzoate 1.97 g of the title compound (99%) was obtained in the form of a yellow solid from the compound (2.11 g) obtained in Example (13a) by the same method as that in Example (9c).

(13c) Methyl 4-{2-[4-({5-(diethylamino)-2-[(3-{ethyl[trans-4-(methoxycarbonyl)cyclohexyl]sulfamoyl}benzoyl)amino]benzoyl}amino)phenyl]ethyl}benzoate 782 mg of the title compound (88%) was obtained in the form of a yellow solid from 3-{ethyl[trans-4-(methoxycarbonyl)cyclohexyl]sulfamoyl}benzoic acid (CAS registry number: 1346136-17-1, WO2011136269) (495 mg) and the compound (500 mg) obtained in Example (13b) by the same method as that in Example (9d).

(13d) 4-[2-(4-{[2-({3-[(trans-4-Carboxycyclohexyl)(ethyl)sulfamoyl]benzoyl}amino)-5-(diethylamino)benzoyl]amino}phenyl)ethyl]benzoic acid 597 mg of the title compound (80%) was obtained in the form of a yellow solid from the compound (775 mg) obtained in Example (13c) by the same method as that in Example (1c).

(Example 14) Dipotassium 4-[2-(4-{[2-({3-[(trans-4-carboxylatocyclohexyl)(ethyl)sulfamoyl]benzoyl}amino)-5-(diethylamino)benzoyl]amino}phenyl)ethyl]benzoate 450 mg of the title compound (quantitative yield) was obtained in the form of a yellow solid from the compound (380 mg) obtained in Example 13 by the same method as that in Example 4.

(Example 15) Dipotassium 4-[2-(4-{[2-({3-[(trans-4-carboxylatocyclohexyl)(ethyl)sulfamoyl]benzoyl}amino)-5-(cyclopropylmethoxy)benzoyl]amino}phenyl)ethyl]benzoate (15a) Methyl 5-(cyclopropylmethoxy)-2-nitrobenzoate (Bromomethyl)cyclopropane (1.0 mL) was added to a suspension of methyl 5-hydroxy-2-nitrobenzoate (1.40 g) and potassium carbonate (2.94 g) in acetone (30 mL) at room temperature. The reaction mixture was heated to 50° C., and was then stirred for 7 hours. Thereafter, the reaction mixture was cooled to room temperature, and it was then diluted with DMF (30 mL), followed by stirring at 60° C. for 9 hours. Thereafter, the reaction mixture was cooled to room temperature, was then diluted with water, and was then extracted with ethyl acetate. The organic layer was washed with water and a saturated saline, and was then dried over magnesium sulfate. The resultant was filtrated and was then concentrated. The residue was purified by column chromatography to obtain 1.68 g of the title compound (94%) in the form of a yellow oil.

(15b) 5-(Cyclopropylmethoxy)-2-nitrobenzoic acid

A 5 N sodium hydroxide aqueous solution (4 mL) and water (4 mL) were added to methanol/THF (1:1, 20 mL) of the compound (1.67 g) obtained in Example (15a) at room temperature. The reaction mixture was stirred for 1 hour, and a 2 N hydrochloric acid aqueous solution was added to the reaction solution to convert it to an acidic solution. The obtained solution was extracted with ethyl acetate. The organic layer was washed with a saturated saline, and was then dried over magnesium sulfate. The resultant was filtrated and was then concentrated. The residue was dried under reduced pressure to obtain 1.40 g of the title compound (89%) in the form of a light yellow solid.

(15c) Methyl 4-[2-(4-{[5-(cyclopropylmethoxy)-2-nitrobenzoyl]amino}phenyl)ethyl]benzoate 520 mg of the title compound (78%) was obtained in the form of a colorless solid from the compound (365 mg) obtained in Example (15b) and methyl 4-[2-(4-aminophenyl)ethyl]benzoate (CAS registry number: 1346136-01-3, WO2011136269) (357 mg) by the same method as that in Example (1a).

(15d) Methyl 4-[2-(4-{[2-amino-5-(cyclopropylmethoxy)benzoyl]amino}phenyl)ethyl]benzoate 462 mg of the title compound (96%) was obtained in the form of a yellow solid from the compound (512 mg) obtained in Example (15c) by the same method as that in Example (9c).

(15e) Methyl 4-{2-[4-({5-(cyclopropylmethoxy)-2-[(3-{ethyl[trans-4-(methoxycarbonyl)cyclohexyl]sulfamoyl}benzoyl)amino]benzo yl}amino)phenyl]ethyl}benzoate 715 mg of the title compound (88%) was obtained in the form of a light red solid from 3-{ethyl[trans-4-(methoxycarbonyl)cyclohexyl]sulfamoyl}benzoic acid (CAS registry number: 1346136-17-1, WO2011136269) (454 mg) and the compound (455 mg) obtained in Example (13b) by the same method as that in Example (9d).

(15f) Dipotassium 4-[2-(4-{[2-({3-[(trans-4-carboxylatocyclohexyl)(ethyl)sulfamoyl]benzoyl}amino)-5-(cyclopropylmethoxy)benzoyl]amino}phenyl)ethyl]benzoate 654 mg of dicarboxylic acid (95%) was obtained in the form of a yellow solid from the compound (710 mg) obtained in Example (15e) by the same method as that in Example (1c). Then, 505 mg of the title compound (quantitative yield) was obtained in the form of a yellow solid from the dicarboxylic acid (445 mg) by the same method as that in Example 4.

(Example 16) Dipotassium 4-[2-(4-{[2-({3-[(trans-4-carboxycyclohexyl)(methyl)sulfamoyl]benzoyl}amino)-5-(piperidin-1-yl)benzoyl]amino}phenyl)ethyl]benzoate (16a) Benzyl 3-{[trans-4-(methoxycarbonyl)cyclohexyl]sulfamoyl}benzoate A solution of pyridine (5.7 mL) and benzyl alcohol (7.3 mL) in DCM (70 mL) was slowly added to a solution of 3-(chlorosulfonyl)benzoylchloride (17.2 g) in DCM (300 mL) at 0° C. over 15 minutes or more. Two hours later, methyl trans-4-aminocyclohexanecarboxylate hydrochloride (CAS registry number: 61367-07-5, Journal of Medicinal Chemistry 1977, 20, 279-90.) (14.3 g) and DIPEA (25 mL) were added to the reaction mixture at room temperature. In order to efficiently stir a precipitate generated during the reaction, DIPEA (25 mL) was further added to the mixture. After the mixture had been stirred for 17 hours, the reaction mixture was diluted with ethyl acetate, was then washed with water and a saturated saline, and was then dried over sodium sulfate. The resultant was filtrated and was then concentrated. The residue was purified by column chromatography to obtain 24.5 g of the title compound (81%) in the form of a light yellow oil.

(16b) Benzyl 3-{[trans-4-(methoxycarbonyl)cyclohexyl](methyl)sulfamoyl}benzoate

Potassium carbonate (5.52 g) was added to a solution of the compound (8.61 g) obtained in Example (16a) in DMF (200 mL) at room temperature, and iodomethane (1.40 mL) was then added dropwise to the solution at room temperature. The reaction mixture was stirred for 3 days, was then diluted with a saturated ammonium chloride aqueous solution, and was then extracted with ethyl acetate and hexane. The organic layer was washed with water and a saturated saline, and was then dried over sodium sulfate. The resultant was filtrated and was then concentrated. The residue was purified by column chromatography to obtain 8.47 g of the title compound (95%) in the form of a light yellow oil.

(16c) 3-{[trans-4-(Methoxycarbonyl)cyclohexyl](methyl)sulfamoyl}benzoic acid

A suspension of the compound (8.47 g) obtained in Example (16b) and palladium carbon (10 wt %, 0.85 g) in ethyl acetate (100 mL) was stirred under the hydrogen atmosphere at room temperature for 4 hours. Thereafter, the reaction mixture was filtrated with Celite, and was then concentrated. The resultant was dried under reduced pressure to obtain 6.76 g of the title compound (92%) in the form of a colorless solid.

(16d) Methyl 4-{2-[4-({2-[(3-{[trans-4-(methoxycarbonyl)cyclohexyl](methyl)sulfamoyl}benzoyl)amino]-5-(piperidin-1-yl)benzoyl}amino)phenyl]ethyl}benzoate A solution of the compound (553 mg) obtained in Example (11b) and DIPEA (0.800 mL) in DMF (5 mL) was added dropwise to a solution of the compound (605 mg) obtained in Example (16c) and HATU (865 mg) in DMF (10 mL) at room temperature. The reaction mixture was heated at 80° C. for 24 hours, and thereafter, it was cooled to room temperature. The reaction mixture was diluted with a saturated ammonium chloride aqueous solution, and was then extracted with ethyl acetate/hexane (4:1). The organic layer was washed with water and a saturated saline, and was then dried over sodium sulfate. The resultant was filtrated and was then concentrated. The residue was purified by column chromatography to obtain 549 mg of the title compound (61%) in the form of a yellow oil.

(16e) Dipotassium 4-[2-(4-{[2-({3-[(trans-4-carboxycyclohexyl)(methyl)sulfamoyl]benzoyl}amino)-5-(piperidin-1-yl)benzoyl]amino}phenyl)ethyl]benzoate 526 mg of a dicarboxylic acid compound was obtained in the form of a colorless solid from the compound (545 mg) obtained in Example (16d) by the same method as that in Example (1c).

Then, 184 mg of the title compound (75%, two steps) was obtained in the form of a light yellow solid from the dicarboxylic acid compound (229 mg) by the same method as that in Example 4.

(Example 17) Dipotassium 4-[2-(4-{[2-({3-[(trans-4-carboxylatocyclohexyl)(2-methoxyethyl) sulfamoyl]benzoyl}amino)-5-(piperidin-1-yl)benzoyl]amino}phenyl)ethyl]benzoate (17a) Benzyl 3-{[trans-4-(methoxycarbonyl)cyclohexyl](2-methoxyethyl)sulfamoyl}benzoate 11.4 g of the title compound (90%) was obtained in the form of a light yellow solid from the compound (11.1 g) obtained in Example (16a) and 2-bromoethyl methyl ether (2.8 mL) by the same method as that in Example (16b).

(17b) 3-{[trans-4-(Methoxycarbonyl)cyclohexyl](2-methoxyethyl)sulfamoyl}benzoic acid 8.99 g of the title compound (97%) was obtained in the form of a light yellow oil from the compound (11.4 g) obtained in Example (17a) by the same method as that in Example (16c).

(17c) Methyl 4-{2-[4-({2-[(3-{[trans-4-(methoxycarbonyl)cyclohexyl](2-methoxyethyl)sulfamoyl}benzoyl)amino]-5-(piperidin-1-yl)benzoyl}amino)phenyl]ethyl}benzoate 819 mg of the title compound (69%) was obtained in the form of a yellow amorphous substance from the compound (856 mg) obtained in Example (17b) and the compound (650 mg) obtained in Example (11b) by the same method as that in Example (16d).

(17d) Dipotassium 4-[2-(4-{[2-({3-[(trans-4-carboxylatocyclohexyl)(2-methoxyethyl) sulfamoyl]benzoyl}amino)-5-(piperidin-1-yl)benzoyl]amino}phenyl)ethyl]benzoate 761 mg of a dicarboxylic acid compound (99%) was obtained in the form of a yellow solid from the compound (798 mg) obtained in Example (17c) by the same method as that in Example (1c).

Then, 357 mg of the title compound (91%) was obtained in the form of a yellow solid from the dicarboxylic acid compound (360 mg) by the same method as that in Example 4.

(Example 18) Dipotassium 4-[2-(4-{[2-({3-[(trans-4-carboxylatocyclohexyl)(cyclopropylmethyl)sulfamoyl]benzoyl}amino)-5-(piperidin-1-yl)benzoyl]amino}phenyl)ethyl]benzoate (18a) Benzyl 3-{(cyclopropylmethyl) [trans-4-(methoxycarbonyl)cyclohexyl]sulfamoyl}benzoate 225 mg of the title compound (41%) was obtained in the form of a colorless oil from the compound (490 mg) obtained in Example (16a) and (bromomethyl)cyclopropane (0.125 mL) by the same method as that in Example (16b).

(18b) Methyl 4-{2-[4-({2-[(3-{(cyclopropylmethyl)[trans-4-(methoxycarbonyl)cyclohexyl]sulfamoyl}benzoyl)amino]-5-(piperidin-1-yl)benzoyl}amino)phenyl]ethyl}benzoate Carboxylic acid was obtained from the compound (225 mg) obtained in Example (18a) by the same method as that in Example (16c). Then, 409 mg of the title compound (quantitative yield, two steps) was obtained in the form of a yellow oil from the carboxylic acid and the compound (381 mg) obtained in Example (11b) by the same method as that in Example (16d).

(18c) Dipotassium 4-[2-(4-{[2-({3-[(trans-4-carboxylatocyclohexyl)(cyclopropylmethyl)sulfamoyl]benzoyl}amino)-5-(piperidin-1-yl)benzoyl]amino}phenyl)ethyl]benzoate 331 mg of a dicarboxylic acid compound (84%) was obtained in the form of a yellow solid from the compound (409 mg) obtained in Example (18b) by the same method as that in Example (1c).

Then, 220 mg of the title compound (94%) was obtained in the form of a yellow amorphous substance from the dicarboxylic acid compound (214 mg) by the same method as that in Example 4.

(Example 19) Dipotassium 4-[3-(4-{[2-({3-[(trans-4-carboxylatocyclohexyl)(ethyl)sulfamoyl]benzoyl}amino)-5-(piperidin-1-yl)benzoyl]amino}phenyl)propyl]benzoate (19a) Methyl 4-(3-{4-[(5-fluoro-2-nitrobenzoyl)amino]phenyl}propyl)benzoate Oxalyl chloride (411 mg) and DMF (1 droplet) were added to a solution of 5-fluoro-2-nitrobenzoic acid (500 mg) in DCM (3 mL) at 0° C. The reaction mixture was stirred at room temperature for 1 hour, was then concentrated, and was then diluted with DCM (3 mL). A solution of methyl 4-[3-(4-aminophenyl)propyl]benzoate (CAS registry number: 1346136-02-4, WO2011136269) (726 mg) and pyridine (255 mg) in DCM (3 mL) was added to this DCM solution. The reaction mixture was stirred at room temperature for 2.5 hours, and was then concentrated. The residue was purified by column chromatography to obtain 510 mg of the title compound (39%) in the form of a colorless oil.

(19b) Methyl 4-[3-(4-{[2-nitro-5-(piperidin-1-yl)benzoyl]amino}phenyl)propyl]benzoate 580 mg of the title compound (99%) was obtained in the form of a yellow solid from the compound (510 mg) obtained in Example (19a) and piperidine (300 mg) by a method similar to that in Example (9b) (the reaction temperature: 70° C.).

(19c) Methyl 4-[3-(4-{[2-amino-5-(piperidin-1-yl)benzoyl]amino}phenyl)propyl]benzoate 570 mg of the title compound (quantitative yield) was obtained in the form of a yellow oil from the compound (580 mg) obtained in Example (19b) by the same method as that in Example (9c).

(19d) Methyl 4-{3-[4-({2-[(3-{ethyl[trans-4-(methoxycarbonyl)cyclohexyl]sulfamoyl}benzoyl)amino]-5-(piperidin-1-yl)benzoyl}amino)phenyl]propyl}benzoate A mixture of the compound (150 mg) obtained in Example (19c), 3-{ethyl[trans-4-(methoxycarbonyl)cyclohexyl]sulfamoyl}benzoic acid (CAS registry number: 1346136-17-1, WO2011136269) (140 mg), HBTU (241 mg), DIPEA (123 mg) and DMF (3 mL) was stirred at room temperature for 16 hours, and it was then extracted with ethyl acetate (×3). The organic layer was washed with water and a saturated saline, and was then dried over sodium sulfate. The resultant was filtrated and was then concentrated. The residue was purified by column chromatography to obtain 250 mg of the title compound (96%) in the form of a light yellow oil.

(19e) Dipotassium 4-[3-(4-{[2-({3-[(trans-4-carboxylatocyclohexyl)(ethyl)sulfamoyl]benzoyl}amino)-5-(piperidin-1-yl)benzoyl]amino}phenyl)propyl]benzoate 220 mg of dicarboxylic acid was obtained from the compound (250 mg) obtained in Example (19d) by the same method as that in Example (1c). Then, 129 mg of the title compound (49%, two steps) was obtained in the form of a yellowish-white solid from the dicarboxylic acid by the same method as that in Example 4.

(Example 20) Dipotassium 4-[2-(3-{[2-({3-[(trans-4-carboxylatocyclohexyl)(ethyl)sulfamoyl]benzoyl}amino)-5-(piperidin-1-yl)benzoyl]amino}phenyl)ethyl]benzoate (20a) Methyl 4-(2-{3-[(5-fluoro-2-nitrobenzoyl)amino]phenyl}ethyl)benzoate 1.11 g of the title compound (97%) was obtained in the form of a colorless oil from 5-fluoro-2-nitrobenzoic acid (500 mg) and methyl 4-[2-(3-aminophenyl)ethyl]benzoate (CAS registry number: 872450-76-5, FR2872159) (688 mg) by the same method as that in Example (1a).

(20b) Methyl 4-[2-(3-{[2-nitro-5-(piperidin-1-yl)benzoyl]amino}phenyl)ethyl]benzoate 1.33 g of the title compound (quantitative yield) was obtained in the form of a yellow solid from the compound (1.10 g) obtained in Example (20a) and piperidine (660 mg) by a method similar to that in Example (9b) (the reaction temperature: 70° C.)

(20c) Methyl 4-[2-(3-{[2-amino-5-(piperidin-1-yl)benzoyl]amino}phenyl)ethyl]benzoate 1.00 g of the title compound (80%) was obtained in the form of a yellow solid from the compound (1.33 g) obtained in Example (20b) by the same method as that in Example (9c).

(20d) Methyl 4-{2-[3-({2-[(3-{ethyl[trans-4-(methoxycarbonyl)cyclohexyl]sulfamoyl}benzoyl)amino]-5-(piperidin-1-yl)benzoyl}amino)phenyl]ethyl}benzoate 195 mg of the title compound (74%) was obtained in the form of a yellow oil from 3-{ethyl[trans-4-(methoxycarbonyl)cyclohexyl]sulfamoyl}benzoic acid (CAS registry number: 1346136-17-1, WO2011136269) (145 mg) and the compound (150 mg) obtained in Example (20c) by the same method as that in Example (19d).

(20e) Dipotassium 4-[2-(3-{[2-({3-[(trans-4-carboxylatocyclohexyl)(ethyl)sulfamoyl]benzoyl}amino)-5-(piperidin-1-yl)benzoyl]amino}phenyl)ethyl]benzoate 160 mg of dicarboxylic acid was obtained from the compound (195 mg) obtained in Example (20d) by the same method as that in Example (1c). Then, 103 mg of the title compound (50%, two steps) was obtained in the form of a yellowish-white solid from the dicarboxylic acid (100 mg) by the same method as that in Example 4.

(Example 21) Dipotassium 4-[2-(6-{[2-({3-[(trans-4-carboxylatocyclohexyl)(ethyl)sulfamoyl]benzoyl}amino)-5-(piperidin-1-yl)benzoyl]amino}pyridin-3-yl)ethyl]benzoate (21a) 5-Fluoro-N-(5-iodopyridin-2-yl)-2-nitrobenzamide 1.46 g of the title compound (70%) was obtained in the form of a colorless oil from 5-fluoro-2-nitrobenzoic acid (1.00 g) and 5-iodopyridin-2-amine (CAS registry number: 20511-12-0) (1.18 g) by the same method as that in Example (19a).

(21b) N-(5-Iodopyridin-2-yl)-2-nitro-5-(piperidin-1-yl)benzamide 570 mg of the title compound (98%) was obtained in the form of a yellow solid from the compound (500 mg) obtained in Example (21a) and piperidine (328 mg) by a method similar to that in Example (9b) (the reaction temperature: 80° C.)

(21c) Methyl 4-[(6-{[2-nitro-5-(piperidin-1-yl)benzoyl]amino}pyridin-3-yl)ethynyl]benzoate A suspension of the compound (570 mg) obtained in Example (21b), methyl 4-ethynylbenzoate (CAS Registry Number: 3034-86-4, Angewandte Chemie, International Edition, 2009, 48, 4017-4021) (302 mg), copper(I) iodide (24 mg), bis(triphenylphosphine)palladium(II) chloride (88 mg) and triethylamine (381 mg) in THF (10 mL) was stirred at room temperature for 14 hours. The reaction mixture was filtrated and was then concentrated. The residue was purified by column chromatography to obtain 580 mg of the title compound (95%) in the form of a yellow solid.

(21d) Methyl 4-[2-(6-{[2-amino-5-(piperidin-1-yl)benzoyl]amino}pyridin-3-yl)ethyl]benzoate 310 mg of the title compound (91%) was obtained in the form of a colorless oil from the compound (360 mg) obtained in Example (21c) by the same method as that in Example (9c).

(21e) Methyl 4-{2-[6-({2-[(3-{ethyl[trans-4-(methoxycarbonyl)cyclohexyl]sulfamoyl}benzoyl)amino]-5-(piperidin-1-yl)benzoyl}amino)pyridin-3-yl]ethyl}benzoate 195 mg of the title compound (73%) was obtained in the form of a light yellow oil from 3-{ethyl[trans-4-(methoxycarbonyl)cyclohexyl]sulfamoyl}benzoic acid (CAS registry number: 1346136-17-1, WO2011136269) (145 mg) and the compound (150 mg) obtained in Example (21d) by the same method as that in Example (19d).

(21f) Dipotassium 4-[2-(6-{[2-({3-[(trans-4-carboxylatocyclohexyl)(ethyl)sulfamoyl]benzoyl}amino)-5-(piperidin-1-yl)benzoyl]amino}pyridin-3-yl)ethyl]benzoate 145 mg of dicarboxylic acid was obtained from the compound (195 mg) obtained in Example (21e) by the same method as that in Example (1c). Then, 80 mg of the title compound (69%, two steps) was obtained in the form of a yellowish-white solid from the dicarboxylic acid (81 mg) by the same method as that in Example 4.

(Example 22) Dipotassium 4-[2-(5-{[2-({3-[(trans-4-carboxylatocyclohexyl)(ethyl)sulfamoyl]benzoyl}amino)-5-(piperidin-1-yl)benzoyl]amino}pyridin-2-yl)ethyl]benzoate (22a) N-(6-Bromopyridin-3-yl)-5-fluoro-2-nitrobenzamide 1.33 g of the title compound (72%) was obtained in the form of a yellow oil from 5-fluoro-2-nitrobenzoic acid (1.00 g) and 6-bromopyridin-3-amine (CAS registry number: 13534-97-9) (923 mg) by the same method as that in Example (19a).

(22b) N-(6-Bromopyridin-3-yl)-2-nitro-5-(piperidin-1-yl)benzamide 1.17 g of the title compound (74%) was obtained in the form of a yellow solid from the compound (1.33 g) obtained in Example (22a) and piperidine (998 mg) by a method similar to that in Example (9b) (the reaction temperature: 70° C.)

(22c) Methyl 4-[(5-{[2-nitro-5-(piperidin-1-yl)benzoyl]amino}pyridin-2-yl)ethynyl]benzoate 292 mg of the title compound (81%) was obtained in the form of a brown oil from the compound (300 mg) obtained in Example (22b) and methyl 4-ethynylbenzoate (CAS Registry Number: 3034-86-4, Angewandte Chemie, International Edition, 2009, 48, 4017-4021) (142 mg) by the same method as that in Example (21c).

(22d) Methyl 4-[2-(5-{[2-amino-5-(piperidin-1-yl)benzoyl]amino}pyridin-2-yl)ethyl]benzoate 173 mg of the title compound (63%) was obtained in the form of a light yellow oil from the compound (291 mg) obtained in Example (22c) by the same method as that in Example (9c).

(22e) Methyl 4-{2-[5-({2-[(3-{ethyl[trans-4-(methoxycarbonyl)cyclohexyl]sulfamoyl}benzoyl)amino]-5-(piperidin-1-yl)benzoyl}amino)pyridin-2-yl]ethyl}benzoate 218 mg of the title compound (71%) was obtained in the form of a yellow solid from 3-{ethyl[trans-4-(methoxycarbonyl)cyclohexyl]sulfamoyl}benzoic acid (CAS registry number: 1346136-17-1, WO2011136269) (209 mg) and the compound (173 mg) obtained in Example (22d) by the same method as that in Example (1b).

(22f) Dipotassium 4-[2-(5-{[2-({3-[(trans-4-carboxylatocyclohexyl)(ethyl)sulfamoyl]benzoyl}amino)-5-(piperidin-1-yl)benzoyl]amino}pyridin-2-yl)ethyl]benzoate 138 mg of dicarboxylic acid was obtained from the compound (218 mg) obtained in Example (22e) by the same method as that in Example (1c). Then, 108 mg of the title compound (64%, two steps) was obtained in the form of a yellow solid from the dicarboxylic acid (100 mg) by the same method as that in Example 4.

(Example 23) Dipotassium 4-{2-[4-({2-[({5-[(trans-4-carboxylatocyclohexyl)(ethyl)sulfamoyl]pyridin-3-yl}carbonyl)amino]-5-(piperidin-1-yl)benzoyl}amino)phenyl]ethyl}benzoate (23a) Benzyl trans-4-(ethylamino)cyclohexanecarboxylate Sodium hydrogen carbonate (1.27 g) was added to a mixture of benzyl trans-4-aminocyclohexanecarboxylate, 4-methylbenzenesulfonate (2.78 g) (CAS Registry Number: 67299-47-2, Izvestiya Akademii Nauk SSSR, Seriya Khimicheskaya 1978, 4, 919) and ethyl acetate (20 mL)/water (10 mL) at room temperature. Ten minutes later, 2-nitrobenzenesulfonyl chloride (1.67 g) was added to the reaction mixture, and further, 15 minutes later, sodium hydrogen carbonate (0.576 g) was added to the mixture. Thirty minutes later, the reaction mixture was extracted with ethyl acetate (×2). The organic layer was dried over magnesium sulfate. The resultant was filtered and was then concentrated. The residue was diluted with a mixed solution of DCM/hexane, and it was then left overnight. The precipitated solid was collected by filtration, and was then washed with diethyl ether to obtain 2.64 g of sulfonamide. A DMF (20 mL) mixture of this sulfonamide (2.64 g), ethyl iodide (1.0 mL) and cesium carbonate (4.11 g) was stirred at room temperature for 4.5 hours, and was then concentrated. The residue was diluted with ethyl acetate, was then washed with water and a saturated saline, and was then dried over magnesium sulfate. The resultant was filtered and was then concentrated. The residue was purified by column chromatography to obtain 3.01 g of an ethylated form. A mixture of this ethylated form (3.01 g), 4-sulfanylbenzoic acid (1.95 g), potassium carbonate (2.62 g) and DMF (20 mL) was heated at 60° C. for 3 hours. Thereafter, the reaction mixture was cooled to room temperature, and was then diluted with ethyl acetate. The resultant was washed with water and a saturated saline, and was then dried over magnesium sulfate. The resultant was filtered and was then concentrated. The residue was purified by column chromatography to obtain 1.16 g of the title compound (64%, three steps) in the form of a colorless oil.

(23b) Methyl 5-[{trans-4-[(benzyloxy)carbonyl]cyclohexyl}(ethyl)sulfamoyl]pyridine-3-carboxylate Methyl 2-chloro-5-(chlorosulfonyl)pyridine-3-carboxylate (1.20 g) was added to a solution of the compound (1.16 g) obtained in Example (23a) and DIPEA (1.16 mL) in DCM (22 mL) at a temperature of 0° C. The reaction mixture was stirred at 0° C. for 4.5 hours, and was then concentrated. The residue was purified by column chromatography to obtain 680 mg of a sulfonamide form. A suspension of this sulfonamide form (680 mg) and zinc powder (180 mg) in acetic acid (7 mL) was heated at 80° C. for 3.5 hours. In order to promote the reaction to the maximum, zinc powder (180 mg) was further added to the reaction mixture. Thereafter, the reaction mixture was filtered and was then concentrated. The residue was purified by column chromatography to obtain 542 mg of the title compound (26%, two steps) in the form of a colorless oil.

(23c) Methyl 5-{[trans-4-(tert-butoxycarbonyl)cyclohexyl](ethyl)sulfamoyl}pyridine-3-carboxylate Monocarboxylic acid was obtained from the compound (358 mg) obtained in Example (23b) by the same method as that in Example (16c). A mixture of this monocarboxylic acid, di-tert-butyl dicarbonate (340 mg), 4-dimethylaminopyridine (29 mg) and t-butanol (8 mL)/THF (4 mL) was stirred at room temperature for 4 days, and was concentrated. The residue was purified by column chromatography to obtain 174 mg of the title compound (52%, two steps) in the form of a colorless oil.

(23d) Methyl 4-[2-(4-{[2-{[(5-{[trans-4-(tert-butoxycarbonyl)cyclohexyl](ethyl)sulfamoyl}pyridin-3-yl)carbonyl]amino}-5-(piperidin-1-yl)benzoyl]amino}phenyl)ethyl]benzoate A 1 N sodium hydroxide aqueous solution (0.715 mL) was added to a solution of the compound (203 mg) obtained in Example (23c) in methanol (4 mL) at a temperature of 0° C. Four hours later, the reaction mixture was converted to an acidic solution (pH 4) at 0° C. by addition of 1 N hydrochloric acid, and it was then extracted with ethyl acetate (×3). The organic layer was dried over magnesium sulfate, was then filtered, and was then concentrated. Thus, 188 mg of carboxylic acid was obtained in the form of a colorless oil. Then, 327 mg of the title compound (80%, two steps) was obtained from the carboxylic acid (187 mg) and the compound (262 mg) obtained in Example (11b) by the same method as that in Example (19d).

(23e) Dipotassium 4-{2-[4-({2-[({5-[(trans-4-carboxylatocyclohexyl)(ethyl)sulfamoyl]pyridin-3-yl}carbonyl)amino]-5-(piperidin-1-yl)benzoyl}amino)phenyl]ethyl}benzoate RHC-0626;
C55964130A1

A mixture of the compound (327 mg) obtained in Example (23d), trifluoroacetic acid (2 mL) and DCM (4 mL) was stirred at room temperature for 30 minutes, and was concentrated. The residue was purified by column chromatography to obtain 293 mg of monocarboxylic acid. Then, 243 mg of dicarboxylic acid was obtained from the monocarboxylic acid (293 mg) by the same method as that in Example (1c). Thereafter, 147 mg of the title compound (79%, three steps) was obtained in the form of a yellow solid from the dicarboxylic acid (136 mg) by the same method as that in Example 4.

(Example 24) Dipotassium 4-[2-(4-{[2-({3-[(trans-4-carboxylatocyclohexyl)(ethyl)sulfamoyl]benzoyl}amino)-5-methoxybenzoyl]amino}phenyl)ethyl]benzoate (24a) Methyl 4-(2-{4-[(5-methoxy-2-nitrobenzoyl)amino]phenyl}ethyl)benzoate Sodium hydride (63 wt %, 0.17 g) was added, little by little, to methanol (30 mL) under cooling on ice. The methyl 4-(2-{4-[(5-fluoro-2-nitrobenzoyl)amino]phenyl}ethyl)benzoate (0.570 g) obtained in Example (9a) was added to the methanol solution at room temperature. The reaction mixture was heated to 60° C.-65° C., and it was then stirred for 4.5 hours. Thereafter, the reaction mixture was cooled to room temperature, and was then concentrated. The residue was diluted with a citric acid aqueous solution, and was then extracted with ethyl acetate. The organic layer was washed with water and a saturated saline, and was then dried over sodium sulfate. The resultant was filtered and was then concentrated. The residue was purified by column chromatography to obtain 0.450 g of the title compound (77%) in the form of a light yellow solid.

(24b) Methyl 4-(2-{4-[(2-amino-5-methoxybenzoyl)amino]phenyl}ethyl)benzoate 0.370 g of the title compound (88%) was obtained in the form of a light yellow solid from the compound (0.450 g) obtained in Example (24a) by a method similar to that in Example (16c) (wherein THF was used as a solvent).

(24c) Methyl 4-{2-[4-({2-[(3-{ethyl[trans-4-(methoxycarbonyl)cyclohexyl]sulfamoyl}benzoyl)amino]-5-methoxybenzoyl}amino)phenyl]ethyl}benzoate 0.301 g of the title compound (44%) was obtained in the form of a white solid from 3-{ethyl[trans-4-(methoxycarbonyl)cyclohexyl]sulfamoyl}benzoic acid (CAS registry number: 1346136-17-1, WO2011136269) (0.450 g) and the compound (0.370 g) obtained in Example (24b) by the same method as that in Example (19a).

(24d) Dipotassium 4-[2-(4-{[2-({3-[(trans-4-carboxylatocyclohexyl)(ethyl)sulfamoyl]benzoyl}amino)-5-methoxybenzoyl]amino}phenyl)ethyl]benzoate 0.291 g of dicarboxylic acid was obtained from the compound (0.301 g) obtained in Example (24c) by a method similar to that in Example (1c) (wherein lithium hydroxide monohydrate was used). Then, 0.221 g of the title compound (quantitative yield, two steps) was obtained in the form of a light yellow solid from the dicarboxylic acid (0.195 g) by the same method as that in Example 4.

(Example 25) Dipotassium 4-[2-(4-{[2-({3-[(trans-4-carboxylatocyclohexyl)(ethyl)sulfamoyl]benzoyl}amino)-5-(2,2,2-trifluoroethoxy)benzoyl]amino}phenyl)ethyl]benzoate (25a) Methyl 4-[2-(4-{[2-amino-5-(2,2,2-trifluoroethoxy)benzoyl]amino}phenyl)ethyl]benzoate t-Butoxy potassium (0.300 g) was added to a 2,2,2-trifluoroethanol (0.3 mL)/THF (10 mL) solution at room temperature. The methyl 4-(2-{4-[(5-fluoro-2-nitrobenzoyl)amino]phenyl}ethyl)benzoate (0.500 g) obtained in Example (9a) was added to the reaction solution at room temperature. The reaction mixture was stirred at room temperature for 5 hours, and was then heated to reflux for 2 hours. Thereafter, the reaction mixture was cooled to room temperature, was then diluted with a citric acid aqueous solution and a saturated saline, and was then extracted with ethyl acetate. The organic layer was washed with water and a saturated saline, and was then dried over sodium sulfate.

The resultant was filtrated and was then concentrated. The residue was purified by column chromatography to obtain 0.710 g of an ether form in the form of a yellow solid. To a suspension of the ether form (0.710 g), iron powder (0.30 g), water (5 mL) and ammonium chloride (0.057 g) in ethanol (20 mL) were added at room temperature, and the obtained mixture was then heated to reflux for 1 hour. Thereafter, the reaction mixture was cooled to room temperature, was then filtrated with Celite, and was then concentrated. The residue was purified by column chromatography to obtain 0.370 g of the title compound (74%, two steps) in the form of a light yellow solid.

(25b) Methyl 4-{2-[4-({2-[(3-{ethyl[trans-4-(methoxycarbonyl)cyclohexyl]sulfamoyl}benzoyl)amino]-5-(2,2,2-trifluoroethoxy)benzoyl}amino)phenyl]ethyl}benzoate 0.299 g of the title compound (46%) was obtained in the form of a white solid from 3-{ethyl[trans-4-(methoxycarbonyl)cyclohexyl]sulfamoyl}benzoic acid (CAS registry number: 1346136-17-1, WO2011136269) (0.400 g) and the compound (0.370 g) obtained in Example (25a) by the same method as that in Example (19a).

(25c) Dipotassium 4-[2-(4-{[2-({3-[(trans-4-carboxylatocyclohexyl)(ethyl)sulfamoyl]benzoyl}amino)-5-(2,2,2-trifluoroethoxy)benzoyl]amino}phenyl)ethyl]benzoate 0.281 g of dicarboxylic acid was obtained from the compound (0.299 g) obtained in Example (25b) by a method similar to that in Example (1c) (wherein lithium hydroxide monohydrate was used). Then, 0.229 g of the title compound (quantitative yield, two steps) was obtained in the form of a light yellow solid from the dicarboxylic acid (0.204 g) by the same method as that in Example 4.

(Example 26) Dipotassium 4-[2-(4-{[2-({3-[(cis-4-carboxylatocyclohexyl)(ethyl)sulfamoyl]benzoyl}amino)-5-(piperidin-1-yl)benzoyl]amino}phenyl)ethyl]benzoate (26a) Benzyl 3-{[cis-4-(methoxycarbonyl)cyclohexyl]sulfamoyl}benzoate 565 mg of the title compound (63%) was obtained in the form of a colorless oil from 3-(chlorosulfonyl)benzoyl chloride (500 mg), benzyl alcohol (0.217 mL), and methyl cis-4-aminocyclohexanecarboxylate hydrochloride (CAS registry number: 61367-16-6) (486 mg) by the same method as that in Example (16a).

(26b) Benzyl 3-{ethyl[cis-4-(methoxycarbonyl)cyclohexyl]sulfamoyl}benzoate 523 mg of the title compound (88%) was obtained in the form of a colorless oil from the compound (558 mg) obtained in Example (26a) and ethyl iodide (0.117 mL) by the same method as that in Example (16b).

(26c) 3-{Ethyl[cis-4-(methoxycarbonyl)cyclohexyl]sulfamoyl}benzoic acid 382 mg of the title compound (92%) was obtained in the form of a colorless oil from the compound (518 mg) obtained in Example (26b) by the same method as that in Example (16c).

(26d) Methyl 4-{2-[4-({2-[(3-{ethyl[cis-4-(methoxycarbonyl)cyclohexyl]sulfamoyl}benzoyl)amino]-5-(piperidin-1-yl)benzoyl}amino)phenyl]ethyl}benzoate 522 mg of the title compound (97%) was obtained in the form of a yellow amorphous substance from the compound (375 mg) obtained in Example (26c) and the compound (304 mg) obtained in Example (11b) by the same method as that in Example (9d).

(26e) Dipotassium 4-[2-(4-{[2-({3-[(cis-4-carboxylatocyclohexyl)(ethyl)sulfamoyl]benzoyl}amino)-5-(piperidin-1-yl)benzoyl]amino}phenyl)ethyl]benzoate 415 mg of a dicarboxylic acid compound was obtained in the form of a yellow solid from the compound (515 mg) obtained in Example (26d) by the same method as that in Example (1c).
Then, 350 mg of the title compound (84%, two steps) was obtained in the form of a light yellow solid from the dicarboxylic acid compound (295 mg) by the same method as that in Example 4.

(Example 27) Dipotassium 4-[2-(4-{[2-({3-[(trans-4-carboxylatocyclohexyl)(cyclopropyl)sulfamoyl]benzoyl}amino)-5-(piperidin-1-yl)benzoyl]amino}phenyl)ethyl]benzoate (27a) Benzyl 3-{cyclopropyl[4-(ethoxycarbonyl)cyclohexyl]sulfamoyl}benzoate 2.06 g of the title compound (84%) was obtained in the form of a yellow oil from 3-(chlorosulfonyl)benzoyl chloride (1.54 g), benzyl alcohol (0.665 mL) and ethyl 4-(cyclopropylamino)cyclohexanecarboxylate (CAS Registry Number: 1083048-96-7, WO 2010138588) (1.07 g) by the same method as that in Example (16a).

(27b) Methyl 4-{2-[4-({2-[(3-{cyclopropyl[4-(ethoxycarbonyl)cyclohexyl]sulfamoyl}benzoyl)amino]-5-(piperidin-1-yl)benzoyl}amino)phenyl]ethyl}benzoate Carboxylic acid was obtained from the compound (730 mg) obtained in Example (27a) by the same method as that in Example (16c). Then, 1.19 g of the title compound (95%, two steps) was obtained in the form of a yellow amorphous substance from the carboxylic acid and the compound (1.24 g) obtained in Example (11b) by the same method as that in Example (16d).

(27c) Dipotassium 4-[2-(4-{[2-({3-[(trans-4-carboxylatocyclohexyl)(cyclopropyl)sulfamoyl]benzoyl}amino)-5-(piperidin-1-yl)benzoyl]amino}phenyl)ethyl]benzoate 756 mg of a dicarboxylic acid compound was obtained in the form of a yellow solid from the compound (1.19 g) obtained in Example (27b) by the same method as that in Example (1c).
Then, 411 mg of the title compound (44%, two steps) was obtained in the form of a yellow solid from the dicarboxylic acid compound (622 mg) by the same method as that in Example 4.

(Example 28) Disodium 4-[2-(4-{[2-({3-[(trans-4-carboxylatocyclohexyl)(ethyl)sulfamoyl]benzoyl}amino)-5-(piperidin-1-yl)benzoyl]amino}phenyl)ethyl]benzoate 1 N sodium hydroxide (159 μL) was added to a suspension of the compound (62 mg) obtained in Example 11 in methanol (3 mL), and the reaction mixture was then concentrated under reduced pressure. The concentrate was dissolved again in methanol (1 mL), and ethyl acetate (5 mL) was then added to the solution, followed by vacuum concentration, to obtain 64 mg of the title compound (98%) in the form of a light yellow solid.

(Example 29) Disodium 4-[2-(4-{[2-({3-[(trans-4-carboxylatocyclohexyl)(ethyl)sulfamoyl]benzoyl}amino)-5-(diethylamino)benzoyl]amino}phenyl)ethyl]benzoate 61 mg of the title compound (96%) was obtained in the form of a light yellow solid from the compound (60 mg) obtained in Example 13 by the same method as that in Example 28.

(Example 30) Disodium 4-[2-(4-{[2-({3-[(trans-4-carboxylatocyclohexyl)(ethyl)sulfamoyl]benzoyl}amino)-5-(cyclopropylmethoxy)benzoyl]amino}phenyl)ethyl]benzoate 654 mg of dicarboxylic acid (95%) was obtained in the form of a yellow solid from the compound (710 mg) obtained in Example (15e) by the same method as that in Example (1c).

Then, 27 mg of the title compound (quantitative yield) was obtained in the form of a light yellow solid from the dicarboxylic acid (25 mg) by the same method as that in Example 28.

(Example 31) Disodium 4-[2-(4-{[2-({3-[(cis-4-carboxylatocyclohexyl)(ethyl)sulfamoyl]benzoyl}amino)-5-(piperidin-1-yl)benzoyl]amino}phenyl)ethyl]benzoate 415 mg of a dicarboxylic acid compound was obtained in the form of a yellow solid from the compound (515 mg) obtained in Example (26d) by the same method as that in Example (1c).

Then, 26 mg of the title compound (99%) was obtained in the form of a yellow solid from the dicarboxylic acid (25 mg) by the same method as that in Example 28.

(Example 32) Disodium 4-[2-(4-{[2-({3-[(trans-4-carboxylatocyclohexyl)(cyclopropyl)sulfamoyl]benzoyl}amino)-5-(piperidin-1-yl)benzoyl]amino}phenyl)ethyl]benzoate 756 mg of a dicarboxylic acid compound was obtained in the form of a yellow solid from the compound (1.19 g) obtained in Example (27b) by the same method as that in Example (1c).

Then, 28 mg of the title compound (quantitative yield) was obtained in the form of a yellow solid from the dicarboxylic acid (25 mg) by the same method as that in Example 28.

The structural formulae of the compounds produced in the Examples and the physicochemical data thereof are shown below.

Ex No. indicates the number of each example.

TABLE 2

| Ex No. | Structural formula |
|---|---|
| 1 | 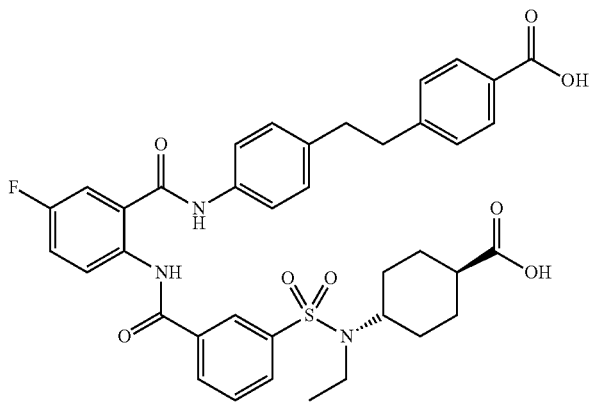 |

TABLE 2-continued
| Ex No. | Structural formula |
|---|---|
| 2 | 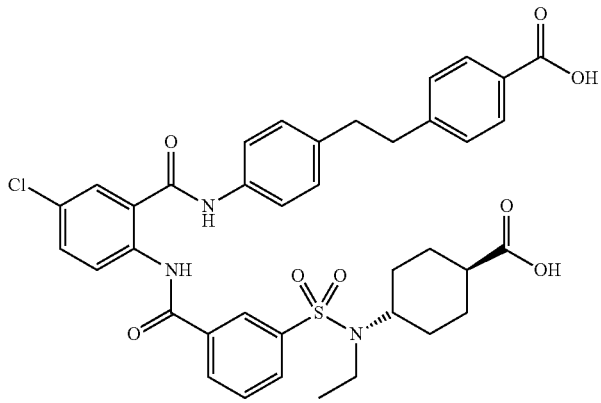 |
| 3 | 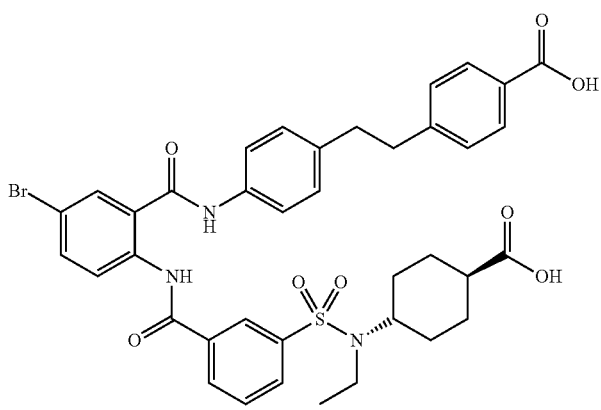 |
| 4 | 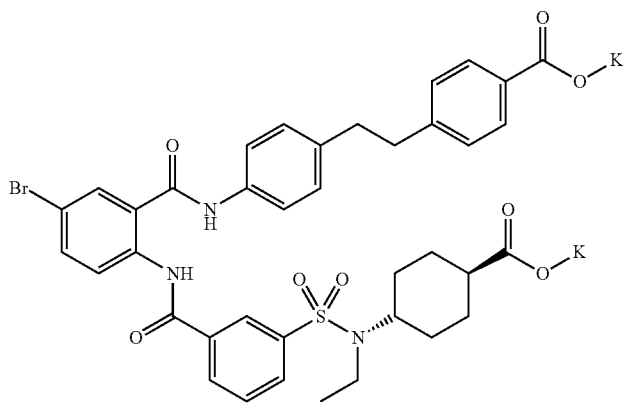 |

TABLE 2-continued
| Ex No. | Structural formula |
|---|---|
| 5 | 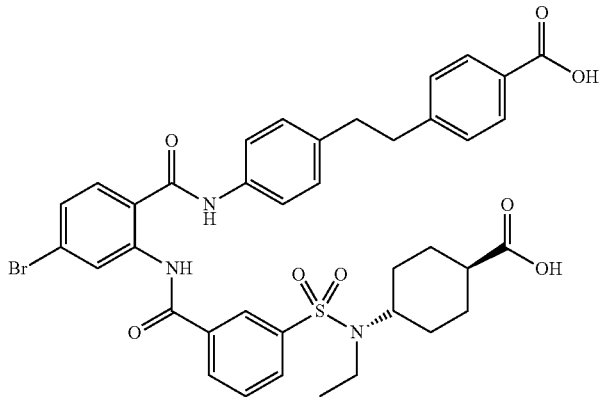 |
| 6 | 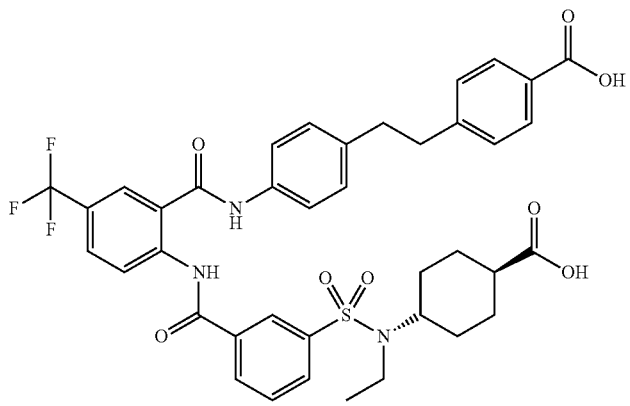 |
| 7 | 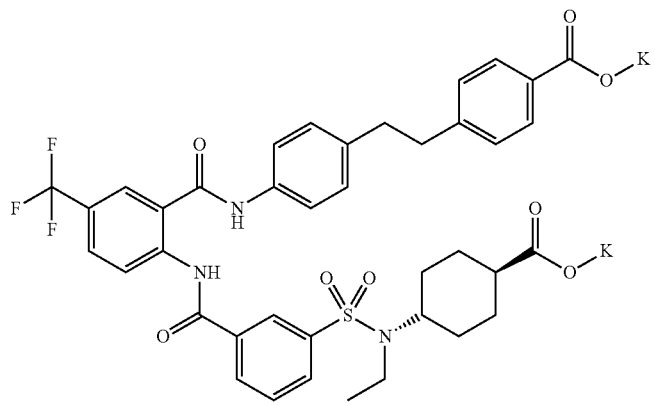 |

TABLE 2-continued
| Ex No. | Structural formula |
|---|---|
| 8 | 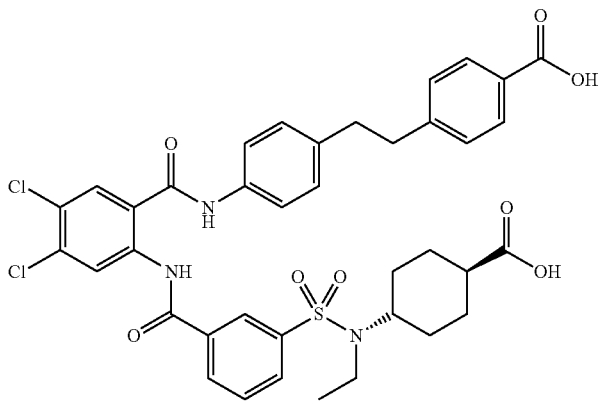 |
| 9 | 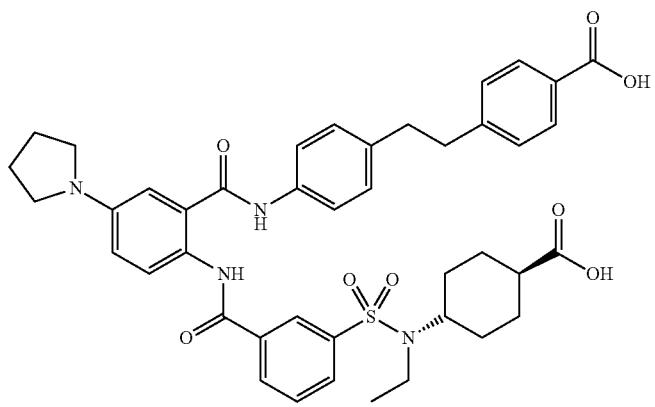 |
| 10 | 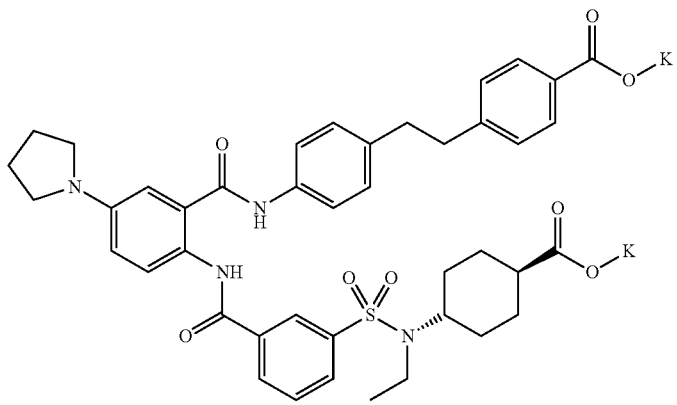 |

TABLE 3
| Ex No. | Structural formula |
|---|---|
| 11 | 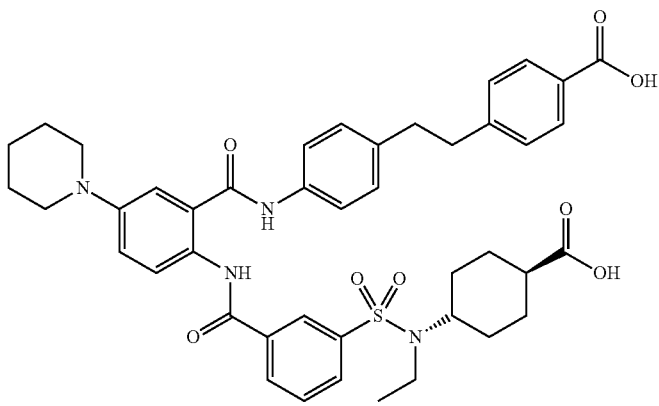 |
| 12 | 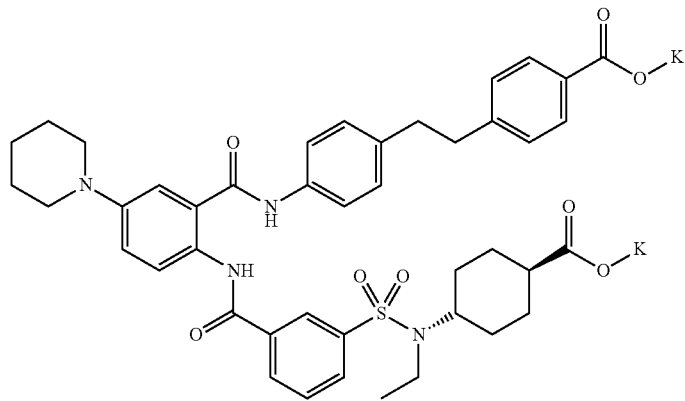 |
| 13 | 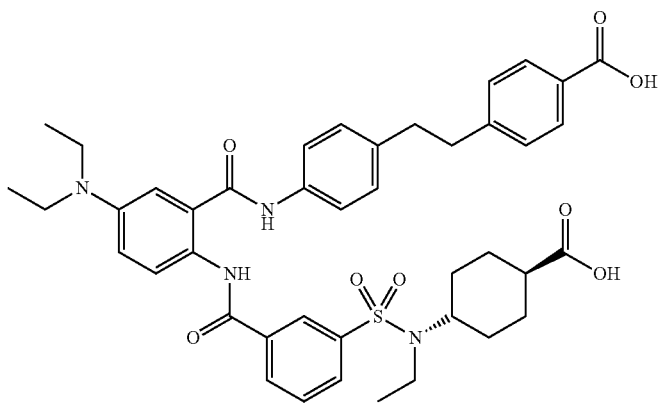 |

TABLE 3-continued

| Ex No. | Structural formula |
|---|---|
| 14 | |
| 15 | |
| 16 | |

TABLE 3-continued
| Ex No. | Structural formula |
|---|---|
| 17 | 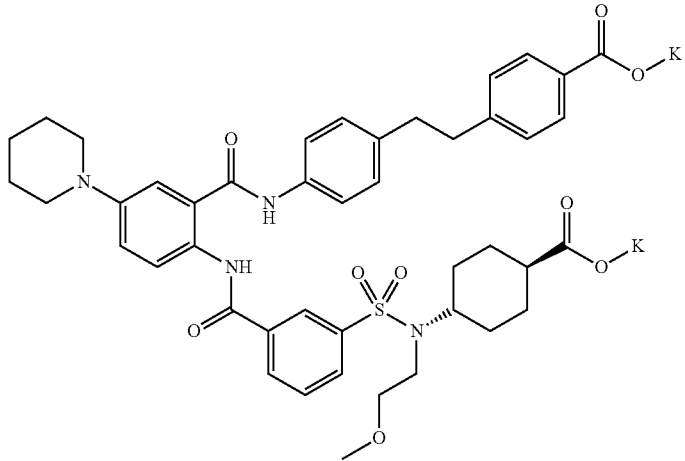 |
| 18 | 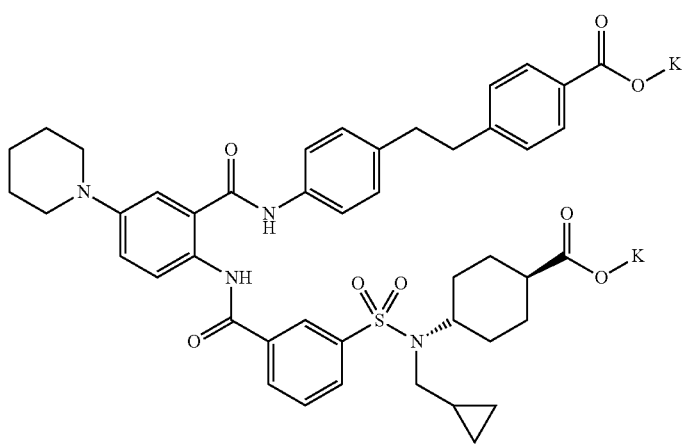 |
| 19 | 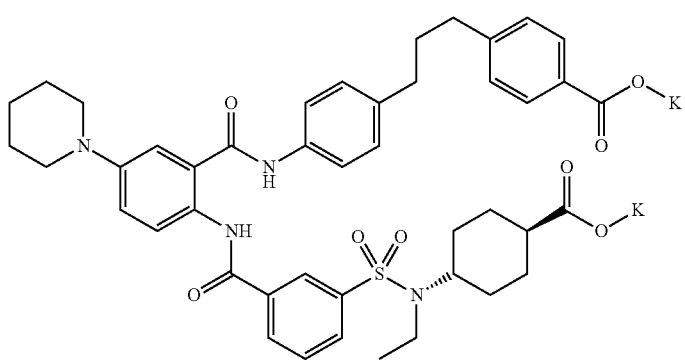 |

TABLE 3-continued
| Ex No. | Structural formula |
|---|---|
| 20 | 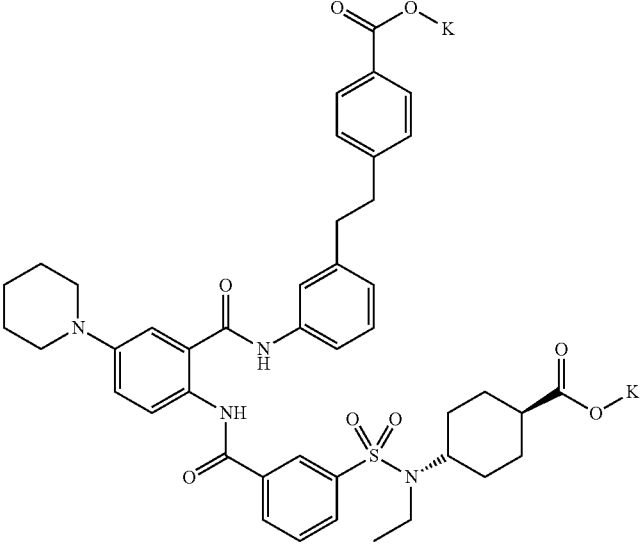 |
TABLE 4
| Ex No. | Structural formula |
|---|---|
| 21 | 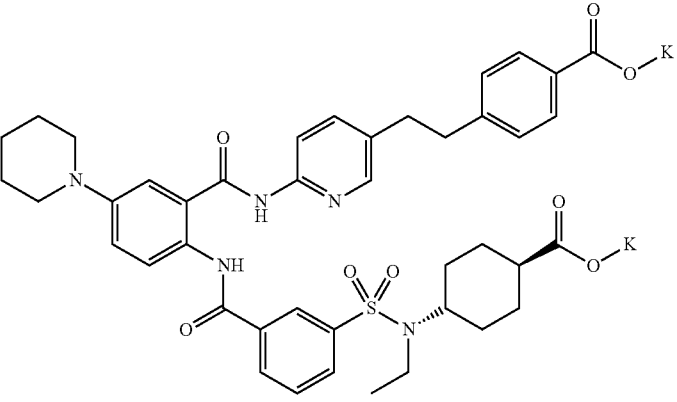 |
| 22 | 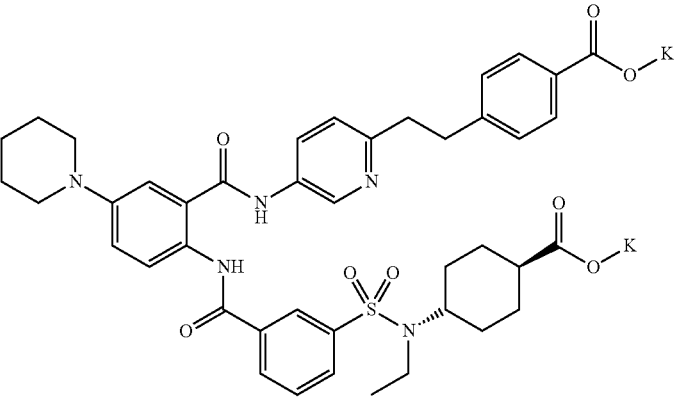 |

TABLE 4-continued
| Ex No. | Structural formula |
|---|---|
| 23 | 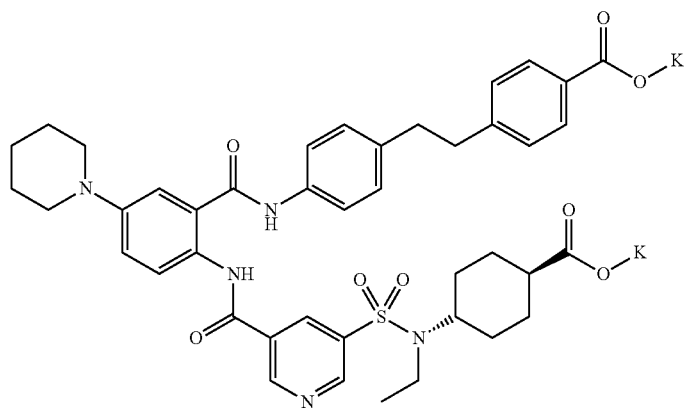 |
| 24 | 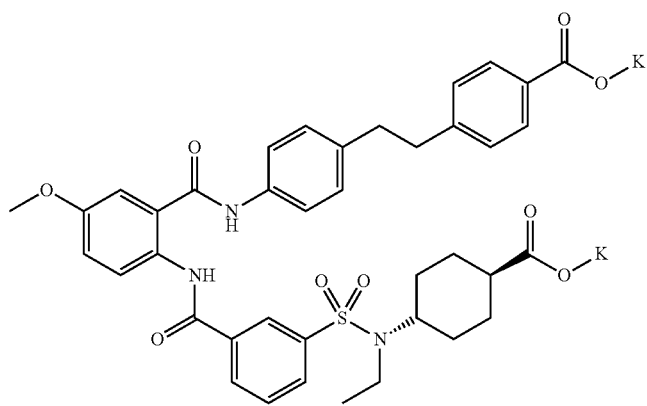 |
| 25 | 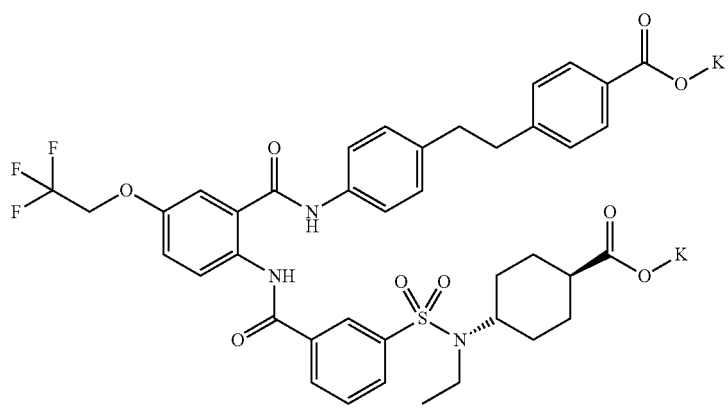 |

TABLE 4-continued

| Ex No. | Structural formula |
|---|---|
| 26 | (structure) |
| 27 | (structure) |

TABLE 5

| Ex No. | Structural formula |
|---|---|
| 28 | (structure) |

TABLE 5-continued
| Ex No. | Structural formula |
|---|---|
| 29 | 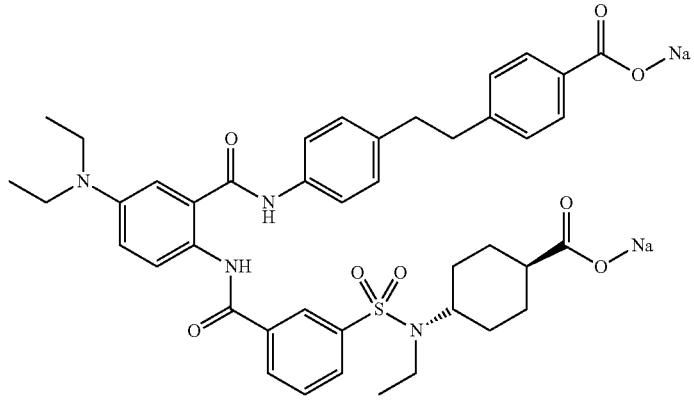 |
| 30 | 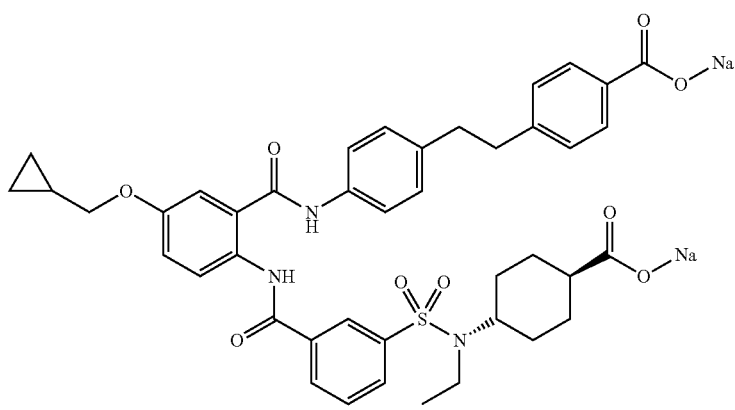 |
| 31 | 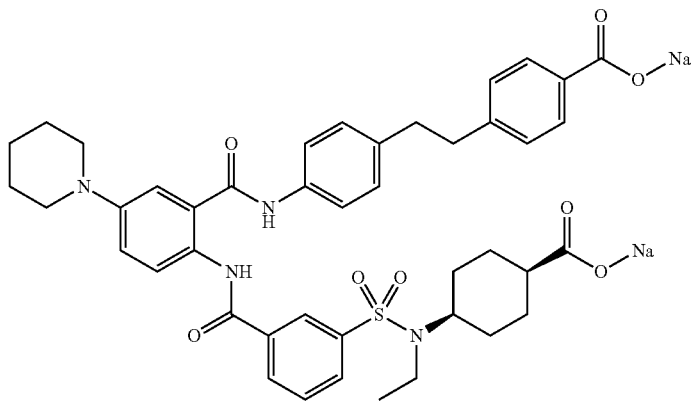 |

TABLE 5-continued

| Ex No. | Structural formula |
|---|---|
| 32 | |

TABLE 6

| Ex No. | Physicochemical data |
|---|---|
| 1 (1a) | $^1$H NMR (400 MHz, CDCl$_3$): δ (ppm) = 8.00-7.92 (2H, m), 7.70 (1H, s), 7.49-7.43 (2H, m), 7.22 (2H, d, J = 8.2 Hz), 7.19 (1H, dd, J = 9.0 and 2.7 Hz), 7.14 (2H, d, J = 8.2 Hz), 7.02 (1H, ddd, J = 9.0, 7.8 and 3.1 Hz), 6.69 (1H, dd, J = 9.0 and 4.7 Hz), 5.25 (brs, 2H), 3.91 (3H, s), 3.02-2.89 (4H, m). |
| 1 (1b) | $^1$H NMR (500 MHz, CDCl$_3$): δ (ppm) = 11.84 (1H, s), 8.69 (1H, dd, J = 9.3 and 4.9 Hz), 8.49-8.44 (1H, m), 8.22 (1H, brs), 8.14 (1H, dd, J = 7.8 and 1.0 Hz), 8.02 (1H, dd, J = 7.8 and 1.0 Hz), 7.95 (2H, d, J = 8.3 Hz), 7.64 (1H, t, J = 7.8 Hz), 7.55 (2H, d, J = 8.3 Hz), 7.34 (1H, dd, J = 8.5 and 2.7 Hz), 7.25-7.12 (5H, m), 3.91 (3H, s), 3.72-3.64 (1H, m), 3.63 (3H, s), 3.30 (2H, q, J = 7.3 Hz), 3.06-2.86 (4H, m), 2.21-2.08 (1H, m), 2.02-1.93 (2H, m), 1.78-1.65 (2H, m), 1.54-1.37 (4H, m), 1.26 (3H, t, J = 7.1 Hz). |
| 1 (1c) | $^1$H NMR (400 MHz, DMSO-d$_6$): δ (ppm) = 11.54 (1H, s), 10.58 (1H, s), 8.31 (1H, s), 8.27 (1H, dd, J = 9.2 and 5.3 Hz), 8.14 (1H, d, J = 7.8 Hz), 8.07 (1H, d, J = 7.8 Hz), 7.85 (2H, d, J = 7.8 Hz), 7.81-7.72 (2H, m), 7.60 (2H, d, J = 8.6 Hz), 7.50 (1H, td, J = 8.6 and 2.7 Hz), 7.34 (2H, d, J = 8.2 Hz), 7.19 (2H, d, J = 8.2 Hz), 3.68-3.53 (1H, m), 3.22 (2H, q, J = 6.8 Hz), 3.00-2.81 (4H, m), 2.15-2.03 (1H, m), 1.84 (2H, brd, J = 12.5 Hz), 1.54-1.25 (6H, m), 1.14 (3H, t, J = 7.0 Hz). MS (ESI) m/z: 716 (M + H)$^+$. |
| 2 (2a) | $^1$H NMR (400 MHz, CDCl$_3$): δ (ppm) = 7.95 (2H, d, J = 8.6 Hz), 7.63 (1H, s), 7.49-7.40 (3H, m), 7.24-7.19 (3H, m), 7.15 (2H, d, J = 8.6 Hz), 6.67 (1H, d, J = 9.0 Hz), 5.49 (2H, brs), 3.91 (3H, s), 3.02-2.87 (4H, m). |
| 2 (2b) | $^1$H NMR (500 MHz, CDCl$_3$): δ (ppm) = 11.98 (1H, s), 8.76 (1H, d, J = 9.0 Hz), 8.47 (1H, s), 8.15 (1H, d, J = 7.8 Hz), 8.06-7.98 (2H, m), 7.95 (2H, d, J = 8.3 Hz), 7.68-7.61 (2H, m), 7.55-7.50 (3H, m), 7.23 (2H, d, J = 8.3 Hz), 7.19 (2H, d, J = 8.3 Hz), 3.91 (3H, s), 3.73-3.61 (1H, m), 3.63 (3H, s), 3.30 (2H, q, J = 6.9 Hz), 3.02-2.92 (4H, m), 2.20-2.09 (1H, m), 2.02-1.93 (2H, m), 1.75-1.68 (2H, m), 1.51-1.42 (4H, m), 1.26 (3H, t, J = 7.1 Hz). |
| 2 (2c) | $^1$H NMR (400 MHz, DMSO-d$_6$): δ (ppm) = 11.72 (1H, s), 10.56 (1H, s), 8.36 (1H, d, J = 8.6 Hz), 8.31 (1H, t, J = 1.6 Hz), 8.14 (1H, d, J = 8.2 Hz), 8.08 (1H, d, J = 8.6 Hz), 7.97 (1H, d, J = 2.7 Hz), 7.85 (2H, d, J = 8.2 Hz), 7.79 (1H, t, J = 7.8 Hz), 7.69 (1H, dd, J = 8.8 and 2.5 Hz), 7.61 (2H, d, J = 8.2 Hz), 7.34 (2H, d, J = 8.2 Hz), 7.20 (2H, d, J = 8.6 Hz), 3.67-3.55 (1H, m), 3.22 (2H, q, J = 6.9 Hz), 3.00-2.85 (4H, m), 2.08 (1H, tt, J = 12.1 and 3.2 Hz), 1.84 (2H, brd, J = 11.4 Hz), 1.55-1.41 (4H, m), 1.39-1.25 (2H, m), 1.14 (3H, t, J = 7.0 Hz). MS (ESI) m/z: 733 (M + H)$^+$. |
| 3 (3a) | $^1$H NMR (400 MHz, CDCl$_3$): δ (ppm) = 7.95 (2H, d, J = 8.2 Hz), 7.61 (1H, s), 7.56 (1H, d, J = 2.4 Hz), 7.46 (2H, d, J = 8.2 Hz), 7.33 (1H, dd, J = 8.6 and 2.4 Hz), 7.22 (2H, d, J = 8.2 Hz), 7.14 (2H, d, J = 8.6 Hz), 6.62 (1H, d, J = 8.6 Hz), 5.51 (2H, brs), 3.91 (3H, s), 3.00-2.90 (4H, m). |
| 3 (3b) | $^1$H NMR (400 MHz, CDCl$_3$): δ (ppm) = 11.99 (1H, s), 8.74 (1H, d, J = 9.0 Hz), 8.46 (1H, t, J = 1.6 Hz), 8.19-8.11 (1H, m), 8.05-8.00 (1H, m), 7.95 (2H, d, J = 8.6 Hz), 7.91 (1H, s), 7.80 (1H, d, J = 2.4 Hz), 7.68 (1H, dd, J = 8.8 and 2.2 Hz), 7.64 (1H, t, J = 7.8 Hz), 7.50 (2H, d, J = 8.2 Hz), 7.23 (2H, d, J = 8.2 Hz), 7.18 (2H, d, J = 8.6 Hz), 3.91 (3H, s), 3.72-3.61 (1H, m), 3.63 (3H, s), 3.30 (2H, q, J = 7.0 Hz), 3.01-2.93 (4H, m), 2.19-2.09 (1H, m), 2.02-1.93 (2H, m), 1.76-1.66 (2H, m), 1.51-1.40 (4H, m), 1.25 (3H, t, J = 7.0 Hz). |

TABLE 6-continued

| Ex No. | Physicochemical data |
|---|---|
| 3 (3c) | $^1$H NMR (400 MHz, DMSO-d$_6$): δ (ppm) = 11.73 (1H, s), 10.56 (1H, s), 8.34-8.26 (2H, m), 8.14 (1H, d, J = 8.2 Hz), 8.10-8.04 (2H, m), 7.88-7.75 (4H, m), 7.60 (2H, d, J = 8.2 Hz), 7.34 (2H, d, J = 8.6 Hz), 7.20 (2H, d, J = 8.6 Hz), 3.66-3.55 (1H, m), 3.22 (2H, q, J = 6.9 Hz), 2.99-2.85 (4H, m), 2.14-2.02 (1H, m), 1.84 (2H, brd, J = 11.7 Hz), 1.53-1.41 (4H, m), 1.39-1.25 (2H, m), 1.14 (3H, t, J = 7.0 Hz). MS (ESI) m/z: 776 (M + H)$^+$. |

TABLE 7

| Ex No. | Physicochemical data |
|---|---|
| 4 | $^1$H NMR (400 MHz, CD$_3$OD): δ (ppm) = 8.58 (1H, d, J = 9.0 Hz), 8.43 (1H, t, J = 1.6 Hz), 8.19 (1H, dq, J = 7.8 and 0.9 Hz), 8.10 (1H, d, J = 2.4 Hz), 8.08 (1H, dq, J = 7.8 and 0.9 Hz), 7.87-7.83 (2H, m), 7.78-7.72 (2H, m), 7.59 (2H, d, J = 8.2 Hz), 7.23-7.15 (4H, m), 3.70-3.60 (1H, m), 3.33-3.27 (2H, m), 2.99-2.89 (4H, m), 2.02-1.86 (3H, m), 1.62-1.34 (6H, m), 1.23 (3H, t, J = 7.0 Hz). MS (ESI) m/z: 776 (M + H)$^+$. |
| 5 (5a) | $^1$H NMR (400 MHz, CDCl$_3$): δ (ppm) = 7.94 (2H, d, J = 8.6 Hz), 7.62 (1H, s), 7.44 (2H, d, J = 8.6 Hz), 7.30 (1H, d, J = 8.6 Hz), 7.22 (2H, d, J = 8.2 Hz), 7.14 (2H, d, J = 8.2 Hz), 6.89 (1H, d, J = 2.0 Hz), 6.82 (1H, dd, J = 8.2 and 2.0 Hz), 5.61 (2H, brs), 3.90 (3H, s), 3, 01-2.89 (4H, m). |
| 5 (5b) | $^1$H NMR (400 MHz, CDCl$_3$): δ (ppm) = 12.17 (1H, s), 9.00 (1H, d, J = 2.0 Hz), 8.44 (1H, t, J = 1.6 Hz), 8.23 (1H, s), 8.13 (1H, dd, J = 8.2 and 1.2 Hz), 8.02 (1H, dq, J = 7.8 and 0.9 Hz), 7.95 (2H, d, J = 8.2 Hz), 7.65 (1H, t, J = 8.0 Hz), 7.54 (2H, d, J = 8.6 Hz), 7.50 (1H, d, J = 8.6 Hz), 7.24-7.20 (3H, m), 7.17 (2H, d, J = 8.6 Hz), 3.90 (3H, s), 3.71-3.59 (1H, m), 3.62 (3H, s), 3.29 (2H, q, J = 7.3 Hz), 3.02-2.91 (4H, m), 2.18-2.08 (1H, m), 2.02-1.94 (2H, m), 1.75-1.65 (2H, m), 1.53-1.38 (4H, m), 1.25 (3H, t, J = 7.0 Hz). |
| 5 (5c) | $^1$H NMR (400 MHz, DMSO-d$_6$): δ (ppm) = 12.00 (1H, s), 10.55 (1H, s), 8.67 (1H, d, J = 2.0 Hz), 8.31 (1H, t, J = 1.6 Hz), 8.14 (1H, dd, J = 8.0 and 1.4 Hz), 8.09 (1H, d, J = 7.8 Hz), 7.93-7.76 (4H, m), 7.61 (2H, d, J = 8.6 Hz), 7.55 (1H, dd, J = 8.6 and 2.0 Hz), 7.34 (2H, d, J = 8.6 Hz), 7.20 (2H, d, J = 8.6 Hz), 3.61 (1H, tt, J = 10.1 and 5.3 Hz), 3.23 (2H, q, J = 7.0 Hz), 3.00-2.85 (4H, m), 2.09 (1H, tt, J = 11.9 and 3.3 Hz), 1.85 (2H, brd, J = 11.4 Hz), 1.55-1.41 (4H, m), 1.32 (2H, qd, J = 12.2 and 4.5 Hz), 1.14 (3H, t, J = 7.0 Hz). MS (ESI) m/z: 777 (M + H)+. |
| 6 (6a) | $^1$H NMR (400 MHz, CDCl$_3$): δ (ppm) = 7.95 (2H, d, J = 8.2 Hz), 7.70 (1H, s), 7.66 (1H, s), 7.50-7.44 (3H, m), 7.22 (2H, d, J = 8.2 Hz), 7.15 (2H, d, J = 8.2 Hz), 6.75 (1H, d, J = 8.6 Hz), 5.89 (2H, brs), 3.91 (3H, s), 3.02-2.89 (4H, m). |
| 6 (6b) | $^1$H NMR (400 MHz, CDCl$_3$): δ (ppm) = 12.25 (1H, s), 8.99 (1H, d, J = 9.0 Hz), 8.48 (1H, t, J = 1.8 Hz), 8.17 (1H, td, J = 8.2 and 1.4H), 8.04 (1H, td, J = 7.8 and 1.4 Hz), 8.00-7.89 (4H, m), 7.84 (1H, dd, J = 9.0 and 2.0 Hz), 7.66 (1H, t, J = 7.8 Hz), 7.52 (2H, d, J = 8.2 Hz), 7.23 (2H, d, J = 8.2 Hz), 7.19 (2H, d, J = 8.2 Hz), 3.91 (3H, s), 3.72-3.60 (1H, m), 3.63 (3H, s), 3.30 (2H, q, J = 7.0 Hz), 3.03-2.92 (4H, m), 2.20-2.08 (1H, m), 2.02-1.94 (2H, m), 1.77-1.67 (2H, m), 1.51-1.37 (4H, m), 1.25 (3H, t, J = 7.0 Hz). |
| 6 (6c) | $^1$H NMR (400 MHz, DMSO-d$_6$): δ (ppm) = 12.03 (1H, s), 10.69 (1H, s), 8.60 (1H, d, J = 8.6 Hz), 8.33 (1H, t, J = 1.6 Hz), 8.25 (1H, s), 8.16 (1H, d, J = 8.2 Hz), 8.10 (1H, d, J = 8.2 Hz), 8.00 (1H, dd, J = 8.8 and 1.8 Hz), 7.85 (2H, d, J = 8.2 Hz), 7.81 (1H, t, J = 7.8 Hz), 7.60 (2H, d, J = 8.6 Hz), 7.34 (2H, d, J = 8.2 Hz), 7.22 (2H, d, J = 8.6 Hz), 3.67-3.55 (1H, m), 3.23 (2H, q, J = 6.9 Hz), 3.00-2.86 (4H, m), 2.14-2.02 (1H, m), 1.84 (2H, brd, J = 11.4 Hz), 1.55-1.40 (4H, m), 1.39-1.26 (2H, m), 1.14 (3H, t, J = 7.0 Hz). MS (ESI) m/z: 766 (M + H)$^+$. |
| 7 | $^1$H NMR (400 MHz, CD$_3$OD): δ (ppm) = 8.88 (1H, d, J = 9.0 Hz), 8.46 (1H, t, J = 1.8 Hz), 8.26 (1H, s), 8.22 (1H, dq, J = 7.8 and 0.9 Hz), 8.09 (1H, dq, J = 7.9 and 1.0 Hz), 7.89 (1H, dd, J = 8.8 and 1.8 Hz), 7.85 (2H, d, J = 8.2 Hz), 7.77 (1H, t, J = 7.8 Hz), 7.60 (2H, d, J = 8.6 Hz), 7.21 (2H, d, J = 8.6 Hz), 7.18 (2H, d, J = 8.6 Hz), 3.72-3.59 (1H, m), 3.35-3.23 (2H, m), 2.94 (4H, s), 2.02-1.84 (3H, m), 1.63-1.33 (6H, m), 1.23 (3H, t, J = 7.0 Hz). MS (ESI) m/z: 766 (M + H)+. |

TABLE 8

| Ex No. | Physicochemical data |
|---|---|
| 8 (8a) | $^1$H NMR (400 MHz, CDCl$_3$): δ (ppm) = 7.94 (2H, d, J = 8.6 Hz), 7.58 (1H, s), 7.52 (1H, s), 7.44 (2H, d, J = 8.2 Hz), 7.22 (2H, d, J = 8.2 Hz), |

TABLE 8-continued

| Ex No. | Physicochemical data |
|---|---|
| | 7.14 (2H, d, J = 8.6 Hz), 6.83 (2H, s), 5.57 (2H, s), 3.91 (3H, s), 3.01-2.89 (4H, m). |
| 8 (8b) | $^1$H NMR (400 MHz, CDCl$_3$): δ (ppm) = 12.10 (1H, s), 9.07 (1H, s), 8.46 (1H, t, J = 1.6 Hz), 8.14 (1H, dt, J = 7.8 and 1.5 Hz), 8.04 (1H, dq, J = 8.0 and 1.0 Hz), 7.95 (2H, d, J = 8.2 Hz), 7.90 (1H, s), 7.76 (1H, s), 7.65 (1H, t, J = 7.8 Hz), 7.50 (2H, d, J = 8.6 Hz), 7.22 (2H, d, J = 7.8 Hz), 7.18 (2H, d, J = 8.2 Hz), 3.91 (3H, s), 3.70-3.61 (1H, m), 3.63 (3H, s), 3.29 (2H, q, J = 6.9 Hz), 3.01-2.94 (4H, m), 2.16-2.09 (1H, m), 2.01-1.93 (2H, m), 1.75-1.66 (2H, m), 1.50-1.39 (4H, m), 1.25 (3H, t, J = 7.0 Hz). |
| 8 (8c) | $^1$H NMR (400 MHz, DMSO-d$_6$): δ (ppm) = 11.85 (1H, s), 10.58 (1H, s), 8.62 (1H, s), 8.26 (1H, t, J = 2.0 Hz), 8.17 (1H, s), 8.10 (1H, d, J = 7.8 Hz), 8.06 (1H, d, J = 8.2 Hz), 7.81 (2H, d, J = 8.2 Hz), 7.77 (1H, t, J = 8.0 Hz), 7.56 (2H, d, J = 8.6 Hz), 7.30 (2H, d, J = 8.2 Hz), 7.17 (2H, d, J = 8.6 Hz), 3.62-3.50 (1H, m), 3.19 (2H, q, J = 6.8 Hz), 2.95-2.82 (4H, m), 2.11-1.99 (1H, m), 1.81 (2H, d, J = 10.9 Hz), 1.49-1.36 (4H, m), 1.36-1.18 (2H, m), 1.10 (3H, t, J = 6.8 Hz). |
| 9 (9a) | $^1$H NMR (400 MHz, CDCl$_3$) δ: 8.22 (1H, dd, J = 9.0, 4.7 Hz), 7.95 (2H, d, J = 8.2 Hz), 7.48 (2H, d, J = 8.6 Hz), 7.39 (1H, s), 7.35-7.28 (2H, m), 7.23 (2H, d, J = 8.2 Hz), 7.16 (2H, d, J = 8.2 Hz), 3.91 (3H, s), 2.99-2.94 (4H, m). |
| 9 (9b) | $^1$H NMR (400 MHz, CDCl$_3$) δ: 8.12 (1H, d, J = 9.4 Hz), 7.95 (2H, d, J = 8.2 Hz), 7.51 (2H, d, J = 8.6 Hz), 7.33 (1H, s), 7.23 (2H, d, J = 8.2 Hz), 7.13 (2H, d, J = 8.2 Hz), 6.53-6.50 (2H, m), 3.92 (3H, s), 3.42 (4H, t, J = 6.5 Hz), 2.97-2.93 (4H, m), 2.10-2.07 (4H, m). |
| 9 (9c) | $^1$H NMR (400 MHz, CDCl$_3$) δ: 8.46 (1H, s), 7.94 (2H, d, J = 8.2 Hz), 7.50 (2H, d, J = 8.6 Hz), 7.22 (2H, d, J = 8.2 Hz), 7.13 (2H, d, J = 8.2 Hz), 6.83-6.62 (3H, m), 4.49 (2H, br s), 3.91 (3H, s), 3.26 (4H, br m), 2.98-2.92 (4H, m), 2.05-1.97 (4H, m). |
| 9 (9d) | $^1$H NMR (400 MHz, CDCl$_3$) δ: 11.33 (1H, s), 8.47 (1H, d, J = 9.0 Hz), 8.43 (1H, t, J = 1.8 Hz), 8.19 (1H, s), 8.11 (1H, dd, J = 8.2, 1.2 Hz), 7.98-7.96 (3H, m), 7.60 (1H, t, J = 7.8 Hz), 7.56 (2H, d, J = 8.6 Hz), 7.24 (2H, d, J = 8.2 Hz), 7.18 (2H, d, J = 8.6 Hz), 6.70 (1H, dd, J = 9.0, 2.7 Hz), 6.65 (1H, d, J = 2.3 Hz), 3.91 (3H, s), 3.70-3.66 (1H, m), 3.63 (3H, s), 3.30 (2H, q, J = 7.2 Hz), 3.25 (4H, t, J = 6.1 Hz), 3.01-2.93 (4H, m), 2.15-2.10 (1H, m), 1.96 (6H, t, J = 6.6 Hz), 1.73 (2H, brd, J = 9.0 Hz), 1.46 (4H, dd, J = 21.1, 11.7 Hz), 1.26 (3H, t, J = 7.0 Hz). |
| 9 (9e) | $^1$H NMR (400 MHz, DMSO-D$_6$) δ: 11.14 (1H, s), 10.33 (1H, s), 8.27 (1H, s), 8.11 (1H, d, J = 7.8 Hz), 8.01 (2H, t, J = 8.8 Hz), 7.84 (2H, d, J = 8.2 Hz), 7.74 (1H, t, J = 7.8 Hz), 7.58 (2H, d, J = 8.2 Hz), 7.33 (2H, d, J = 8.2 Hz), 7.17 (2H, d, J = 8.6 Hz), 6.92 (1H, d, J = 2.3 Hz), 6.77 (1H, dd, J = 9.0, 2.7 Hz), 3.64-3.56 (1H, m), 3.33-3.26 (4H, m), 3.21 (2H, q, J = 7.3 Hz), 2.96-2.86 (4H, m), 2.11-2.06 (1H, m), 1.99 (4H, t, J = 6.5 Hz), 1.84 (2H, d, J = 12.1 Hz), 1.50-1.40 (4H, m), 1.37-1.26 (2H, m), 1.13 (3H, t, J = 7.0 Hz). MS (ESI) m/z: 767 (M + H)$^+$. |
| 10 | $^1$H NMR (400 MHz, CD$_3$OD) δ: 8.39 (1H, t, J = 1.6 Hz), 8.18 (1H, d, J = 8.6 Hz), 8.13 (1H, dd, J = 7.6, 1.8 Hz), 8.04-8.02 (1H, m), 7.84 (2H, d, J = 8.2 Hz), 7.71 (1H, t, J = 7.8 Hz), 7.55 (2H, d, J = 8.6 Hz), 7.17 (4H, dd, J = 8.2, 2.7 Hz), 6.99 (1H, d, J = 2.3 Hz), 6.80 (1H, dd, J = 9.0, 2.7 Hz), 3.67-3.63 (1H, m), 3.40-3.37 (4H, m), 3.30-3.29 (2H, m), 2.93 (4H, t, J = 4.9 Hz), 2.09-2.04 (2H, m), 1.99-1.86 (3H, m), 1.61-1.54 (2H, m), 1.52-1.36 (4H, m), 1.22 (3H, t, J = 6.8 Hz). MS (ESI) m/z: 767 (M + H)$^+$. |

TABLE 9

| Ex No. | Physicochemical data |
|---|---|
| 11 (a) | $^1$H-NMR (400 MHz, CDCl$_3$) δ: 8.09 (1H, d, J = 9.0 Hz), 7.95 (2H, d, J = 8.2 Hz), 7.50 (2H, d, J = 8.6 Hz), 7.31 (1H, s), 7.22 (2H, d, J = 8.2 Hz), 7.13 (2H, d, J = 8.2 Hz), 6.84-6.78 (2H, m), 3.91 (3H, s), 3.50-3.42 (4H, m), 3.00-2.87 (4H, m), 1.74-1.64 (6H, m). |
| 11 (11b) | $^1$H-NMR (400 MHz, CDCl$_3$) δ: 7.94 (2H, d, J = 8.2 Hz), 7.91 (1H, s), 7.48 (2H, d, J = 8.6 Hz), 7.22 (2H, d, J = 8.6 Hz), 7.13 (2H, d, J = 8.6 Hz), 7.10 (1H, d, J = 2.7 Hz), 7.01 (1H, dd, J = 8.6, 2.7 Hz), 6.70 (1H, d, J = 8.6 Hz), 4.94 (2H, br s), 3.90 (3H, s), 3.02-2.90 (8H, m), 1.76-1.71 (4H, m), 1.58-1.52 (2H, m). |
| 11 (11c) | $^1$H-NMR (400 MHz, CDCl$_3$) δ: 11.54 (1H, s), 8.60 (1H, d, J = 9.4 Hz), 8.44 (1H, s), 8.12 (1H, d, J = 8.2 Hz), 7.99 (1H, d, J = 7.8 Hz), 7.95 (2H, d, J = 8.2 Hz), 7.88 (1H, s), 7.61 (1H, t, J = 7.8 Hz), 7.49 (2H, d, J = 8.2 Hz), 7.23 (2H, d, J = 8.2 Hz), 7.19-7.14 (4H, m), 3.91 (3H, s), 3.69-3.64 (1H, m), 3.63 (3H, s), 3.29 (2H, q, J = 7.0 Hz), 3.16 (4H, t, J = 5.5 Hz), 3.00-2.93 (4H, m), 2.18-2.08 (1H, |

TABLE 9-continued

| Ex No. | Physicochemical data |
|---|---|
| | m), 2.02-1.94 (2H, m), 1.78-1.69 (6H, m), 1.64-1.58 (2H, m), 1.50-1.40 (4H, m), 1.25 (3H, t, J = 7.2 Hz). |
| 11 (11d) | $^1$H-NMR (400 MHz, DMSO-D$_6$) δ: 11.38 (1H, s), 10.39 (1H, s), 8.27 (1H, s), 8.15-8.08 (2H, m), 8.04 (1H, d, J = 7.4 Hz), 7.84 (2H, d, J = 8.2 Hz), 7.76 (1H, t, J = 7.8 Hz), 7.59 (2H, d, J = 8.6 Hz), 7.34 (3H, d, J = 8.2 Hz), 7.18 (3H, d, J = 8.2 Hz), 3.66-3.55 (1H, m), 3.25-3.18 (6H, m), 2.98-2.85 (4H, m), 2.12-2.03 (1H, m), 1.84 (2H, br d, J = 12.1 Hz), 1.70-1.62 (4H, m), 1.60-1.52 (2H, m), 1.51-1.41 (4H, m), 1.38-1.25 (2H, m), 1.13 (3H, t, J = 7.0 Hz). MS (ESI) m/z: 781 (M + H)$^+$. |
| 12 | $^1$H-NMR (400 MHz, CD$_3$OD) δ: 8.40 (1H, t, J = 1.8 Hz), 8.33 (1H, d, J = 9.0 Hz), 8.15 (1H, dt, J = 7.8, 1.4 Hz), 8.04 (1H, dq, J = 7.9, 0.9 Hz), 7.84 (2H, d, J = 8.2 Hz), 7.72 (1H, t, J = 7.8 Hz), 7.56 (2H, d, J = 8.2 Hz), 7.42 (1H, d, J = 2.7 Hz), 7.22-7.16 (5H, m), 3.69-3.60 (1H, m), 3.28-3.21 (6H, m), 2.93 (4H, s), 2.00-1.85 (3H, m), 1.80-1.71 (4H, m), 1.67-1.54 (4H, m), 1.53-1.36 (4H, m), 1.22 (3H, t, J = 7.0 Hz). |
| 13 (13a) | $^1$H-NMR (400 MHz, CDCl$_3$) δ: 8.11 (1H, d, J = 10.2 Hz), 7.95 (2H, d, J = 8.2 Hz), 7.51 (2H, d, J = 8.2 Hz), 7.31 (1H, s), 7.23 (2H, d, J = 8.2 Hz), 7.14 (2H, d, J = 8.2 Hz), 6.64-6.60 (2H, m), 3.91 (3H, s), 3.47 (4H, q, J = 7.2 Hz), 3.00-2.90 (4H, m), 1.23 (6H, t, J = 7.0 Hz). |
| 13 (13b) | $^1$H-NMR (400 MHz, CDCl$_3$) δ: 8.32 (1H, br s), 7.95 (2H, d, J = 8.2 Hz), 7.50 (2H, d, J = 8.2 Hz), 7.23 (2H, d, J = 7.8 Hz), 7.13 (2H, d, J = 8.6 Hz), 7.01 (1H, br s), 6.85 (1H, dd, J = 8.6, 2.7 Hz), 6.72 (1H, d, J = 8.6 Hz), 4.63 (2H, br s), 3.91 (3H, s), 3.24 (4H, q, J = 7.0 Hz), 3.00-2.90 (4H, m), 1.10 (6H, t, J = 7.0 Hz). |
| 13 (13c) | $^1$H-NMR (400 MHz, CDCl$_3$) δ: 11.24 (1H, s), 8.47 (1H, d, J = 9.4 Hz), 8.43 (1H, t, J = 1.6 Hz), 8.12-8.08 (1H, m), 7.99-7.92 (4H, m), 7.60 (1H, t, J = 7.8 Hz), 7.51 (2H, d, J = 7.8 Hz), 7.24 (2H, d, J = 8.2 Hz), 7.17 (2H, d, J = 8.6 Hz), 6.88 (1H, dd, J = 9.2, 2.9 Hz), 6.82 (1H, d, J = 2.3 Hz), 3.91 (3H, s), 3.69-3.64 (1H, m), 3.63 (3H, s), 3.36 (4H, q, J = 7.0 Hz), 3.29 (2H, q, J = 7.0 Hz), 3.00-2.92 (4H, m), 2.16-2.10 (1H, m), 2.00-1.95 (2H, m), 1.75-1.70 (2H, m), 1.51-1.40 (4H, m), 1.25 (3H, t, J = 7.0 Hz), 1.17 (6H, t, J = 7.0 Hz). |
| 13 (13d) | $^1$H-NMR (400 MHz, DMSO-D$_6$) δ: 10.99 (1H, s), 10.32 (1H, s), 8.27 (1H, s), 8.10 (1H, d, J = 7.8 Hz), 8.02 (1H, d, J = 8.6 Hz), 7.91 (1H, d, J = 8.6 Hz), 7.84 (2H, d, J = 8.6 Hz), 7.74 (1H, t, J = 7.8 Hz), 7.58 (2H, d, J = 8.6 Hz), 7.34 (2H, d, J = 8.2 Hz), 7.17 (2H, d, J = 8.2 Hz), 6.97 (1H, d, J = 2.7 Hz), 6.89 (1H, dd, J = 9.0, 2.7 Hz), 3.65-3.55 (1H, m), 3.41 (4H, q, J = 6.8 Hz), 3.21 (2H, q, J = 6.9 Hz), 2.96-2.85 (4H, m), 2.12-2.04 (1H, m), 1.84 (2H, br d, J = 12.1 Hz), 1.50-1.41 (4H, m), 1.37-1.25 (2H, m), 1.13 (3H, t, J = 7.0 Hz), 1.13 (6H, t, J = 7.0 Hz). MS (ESI) m/z: 769 (M + H)$^+$. |

TABLE 10

| Ex No. | Physicochemical data |
|---|---|
| 14 | $^1$H-NMR (400 MHz, CD$_3$OD) δ: 8.38 (1H, t, J = 1.6 Hz), 8.15-8.10 (2H, m), 8.03 (1H, d, J = 7.8 Hz), 7.84 (2H, d, J = 8.2 Hz), 7.71 (1H, t, J = 7.8 Hz), 7.53 (2H, d, J = 8.2 Hz), 7.17 (4H, dd, J = 8.0, 1.4 Hz), 7.10 (1H, d, J = 2.7 Hz), 6.93 (1H, dd, J = 9.0, 2.7 Hz), 3.68-3.61 (1H, m), 3.47 (4H, q, J = 6.8 Hz), 3.29-3.26 (2H, m), 2.93 (4H, br s), 2.02-1.89 (3H, m), 1.59-1.38 (6H, m), 1.24-1.17 (9H, m). MS (ESI) m/z: 769 (M + H)$^+$. |
| 15 (15a) | $^1$H-NMR (400 MHz, CDCl$_3$) δ: 8.05-8.01 (1H, m), 7.04-7.00 (2H, m), 3.93 (3H, s), 3.91 (2H, d, J = 7.0 Hz), 1.34-1.25 (1H, m), 0.69-0.68 (2H, m), 0.43-0.32 (2H, m). |
| 15 (15b) | $^1$H-NMR (400 MHz, CDCl$_3$) δ: 8.03 (1H, d, J = 9.4 Hz), 7.16 (1H, d, J = 2.7 Hz), 7.05 (1H, dd, J = 9.0, 2.7 Hz), 3.93 (2H, d, J = 7.0 Hz), 1.35-1.24 (1H, m), 0.74-0.67 (2H, m), 0.43-0.36 (2H, m). |
| 15 (15c) | $^1$H-NMR (400 MHz, CDCl$_3$) δ: 8.17 (1H, d, J = 9.0 Hz), 7.95 (2H, d, J = 8.2 Hz), 7.49 (2H, d, J = 8.6 Hz), 7.33 (1H, s), 7.23 (2H, d, J = 8.2 Hz), 7.15 (2H, d, J = 8.6 Hz), 7.02 (2H, dt, J = 10.7, 3.7 Hz), 3.92 (2H, d, J = 7.0 Hz), 3.91 (3H, s), 3.01-2.90 (4H, m), 1.35-1.25 (1H, m), 0.70 (2H, q, J = 6.3 Hz), 0.38 (2H, q, J = 5.2 Hz). |
| 15 (15d) | $^1$H-NMR (500 MHz, CDCl$_3$) δ: 7.95 (2H, d, J = 8.3 Hz), 7.91 (1H, s), 7.47 (2H, d, J = 8.3 Hz), 7.22 (2H, d, J = 8.3 Hz), 7.13 (2H, d, J = 8.3 Hz), 7.07 (1H, d, J = 2.4 Hz), 6.92 (1H, dd, J = 8.8, 2.9 Hz), 6.70 (1H, d, J = 8.8 Hz), 4.97 (2H, br s), 3.91 (3H, s), 3.77 (2H, d, J = 6.8 Hz), 3.00-2.89 (4H, m), 1.29-1.21 (1H, m), 0.66-0.63 (2H, m), 0.34 (2H, q, J = 5.2 Hz). |
| 15 (15e) | $^1$H-NMR (400 MHz, CDCl$_3$) δ: 11.73 (1H, s), 8.67 (1H, d, J = 9.0 Hz), 8.46 (1H, t, J = 1.8 Hz), 8.14 (1H, dt, J = 7.8, 1.2 Hz), 8.00-7.96 (4H, m), 7.62 (1H, t, J = 7.8 Hz), 7.51 (2H, d, J = 8.2 Hz), 7.26- |

TABLE 10-continued

| Ex No. | Physicochemical data |
| --- | --- |
| | 7.16 (5H, m), 7.09 (1H, dd, J = 9.0, 2.7 Hz), 3.91 (3H, s), 3.83 (2H, d, J = 7.0 Hz), 3.73-3.65 (1H, m), 3.63 (3H, s), 3.30 (2H, q, J = 7.2 Hz), 3.01-2.92 (4H, m), 2.17-2.09 (1H, m), 2.01-1.95 (2H, m), 1.75-1.69 (2H, m), 1.53-1.38 (4H, m), 1.26 (4H, t, J = 7.0 Hz), 0.69-0.65 (2H, m), 0.36 (2H, q, J = 5.1 Hz). |
| 15 (15f) | $^1$H-NMR (CD$_3$OD, 400 MHz) δ: 8.42 (1H, t, J = 1.8 Hz), 8.35 (1H, d, J = 9.0 Hz), 8.18 (1H, d, J = 7.8 Hz), 8.04 (1H, dt, J = 7.8, 1.0 Hz), 7.84 (2H, d, J = 7.8 Hz), 7.72 (1H, t, J = 7.8 Hz), 7.55 (2H, d, J = 8.2 Hz), 7.44 (1H, d, J = 2.7 Hz), 7.19-7.14 (5H, m), 3.92 (2H, d, J = 6.7 Hz), 3.69-3.62 (1H, m), 3.33-3.27 (2H, m), 2.92 (4H, br s), 1.98-1.87 (3H, m), 1.62-1.35 (6H, m), 1.32-1.27 (1H, m), 1.24 (3H, t, J = 6.3 Hz), 0.66-0.61 (2H, m), 0.40-0.36 (2H, m). MS (ESI) m/z: 768 (M + H)$^+$. |
| 16 (16a) | $^1$H NMR (400 MHz, CDCl$_3$): δ (ppm) = 8.54 (1H, s), 8.27 (1H, d, J = 7.6 Hz), 8.07 (1H, d, J = 8.4 Hz), 7.61 (1H, t, J = 8.0 Hz), 7.47-7.37 (5H, m), 5.40 (2H, s), 4.40 (1H, d, J = 8.0 Hz), 3.64 (3H, s), 3.17-3.12 (1H, m), 2.21-2.14 (1H, m), 1.98-1.88 (4H, m), 1.48-1.37 (2H, m), 1.23-1.12 (2H, m). MS (ESI) m/z: 432 (M + H)$^+$. |
| 16 (16b) | $^1$H NMR (400 MHz, CDCl$_3$): δ (ppm) = 8.47 (1H, t, J = 1.6 Hz), 8.25 (1H, dt, J = 7.8 and 1.4 Hz), 8.07 (1H, dt, J = 9.4 and 1.4 Hz), 7.60 (1H, t, J = 7.8 Hz), 7.46-7.34 (5H, m), 5.40 (2H, s), 3.85-3.77 (1H, m), 3.66 (3H, s), 2.75 (3H, s), 2.17-2.09 (1H, m), 2.01-1.97 (2H, m), 1.60-1.34 (6H, m). MS (ESI) m/z: 446 (M + H)$^+$. |
| 16 (16c) | $^1$H NMR (400 MHz, DMSO-d$_6$): δ (ppm) = 13.56 (1H, brs), 8.24 (1H, t, J = 1.6 Hz), 8.20 (1H, dt, J = 7.8 and 1.4 Hz), 8.07 (1H, dt, J = 7.8 and 1.4 Hz), 7.75 (1H, t, J = 7.8 Hz), 3.74-3.65 (1H, m), 3.56 (3H, s), 2.68 (3H, s), 2.22-2.15 (1H, m), 1.89-1.84 (2H, m), 1.51-1.29 (6H, m). |

TABLE 11

| Ex No. | Physicochemical data |
| --- | --- |
| 16 (16d) | $^1$H NMR (400 MHz, CDCl$_3$): δ (ppm) = 11.52 (1H, brs), 8.55-8.52 (1H, m), 8.38 (1H, t, J = 1.6 Hz), 8.10 (2H, d, J = 7.8 Hz), 7.95-7.90 (3H, m), 7.59 (1H, t, J = 7.8 Hz), 7.54-7.47 (3H, m), 7.21-7.09 (5H, m), 3.87 (3H, s), 3.81-3.74 (1H, m), 3.59 (3H, s), 3.11-3.06 (4H, m), 2.98-2.89 (4H, m), 2.78 (3H, s), 2.11-2.03 (1H, m), 1.97-1.90 (2H, m), 1.66-1.27 (12H, m). MS (ESI) m/z: 795 (M + H)$^+$. |
| 16 (16e) | $^1$H NMR (400 MHz, DMSO-d$_6$): δ (ppm) = 11.34 (1H, brs), 10.36 (1H, brs), 8.20 (1H, s), 8.08 (2H, t, J = 7.8 Hz), 7.98 (1H, d, J = 7.8 Hz), 7.77-7.72 (3H, m), 7.55 (2H, d, J = 8.4 Hz), 7.30 (1H, s), 7.23 (2H, d, J = 7.8 Hz), 7.16-7.10 (3H, m), 3.68-3.60 (1H, m), 3.20-3.16 (4H, m), 2.93-2.83 (4H, m), 2.66 (3H, s), 2.07-1.99 (1H, m), 1.82-1.75 (2H, m), 1.65-1.58 (4H, m), 1.55-1.49 (2H, m), 1.40-1.20 (6H, m). MS (ESI) m/z: 767 (M + H)$^+$. |
| 17 (17a) | $^1$H NMR (400 MHz, CDCl$_3$): δ (ppm) = 8.50 (1H, t, J = 1.8 Hz), 8.25 (1H, dt, J = 7.8 and 1.4 Hz), 8.02 (1H, dt, J = 8.2 and 1.4 Hz), 7.59 (1H, t, J = 7.8 Hz), 7.47-7.34 (5H, m), 5.40 (2H, s), 3.65-3.62 (4H, m), 3.54 (2H, t, J = 6.4 Hz), 3.33-3.29 (5H, m), 2.19-2.11 (1H, m), 2.02-1.89 (2H, m), 1.68-1.62 (2H, m), 1.52-1.39 (4H, m). MS (ESI) m/z: 490 (M + H)$^+$. |
| 17 (17b) | $^1$H NMR (400 MHz, CDCl$_3$): δ (ppm) = 8.53 (1H, t, J = 1.6 Hz), 8.26 (1H, dt, J = 7.8 and 1.4 Hz), 8.05 (1H, dt, J = 8.2 and 1.4 Hz), 7.61 (1H, t, J = 7.8 Hz), 3.66-3.58 (5H, m), 3.54 (2H, d, J = 6.6 Hz), 3.33-3.22 (4H, m), 2.13-2.09 (1H, m), 2.00-1.86 (2H, m), 1.66-1.58 (2H, m), 1.52-1.38 (4H, m). MS (ESI) m/z: 400 (M + H)$^+$. |
| 17 (17c) | $^1$H NMR (400 MHz, CDCl$_3$): δ (ppm) = 11.50 (1H, brs), 8.55 (1H, d, J = 9.8 Hz), 8.42 (1H, t, J = 1.6 Hz), 8.10 (2H, d, J = 7.8 Hz), 8.01-7.87 (3H, m), 7.59 (1H, t, J = 7.8 Hz), 7.51-7.45 (3H, m), 7.26-7.11 (5H, m), 3.87 (3H, s), 3.61-3.58 (4H, m), 3.53 (2H, t, J = 6.5 Hz), 3.34-3.26 (5H, m), 3.14-3.10 (4H, m), 2.96-2.88 (4H, m), 2.14-2.05 (1H, m), 1.98-1.89 (2H, m), 1.73-1.36 (12H, m). MS (ESI) m/z: 840 (M + H)$^+$. |
| 17 (17d) | $^1$H NMR (400 MHz, DMSO-d$_6$): δ (ppm) = 11.22 (1H, brs), 10.34 (1H, brs), 8.17 (1H, s), 8.07 (1H, d, J = 7.8 Hz), 8.03-7.99 (2H, m), 7.71 (1H, t, J = 7.8 Hz), 7.65 (2H, d, J = 8.2 Hz), 7.52 (2H, d, J = 8.6 Hz), 7.26 (1H, d, J = 2.7 Hz), 7.13 (1H, dd, J = 9.2 and 2.7 Hz), 7.07-7.01 (4H, m), 3.61-3.50 (1H, m), 3.38 (2H, d, J = 6.6 Hz), 3.21-3.16 (7H, m), 2.88-2.84 (4H, m), 2.16-2.09 (1H, m), 1.81-1.76 (2H, m), 1.64-1.48 (6H, m), 1.33-1.14 (6H, m), 1.00 (2H, d, J = 6.3 Hz). MS (ESI) m/z: 811 (M + H)$^+$. |
| 18 (18a) | $^1$H NMR (400 MHz, CDCl$_3$): δ (ppm) = 8.54 (1H, t, J = 1.8 Hz), 8.23 (1H, dt, J = 7.8 and 1.4 Hz), 8.04 (1H, dt, J = 8.6 and 1.6 Hz), 7.58 (1H, t, J = 7.8 Hz), 7.46-7.36 (5H, m), 5.39 (2H, s), 3.66 (3H, s), 3.63-3.56 (1H, m), 3.11 (2H, d, J = 6.7 Hz), 2.20-2.15 (1H, m), 2.05-1.99 (2H, m), |

TABLE 11-continued

| Ex No. | Physicochemical data |
|---|---|
| | 1.77-1.74 (2H, m), 1.54-1.43 (4H, m), 0.99-0.93 (1H, m), 0.54-0.44 (2H, m), 0.30-0.26 (2H, m). MS (ESI) m/z: 486 (M + H)$^+$. |
| 18 (18b) | $^1$H NMR (400 MHz, CDCl$_3$): δ (ppm) = 11.46 (1H, brs), 8.51 (1H, d, J = 8.9 Hz), 8.43 (1H, t, J = 1.6 Hz), 8.07 (1H, d, J = 7.8 Hz), 8.00-7.90 (3H, m), 7.57 (1H, t, J = 7.8 Hz), 7.48 (2H, d, J = 8.2 Hz), 7.20 (2H, d, J = 6.6 Hz), 7.14-7.07 (5H, m), 3.87 (3H, s), 3.62-3.54 (4H, m), 3.17-3.06 (6H, m), 2.98-2.89 (4H, m), 1.98-1.93 (3H, m), 1.77-1.38 (12H, m), 1.03-0.97 (1H, m), 0.53-0.46 (2H, m), 0.27-0.22 (2H, m). MS (ESI) m/z: 835 (M + H)$^+$. |
| 18 (18c) | $^1$H NMR (400 MHz, DMSO-d$_6$): δ (ppm) = 11.33 (1H, brs), 10.41 (1H, brs), 8.21 (1H, s), 8.07-7.99 (3H, m), 7.74-7.71 (3H, m), 7.53 (2H, d, J = 8.2 Hz), 7.29 (1H, d, J = 2.4 Hz), 7.15-7.07 (5H, m), 3.56-3.46 (1H, m), 3.19-3.15 (4H, m), 3.01 (2H, d, J = 7.8 Hz), 2.89-2.80 (4H, m), 2.11-2.03 (1H, m), 1.80 (2H, d, J = 9.2 Hz), 1.64-1.14 (12H, m), 0.99-0.90 (1H, m), 0.43-0.38 (2H, m), 0.21-0.17 (2H, m). MS (ESI) m/z: 807 (M + H)$^+$. |

TABLE 12

| Ex No. | Physicochemical data |
|---|---|
| 19 (19a) | $^1$H NMR (400 MHz, CDCl$_3$): δ (ppm) = 8.11 (1H, dd, J = 9.0 and 4.7 Hz), 8.07 (1H, brs), 7.93 (2H, d, J = 8.2 Hz), 7.47 (2H, d, J = 8.6 Hz), 7.32-7.11 (6H, m), 3.88 (3H, s), 2.69 (2H, t, J = 7.6 Hz), 2.63 (2H, t, J = 7.6 Hz), 2.00-1.90 (2H, m). |
| 19 (19b) | $^1$H NMR (400 MHz, CDCl$_3$): δ (ppm) = 8.01 (1H, d, J = 9.4 Hz), 7.95 (2H, d, J = 8.6 Hz), 7.66 (1H, brs), 7.51 (2H, d, J = 8.2 Hz), 7.25 (2H, d, J = 8.2 Hz), 7.14 (2H, d, J = 8.2 Hz), 6.80 (1H, d, J = 2.7 Hz), 6.75 (1H, dd, J = 9.4 and 2.7 Hz), 3.89 (3H, s), 3.48-3.38 (4H, m), 2.69 (2H, t, J = 7.8 Hz), 2.62 (2H, t, J = 7.6 Hz), 2.00-1.90 (2H, m), 1.73-1.60 (6H, m). |
| 19 (19c) | $^1$H NMR (400 MHz, CDCl$_3$): δ (ppm) = 8.00-7.90 (3H, m), 7.49 (2H, d, J = 8.6 Hz), 7.28-7.14 (5H, m), 7.03 (1H, dd, J = 8.6 and 2.7 Hz), 6.70 (1H, d, J = 9.0 Hz), 5.32-4.72 (2H, brs), 3.91 (3H, s), 3.09-2.99 (4H, m), 2.70 (2H, t, J = 7.6 Hz), 2.64 (2H, t, J = 7.6 Hz), 2.02-1.91 (2H, m), 1.83-1.71 (4H, m), 1.62-1.51 (2H, m). |
| 19 (19d) | $^1$H NMR (400 MHz, CDCl$_3$): δ (ppm) = 11.5 (1H, s), 8.57 (1H, brs), 8.47-8.40 (2H, m), 8.14-8.08 (1H, m), 8.02-7.94 (3H, m), 7.66-7.57 (3H, m), 7.26 (2H, d, J = 8.6 Hz), 7.21 (2H, d, J = 8.6 Hz), 7.09 (1H, d, J = 2.4 Hz), 7.00 (1H, dd, J = 9.0 and 2.7 Hz), 3.90 (3H, s), 3.73-3.64 (1H, m), 3.62 (3H, s), 3.30 (2H, q, J = 7.0 Hz), 3.04-2.96 (4H, m), 2.72 (2H, t, J = 7.6 Hz), 2.66 (2H, t, J = 7.6 Hz), 2.18-2.07 (1H, m), 2.04-1.91 (4H, m), 1.82-1.66 (2H, m), 1.62-1.36 (10H, m), 1.26 (3H, t, J = 7.0 Hz). |
| 19 (19e) | $^1$H NMR (400 MHz, CD$_3$OD): δ (ppm) = 8.38 (1H, s), 8.32 (1H, d, J = 9.0 Hz), 8.16 (1H, d, J = 7.8 Hz), 8.04 (1H, d, J = 7.8 Hz), 7.88 (2H, d, J = 8.2 Hz), 7.71 (1H, t, J = 7.8 Hz), 7.58 (2H, d, J = 8.2 Hz), 7.42 (1H, d, J = 2.7 Hz), 7.25-7.16 (5H, m), 3.70-3.57 (1H, m), 3.30-3.21 (6H, m), 2.68 (2H, t, J = 7.4 Hz), 2.64 (2H, t, J = 7.4 Hz), 2.05-1.85 (5H, m), 1.80-1.70 (4H, m), 1.68-1.30 (8H, m), 1.20 (3H, t, J = 7.0 Hz). MS (ESI) m/z: 795 (M + H)$^+$. |
| 20 (20a) | $^1$H NMR (400 MHz, CDCl$_3$): δ (ppm) = 8.39 (1H, brs), 8.05 (1H, dd, J = 9.0 and 4.7 Hz), 7.88 (2H, d, J = 8.2 Hz), 7.43 (1H, s), 7.34 (1H, d, J = 7.0 Hz), 7.25-7.12 (5H, m), 6.94 (1H, d, J = 7.8 Hz), 3.85 (3H, s), 2.98-2.82 (4H, m). |
| 20 (20b) | $^1$H NMR (400 MHz, CDCl$_3$): δ (ppm) = 8.09 (1H, d, J = 9.4 Hz), 7.95 (2H, d, J = 8.2 Hz), 7.54 (1H, s), 7.45 (1H, s), 7.38 (1H, d, J = 8.2 Hz), 7.30-7.20 (3H, m), 6.94 (1H, d, J = 7.4 Hz), 6.85-6.77 (2H, m), 3.90 (3H, s), 3.51-3.40 (4H, m), 3.06-2.90 (4H, m), 1.83-1.56 (6H, m). |
| 20 (20c) | $^1$H NMR (400 MHz, CDCl$_3$): δ (ppm) = 7.98 (1H, brs), 7.96 (2H, d, J = 8.2 Hz), 7.51 (1H, s), 7.37 (1H, d, J = 8.2 Hz), 7.29-7.22 (3H, m), 7.13 (1H, d, J = 2.7 Hz), 7.02 (1H, dd, J = 8.6 and 2.7 Hz), 6.93 (1H, d, J = 7.8 Hz), 6.71 (1H, J = 8.6 Hz), 5.10-4.80 (2H, brs), 3.90 (3H, s), 3.08-2.91 (8H, m), 1.78-1.70 (4H, m), 1.60-1.51 (2H, m). |
| 20 (20d) | $^1$H NMR (400 MHz, CDCl$_3$): δ (ppm) = 11.5 (1H, s), 8.51 (1H, d, J = 9.0 Hz), 8.46 (1H, s), 8.19 (1H, s), 8.12 (1H, d, J = 8.2 Hz), 7.99 (1H, d, J = 8.2 Hz), 7.95 (2H, d, J = 8.6 Hz), 7.62 (1H, t, J = 7.8 Hz), 7.54-7.47 (2H, m), 7.34-7.24 (3H, m), 7.13 (1H, d, J = 2.7 Hz), 7.08 (1H, dd, J = 9.0 and 2.7 Hz), 6.99 (1H, d, J = 7.4 Hz), 3.89 (3H, s), 3.73-3.61 (4H, m), 3.28 (2H, q, J = 7.0 Hz), 3.14-3.07 (4H, m), 3.06-2.95 (4H, m), 2.18-2.07 (1H, m), 2.02-1.92 (2H, m), 1.78-1.36 (12H, m), 1.26 (3H, t, J = 7.0 Hz). |
| 20 (20e) | $^1$H NMR (400 MHz, DMSO-d$_6$): δ (ppm) = 11.8 (1H, brs), 10.9 (1H, brs), 8.30 (1H, s), 8.17 (1H, d, J = 7.8 Hz), 7.97 (1H, d, J = 7.4 Hz), 7.91 (1H, d, J = 7.8 Hz), 7.76 (2H, d, J = 8.2 Hz), 7.72-7.62 (2H, m), 7.55 (1H, s), 7.33 (1H, s), 7.23-7.05 (4H, m), 6.93 (1H, d, J = 7.8 Hz), 3.59-3.47 (1H, m), 3.25-3.16 (4H, m), 3.10 (2H, q, J = 7.0 Hz), 2.87- |

TABLE 12-continued

| Ex No. | Physicochemical data |
|---|---|
| | 2.75 (4H, m), 1.98-1.86 (m, 1H), 1.83-1.70 (m, 2H), 1.69-1.50 (6H, m), 1.42-1.14 (6H, m), 1.03 (3H, t, J = 7.0 Hz). MS (ESI) m/z: 781 (M + H)$^+$. |

TABLE 13

| Ex No. | Physicochemical data |
|---|---|
| 21 (21a) | $^1$H NMR (400 MHz, CDCl$_3$): δ (ppm) = 8.59 (1H, brs), 8.32 (1H, d, J = 2.0 Hz), 8.23 (1H, dd, J = 9.0 and 4.7 Hz), 8.18-8.10 (1H, m), 8.04 (1H, dd, J = 8.6 and 2.3 Hz), 7.39-7.29 (2H, m). |
| 21 (21b) | $^1$H NMR (400 MHz, CDCl$_3$): δ (ppm) = 9.47 (1H, brs), 8.20 (1H, d, J = 8.6 Hz), 8.05 (1H, d, J = 8.6 Hz), 7.98 (1H, dd, J = 9.0 and 2.4 Hz), 7.89 (1H, d, J = 2.4 Hz), 6.85 (1H, dd, J = 9.4 and 2.7 Hz), 6.80 (1H, d, J = 2.7 Hz), 3.49-3.40 (4H, m), 1.73-1.62 (6H, m). |
| 21 (21c) | $^1$H NMR (400 MHz, CDCl$_3$): δ (ppm) = 8.88 (1H, brs), 8.38 (1H, d, J = 8.6 Hz), 8.17 (1H, dd, J = 2.4 and 0.8 Hz), 8.09 (1H, d, J = 9.8 Hz), 8.05 (2H, d, J = 8.6 Hz), 7.89 (1H, dd, J = 8.6 and 2.4 Hz), 7.60 (2H, d, J = 8.6 Hz), 6.84-6.80 (2H, m), 3.95 (3H, s), 3.50-3.40 (4H, m), 1.77-1.60 (6H, m). |
| 21 (21d) | $^1$H NMR (400 MHz, CDCl$_3$): δ (ppm) = 8.57 (1H, brs), 8.23 (1H, d, J = 8.2 Hz), 8.04 (1H, d, J = 2.4 Hz), 7.96 (2H, d, J = 8.2 Hz), 7.50 (1H, dd, J = 8.6 and 2.4 Hz), 7.21 (2H, d, J = 8.6 Hz), 7.11 (1H, d, J = 2.7 Hz), 7.04 (1H, dd, J = 9.0 and 2.7 Hz), 6.70 (1H, d, J = 8.6 Hz), 5.20-5.05 (2H, brs), 3.91 (3H, s), 3.02-2.90 (8H, m), 1.77-1.68 (4H, m), 1.58-1.50 (2H, m). |
| 21 (21e) | $^1$H NMR (400 MHz, CDCl$_3$): δ (ppm) = 11.7 (1H, brs), 9.02 (1H, brs), 8.64 (1H, d, J = 9.4 Hz), 8.48 (1H, t, J = 1.6 Hz), 8.27 (1H, d, J = 8.6 Hz), 8.17 (1H, dt, J = 8.2 and 1.6 Hz), 8.04-7.93 (4H, m), 7.64 (1H, t, J = 7.8 Hz), 7.55 (1H, d, J = 8.6 and 2.6 Hz), 7.24-7.13 (4H, m), 3.90 (3H, s), 3.77-3.64 (1H, m), 3.63 (3H, s), 3.31 (2H, q, J = 7.0 Hz), 3.19-3.10 (4H, m), 3.03-2.87 (4H, m), 2.22-1.93 (3H, m), 1.81-1.31 (12H, m), 1.26 (3H, t, J = 7.0 Hz). |
| 21 (21f) | $^1$H NMR (400 MHz, CD$_3$OD): δ (ppm) = 8.42 (1H, t, J = 2.0 Hz), 8.27 (1H, d, J = 9.0 Hz), 8.17 (1H, dt, J = 6.7 and 1.2 Hz), 8.13 (1H, d, J = 8.6 Hz), 8.10 (1H, d, J = 2.4 Hz), 8.06 (1H, ddd, J = 7.8, 2.0 and 1.2 Hz), 7.85 (2H, dt, J = 8.2 and 2.0 Hz), 7.77-7.69 (2H, m), 7.45 (1H, d, J = 2.7 Hz), 7.23 (1H, dd, J = 9.0 and 2.7 Hz), 7.17 (2H, dt, J = 8.2 and 2.0 Hz), 3.74-3.63 (1H, m), 3.35-3.28 (2H, m), 3.28-3.23 (4H, m), 2.98-2.94 (4H, m), 2.04-1.87 (3H, m), 1.81-1.71 (4H, m), 1.68-1.35 (8H, m), 1.24 (3H, t, J = 7.0 Hz). MS (ESI) m/z: 782 (M + H)$^+$. |
| 22 (22a) | $^1$H NMR (400 MHz, CDCl$_3$): δ (ppm) = 8.38 (1H, s), 8.27-8.09 (3H, m), 7.51 (1H, d, J = 8.6 Hz), 7.40-7.28 (2H, m). |
| 22 (22b) | $^1$H NMR (400 MHz, CDCl$_3$): δ (ppm) = 8.36 (1H, s), 8.17 (1H, d, J = 8.6 Hz), 8.07 (1H, d, J = 9.0 Hz), 7.62 (1H, brs), 7.48 (1H, d, J = 8.2 Hz), 6.85-6.74 (2H, m), 3.56-3.41 (4H, m), 1.78-1.63 (6H, m). |
| 22 (22c) | $^1$H NMR (400 MHz, CDCl$_3$): δ (ppm) = 8.58 (1H, s), 8.54 (1H, d, J = 2.3 Hz), 8.34 (1H, dd, J = 8.6 and 2.3 Hz), 8.00 (2H, d, J = 6.7 Hz), 7.97 (1H, d, J = 9.4 Hz), 7.59 (2H, d, J = 6.7 Hz), 7.51 (1H, d, J = 8.6 Hz), 6.77 (1H, d, J = 2.7 Hz), 6.74 (1H, dd, J = 9.4 and 2.7 Hz), 3.92 (3H, s), 3.45-3.40 (4H, m), 1.70-1.62 (6H, m). |
| 22 (22d) | $^1$H NMR (400 MHz, CDCl$_3$): δ (ppm) = 8.77 (1H, s), 8.70 (1H, d, J = 2.3 Hz), 8.07 (1H, dd, J = 8.4 and 2.4 Hz), 7.93 (2H, d, J = 8.2 Hz), 7.55 (1H, s), 7.24 (2H, d, J = 7.8 Hz), 7.10 (1H, dd, J = 8.8 and 2.5 Hz), 7.04 (1H, d, J = 8.2 Hz), 6.68 (1H, d, J = 8.6 Hz), 3.90 (3H, s), 3.16-3.10 (4H, m), 3.11-3.07 (4H, m), 1.90-1.82 (4H, m), 1.62-1.55 (2H, m). |
| 22 (22e) | $^1$H NMR (400 MHz, CDCl$_3$): δ (ppm) = 11.39 (1H, s), 8.69 (1H, d, J = 2.3 Hz), 8.47 (1H, d, J = 9.4 Hz), 8.41 (1H, t, J = 1.6 Hz), 8.22 (1H, s), 8.09-8.03 (2H, m), 7.97 (1H, d, J = 7.8 Hz), 7.91 (2H, dt, J = 8.2, 1.8 Hz), 7.59 (1H, t, J = 7.8 Hz), 7.23 (2H, d, J = 8.2 Hz), 7.12-7.01 (3H, m), 3.86 (3H, s), 3.67-3.61 (1H, m), 3.59 (3H, s), 3.25 (2H, q, J = 7 Hz), 3.11-3.09 (4H, m), 3.08-3.01 (4H, m), 2.15-2.16 (1H, m), 1.98-1.90 (2H, m), 1.72-1.66 (2H, m), 1.66-1.58 (4H, m), 1.52-1.35 (6H, m), 1.22 (3H, t, J = 7 Hz). |

TABLE 14

| Ex No. | Physicochemical data |
|---|---|
| 22 (22f) | $^1$H NMR (400 MHz, DMSO-d$_6$): δ (ppm) = 8.55-8.48 (1H, m), 8.37 (1H, s), 8.26-8.20 (2H, m), 7.91-7.84 (2H, m), 7.73 (2H, d, J = 7.8 Hz), 7.69-7.58 (2H, m), 7.07 (2H, d, J = 7.8 Hz), 7.04-6.98 (2H, m), 3.53 (1H, m), 3.15 (2H, q, J = 6.7 Hz), 3.11-3.04 (4H, m), 2.95-2.90 (4H, m), 2.02 (1H, m), 1.79-1.76 (2H, m), 1.69-1.62 (4H, m), 1.56-1.51 (2H, m), 1.39-1.34 (4H, m), 1.21-1.15 (2H, m), 1.12 (3H, t, J = 7.0 Hz). MS (ESI) m/z: 782 (M + H)$^+$. |

TABLE 14-continued

| Ex No. | Physicochemical data |
| --- | --- |
| 23 (23a) | ¹H NMR (400 MHz, CDCl₃): δ (ppm) = 7.38-7.30 (5H, m), 5.11 (2H, s), 2.67 (2H, q, J = 7.2 Hz), 2.45 (1H, tt, J = 11.0 and 3.7 Hz), 2.31 (1H, tt, J = 12.1 and 3.5 Hz), 2.06-1.96 (4H, m), 1.55-1.44 (4H, m), 1.10 (4H, t, J = 7.2 Hz). |
| 23 (23b) | ¹H NMR (400 MHz, CDCl₃): δ (ppm) = 9.34 (1H, s), 9.18 (1H, s), 8.67 (1H, s), 7.38-7.31 (5H, m), 5.10 (2H, s), 4.00 (3H, s), 3.72-3.64 (1H, m), 3.27 (2H, q, J = 7.0 Hz), 2.23 (1H, m), 2.08-2.05 (2H, m), 1.73-1.71 (2H, m), 1.56-1.47 (4H, m), 1.26 (3H, t, J = 7.0 Hz). |
| 23 (23c) | ¹H NMR (400 MHz, CDCl₃): δ (ppm) = 9.35 (1H, d, J = 2.0 Hz), 9.18 (1H, d, J = 2.3 Hz), 8.67 (1H, t, J = 2.2 Hz), 4.01 (3H, s), 3.69-3.65 (1H, m), 3.27 (2H, q, J = 7.0 Hz), 2.07-2.03 (1H, m), 2.02-1.96 (2H, m), 1.74-1.67 (2H, m), 1.54-1.43 (4H, m), 1.42 (9H, s), 1.26 (3H, t, J = 7.0 Hz). |
| 23 (23d) | ¹H NMR (400 MHz, CDCl₃): δ (ppm) = 11.77 (1H, s), 9.32 (1H, d, J = 2.0 Hz), 9.16 (1H, d, J = 2.0 Hz), 8.64 (1H, t, J = 2.0 Hz), 8.56 (1H, s), 8.41 (1H, d, J = 9.0 Hz), 7.95 (2H, d, J = 7.8 Hz), 7.62 (2H, d, J = 8.2 Hz), 7.25 (2H, d, J = 8.2 Hz), 7.19 (2H, d, J = 8.2 Hz), 7.09 (1H, d, J = 2.7 Hz), 6.98 (1H, dd, J = 9.4 and 2.7 Hz), 3.90 (3H, s), 3.72-3.67 (1H, m), 3.30 (2H, q, J = 7.0 Hz), 3.05-3.01 (4H, m), 3.00-2.93 (4H, m), 2.07-2.03 (1H, m), 2.01-1.94 (2H, m), 1.78-1.71 (2H, m), 1.62-1.55 (4H, m), 1.54-1.43 (4H, m), 1.40 (9H, s), 1.26 (3H, t, J = 7.0 Hz). |
| 23 (23e) | ¹H NMR (400 MHz, DMSO-d₆): δ (ppm) = 9.26 (1H, s), 9.09 (1H, s), 8.52 (1H, s), 7.96 (1H, s), 7.68 (2H, d, J = 7.8 Hz), 7.52-7.34 (3H, m), 7.13-7.00 (6H, m), 3.67-3.58 (1H, m), 3.38 (2H, q, J = 7.0 Hz), 3.20-3.11 (4H, m), 2.90-2.82 (4H, m), 2.06-1.94 (1H, m), 1.84-1.76 (2H, m), 1.69-1.61 (4H, m), 1.58-1.51 (2H, m), 1.43-1.21 (6H, m), 1.10 (4H, t, J = 7.0 Hz). MS (ESI) m/z: 782 (M + H)⁺. |
| 24 (24a) | ¹H NMR (400 MHz, CDCl₃): δ (ppm) = 8.19 (1H, d, J = 9.0 Hz), 7.95 (2H, d, J = 8.4 Hz), 7.51 (2H, d, J = 8.6 Hz), 7.34 (1H, brs), 7.22 (2H, d, J = 8.4 Hz), 7.15 (2H, d, J = 8.6 Hz), 7.06-7.02 (2H, m), 3.94 (3H, s), 3.91 (3H, s), 2.99-2.92 (4H, m). |
| 24 (24c) | ¹H NMR (400 MHz, CDCl₃): δ (ppm) = 11.67 (1H, s), 8.65 (1H, d, J = 9.0 Hz), 8.46 (1H, brs), 8.13 (1H, d, J = 8.6 Hz), 8.04-8.00 (2H, m), 7.95 (2H, d, J = 8.2 Hz), 7.63 (1H, t, J = 7.8 Hz), 7.53 (2H, d, J = 8.6 Hz), 7.23 (2H, d, J = 8.6 Hz), 7.18 (2H, d, J = 8.2 Hz), 7.15 (1H, d, J = 2.7 Hz), 7.09 (1H, dd, J = 2.7 and 9.0 Hz), 3.91 (3H, s), 3.81 (3H, s), 3.63 (3H, s), 3.70-3.59 (1H, m), 3.30 (2H, q, J = 7.0 Hz), 3.00-2.93 (4H, m), 2.18-2.10 (1H, m), 1.99-1.96 (2H, m), 1.74-1.71 (2H, m), 1.52-1.43 (4H, m), 1.26 (3H, t, J = 7.0 Hz). |
| 24 (24d) | ¹H NMR (400 MHz, DMSO-d₆): δ (ppm) = 8.26 (1H, brs), 8.12-8.09 (3H, m), 7.96-7.88 (1H, m), 7.65 (2H, d, J = 8.2 Hz), 7.50-7.39 (3H, m), 7.05-6.69 (5H, m), 3.78 (3H, s), 3.57-3.49 (1H, m), 3.58-3.07 (2H, m), 2.81 (4H, brs), 1.76-1.70 (3H, m), 1.33-1.14 (6H, m), 1.07 (3H, t, J = 6.8 Hz). MS (ESI) m/z: 728 (M + H)⁺. |
| 25 (25a) | ¹H NMR (400 MHz, CDCl₃): δ (ppm) = 7.94 (2H, d, J = 8.2 Hz), 7.85 (1H, brs), 7.47 (2H, d, J = 8.2 Hz), 7.22 (2H, d, J = 8.2 Hz), 7.11-7.15 (3H, m), 6.95 (1H, dd, J = 3.0 and 8.8 Hz), 6.72 (1H, d, J = 8.8 Hz), 5.11 (2H, brs), 4.30 (2H, q, J = 8.2 Hz), 3.90 (3H, s), 2.99-2.91 (4H, m). |

TABLE 15

| Ex No. | Physicochemical data |
| --- | --- |
| 25 (25b) | ¹H NMR (400 MHz, CDCl₃): δ (ppm) = 11.79 (1H, s), 8.75 (2H, d, J = 9.0 Hz), 8.46-8.45 (1H, m), 8.15-8.12 (1H, m), 8.02-7.94 (3H, m), 7.65-7.49 (3H, m), 7.31-7.25 (1H, m), 7.22 (2H, d, J = 8.6 Hz), 7.18 (2H, d, J = 8.6 Hz), 7.15-7.12 (1H, m), 4.41 (2H, q, J = 7.8 Hz), 3.91 (3H, s), 3.68-3.63 (1H, m), 3.63 (3H, s), 3, 29 (2H, q, J = 7.0 Hz), 3.00-2.93 (1H, m), 2.19-2.08 (1H, m), 1.99-1.96 (2H, m), 1.73-1.70 (2H, m), 1.49-1.42 (4H, m), 1.26 (3H, t, J = 7.0 Hz). |
| 25 (25c) | ¹H NMR (400 MHz, DMSO-d₆): δ (ppm) = 8.32 (1H, brs), 8.22-8.14 (3H, m), 7.69-7.62 (4H, m), 7.63 (1H, s), 7.56-7.42 (2H, m), 7.07-7.01 (5H, m), 4.84-4.75 (2H, m), 3.60-3.52 (1H, m), 3.16-3.09 (2H, m), 2.85-2.83 (4H, m), 1.99-1.76 (3H, m), 1.42-1.19 (6H, m), 1.12-1.09 (3H, m). MS (ESI) m/z: 796 (M + H)⁺. |
| 26 (26a) | ¹H-NMR (CDCl₃, 400 MHz) δ: 8.54 (1H, t, J = 1.6 Hz), 8.26 (1H, dt, J = 7.7, 1.3 Hz), 8.06 (1H, dt, J = 8.2, 1.5 Hz), 7.60 (1H, t, J = 7.8 Hz), 7.47-7.35 (5H, m), 5.40 (2H, s), 4.57 (1H, d, J = 7.4 Hz), 3.66 (3H, s), 3.41-3.33 (1H, m), 2.44-2.38 (1H, m), 1.87-1.78 (2H, m), 1.65-1.45 (6H, m). |
| 26 (26b) | ¹H-NMR (CDCl₃, 400 MHz) δ: 8.49 (1H, t, J = 1.6 Hz), 8.23 (1H, dt, J = 7.8, 1.4 Hz), 8.01 (1H, dt, J = 8.1, 1.5 Hz), 7.57 (1H, t, J = 7.8 Hz), 7.46-7.34 (5H, m), 5.39 (2H, s), 3.73-3.63 (1H, m), 3.73 (3H, s), 3.21 (2H, q, J = 7.2 Hz), 2.58 (1H, br s), 2.14 (2H, br d, J = 11.7 Hz), 1.63-1.37 (6H, m), 1.21 (3H, t, J = 7.0 Hz). |
| 26 (26c) | ¹H-NMR (CD₃OD, 400 MHz) δ: 8.42 (1H, t, J = 1.8 Hz), 8.24 (1H, dt, J = 7.7, 1.3 Hz), 8.05 (1H, dq, J = 7.8, 1.0 Hz), 7.68 (1H, t, J = |

TABLE 15-continued

| Ex No. | Physicochemical data |
|---|---|
| | 7.8 Hz), 3.68-3.64 (1H, m), 3.66 (3H, s), 3.23 (2H, q, J = 7.2 Hz), 2.63-2.59 (1H, m), 2.17-2.10 (2H, m), 1.67-1.51 (4H, m), 1.46-1.41 (2H, m), 1.21 (3H, t, J = 7.0 Hz). |
| 26 (26d) | $^1$H-NMR (CDCl$_3$, 400 MHz) δ: 11.55 (1H, s), 8.56 (1H, d, J = 9.0 Hz), 8.45 (1H, t, J = 1.8 Hz), 8.12 (1H, d, J = 7.8 Hz), 8.05 (1H, br s), 7.99 (1H, dq, J = 7.8, 0.9 Hz), 7.95 (2H, d, J = 8.2 Hz), 7.61 (1H, t, J = 7.8 Hz), 7.53 (2H, d, J = 8.6 Hz), 7.23 (2H, d, J = 8.6 Hz), 7.17 (2H, d, J = 8.2 Hz), 7.16-7.10 (2H, m), 3.91 (3H, s), 3.77-3.68 (1H, m), 3.66 (3H, s), 3.25 (2H, q, J = 7.0 Hz), 3.13 (4H, t, J = 5.3 Hz), 2.99-2.94 (4H, m), 2.52 (1H, br s), 2.11 (2H, br d, J = 10.9 Hz), 1.71-1.69 (4H, m), 1.58-1.47 (8H, m), 1.23 (3H, t, J = 7.0 Hz). |
| 26 (26e) | $^1$H-NMR (CD$_3$OD, 500 MHz) δ: 8.43 (1H, s), 8.36 (1H, d, J = 8.8 Hz), 8.16 (1H, d, J = 7.8 Hz), 8.03 (1H, d, J = 7.8 Hz), 7.84 (2H, d, J = 8.3 Hz), 7.72 (1H, t, J = 7.8 Hz), 7.58 (2H, d, J = 8.3 Hz), 7.43 (1H, d, J = 2.9 Hz), 7.23-7.15 (5H, m), 3.74-3.67 (1H, m), 3.27-3.23 (6H, m), 2.97-2.90 (4H, m), 2.27 (1H, br s), 2.12 (2H, br d, J = 14.2 Hz), 1.79-1.60 (8H, m), 1.42-1.27 (4H, m), 1.24 (3H, t, J = 6.8 Hz). MS (ESI) m/z: 781 (M + H)$^+$. |
| 27 (27a) | (cis-isomer + trans-isomer) <br> $^1$H NMR (400 MHz, CDCl$_3$): δ (ppm) = 8.50-8.49 (1H, m), 8.25-8.21 (1H, m), 8.03-8.00 (1H, m), 7.59-7.55 (1H, m), 7.43-7.32 (5H, m), 5.36 (1.6H, s), 5.26 (0.4H, s), 4.10-4.05 (2H, m), 3.88-3.76 (1H, m), 2.54-1.42 (10H, m), 1.23-1.19 (3H, m), 0.93-0.88 (2H, m), 0.72-0.65 (2H, m). MS (ESI) m/z: 486 (M + H)$^+$. |
| 27 (27b) | (cis-isomer + trans-isomer) <br> $^1$H NMR (400 MHz, CDCl$_3$): δ (ppm) = 11.52-11.51 (1H, m), 8.58-8.54 (1H, m), 8.45-8.43 (1H, m), 8.14-8.12 (2H, m), 7.99-7.83 (4H, m), 7.62-7.58 (1H, m), 7.45-7.43 (2H, m), 7.20-7.12 (5H, m), 4.11-4.02 (2H, m), 3.88-3.87 (3H, m), 3.14-3.11 (4H, m), 2.96-2.89 (4H, m), 2.48-1.43 (16H, m), 1.24-1.22 (1H, m), 1.21-1.16 (3H, m), 0.95-0.91 (2H, m), 0.73-0.69 (2H, m). MS (ESI) m/z: 835 (M + H)$^+$. |

TABLE 16

| Ex No. | Physicochemical data |
|---|---|
| 27 (27c) | $^1$H NMR (400 MHz, CDCl$_3$): δ (ppm) = 11.30 (1H, brs), 10.42 (1H, brs), 8.21-7.98 (4H, m), 7.79-7.63 (3H, m), 7.68 (1H, d, J = 7.8 Hz), 7.65 (1H, d, J = 7.8 Hz), 7.28 (1H, dd, J = 6.6 and 2.5 Hz), 7.15 (1H, dd, J = 6.6 and 2.5 Hz), 7.08-7.01 (4H, m), 3.65-3.60 (1H, m), 3.20-3.13 (4H, m), 2.93-2.87 (4H, m), 2.20-2.13 (1H, m), 1.99-1.76 (4H, m), 1.65-1.48 (6H, m), 1.43-1.15 (5H, m), 0.81-0.74 (2H, m), 0.67-0.60 (2H, m). MS (ESI) m/z: 793 (M + H)$^+$. |

TABLE 17

| Ex No. | Physicochemical data |
|---|---|
| 28 | $^1$H-NMR (CD$_3$OD) δ: 8.40 (1H, t, J = 1.6 Hz), 8.33 (1H, d, J = 9.0 Hz), 8.15 (1H, dt, J = 7.8, 1.4 Hz), 8.05 (1H, dt, J = 8.0, 1.4 Hz), 7.84 (2H, d, J = 8.6 Hz), 7.73 (1H, t, J = 8.0 Hz), 7.56 (2H, d, J = 8.6 Hz), 7.42 (1H, d, J = 2.7 Hz), 7.22-7.16 (5H, m), 3.69-3.60 (1H, m), 3.26-3.23 (6H, m), 2.93 (4H, s), 2.01-1.86 (3H, m), 1.79-1.73 (4H, m), 1.65-1.56 (4H, m), 1.52-1.36 (4H, m), 1.22 (3H, t, J = 6.5 Hz). |
| 29 | $^1$H-NMR (CD$_3$OD) δ: 8.38 (1H, t, J = 1.8 Hz), 8.14-8.11 (2H, m), 8.04 (1H, dt, J = 7.8, 1.4 Hz), 7.84 (2H, d, J = 8.6 Hz), 7.71 (1H, t, J = 7.8 Hz), 7.53 (2H, d, J = 8.2 Hz), 7.17 (4H, d, J = 7.8 Hz), 7.09 (1H, d, J = 2.3 Hz), 6.93 (1H, dd, J = 9.0, 2.7 Hz), 3.68-3.62 (1H, m), 3.47 (4H, q, J = 6.9 Hz), 3.28-3.26 (2H, m), 2.92 (4H, br s), 2.01-1.89 (3H, m), 1.59-1.36 (6H, m), 1.24-1.18 (9H, m). |
| 30 | $^1$H-NMR (CD$_3$OD, 400 MHz) δ: 8.41 (1H, t, J = 1.6 Hz), 8.38 (1H, d, J = 9.0 Hz), 8.17 (1H, d, J = 7.8 Hz), 8.05 (1H, dt, J = 8.0, 1.4 Hz), 7.84 (2H, d, J = 8.2 Hz), 7.73 (1H, t, J = 7.8 Hz), 7.56 (2H, d, J = 8.2 Hz), 7.43 (1H, d, J = 2.7 Hz), 7.20- |

TABLE 17-continued

| Ex No. | Physicochemical data |
|---|---|
| | 7.14 (5H, m), 3.93 (2H, d, J = 7.0 Hz), 3.68-3.63 (1H, m), 3.33-3.28 (2H, m), 2.93 (4H, br s), 1.97-1.87 (3H, m), 1.61-1.36 (6H, m), 1.31-1.27 (1H, m), 1.22 (3H, t, J = 7.0 Hz), 0.66-0.61 (2H, m), 0.40-0.36 (2H, m). |
| 31 | $^1$H-NMR (CD$_3$OD, 400 MHz) δ: 8.42 (1H, s), 8.36 (1H, d, J = 9.0 Hz), 8.16 (1H, d, J = 7.8 Hz), 8.03 (1H, d, J = 7.8 Hz), 7.84 (2H, d, J = 7.8 Hz), 7.72 (1H, t, J = 7.8 Hz), 7.58 (2H, d, J = 8.6 Hz), 7.43 (1H, d, J = 2.7 Hz), 7.23-7.16 (5H, m), 3.75-3.66 (1H, m), 3.28-3.22 (6H, m), 2.97-2.88 (4H, m), 2.27 (1H, br s), 2.12 (2H, br d, J = 13.3 Hz), 1.79-1.60 (8H, m), 1.43-1.29 (4H, m), 1.21 (3H, t, J = 7.0 Hz). |
| 32 | $^1$H-NMR (CD$_3$OD) δ: 8.39-8.38 (1H, m), 8.35 (1H, dd, J = 13.5, 9.2 Hz), 8.20 (1H, t, J = 6.1 Hz), 8.08-8.06 (1H, m), 7.85 (2H, d, J = 7.8 Hz), 7.76 (1H, t, J = 7.8 Hz), 7.55-7.53 (2H, m), 7.42 (1H, t, J = 3.5 Hz), 7.21-7.18 (5H, m), 3.85-3.76 (1H, m), 3.24 (4H, t, J = 5.1 Hz), 2.28-1.52 (16H, m), 1.44-1.29 (4H, m), 0.94-0.90 (2H, m), 0.78-0.71 (2H, m). |

The invention claimed is:

1. A compound of the following formula:

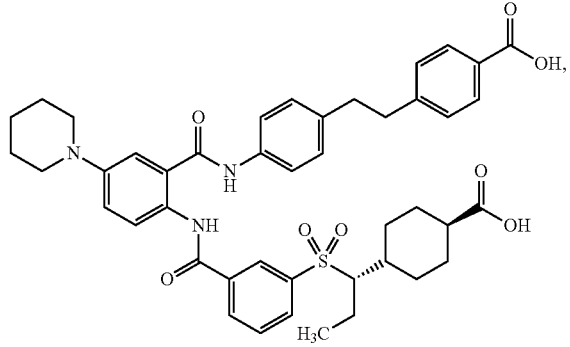

or a pharmacologically acceptable salt thereof, or a hydrate of the compound or pharmacologically acceptable salt thereof.

2. The compound of claim 1 wherein the pharmacologically acceptable salt is a disodium salt.

3. The compound of claim 1 wherein the hydrate of the compound is the trihydrate.

4. A compound of the following formula:

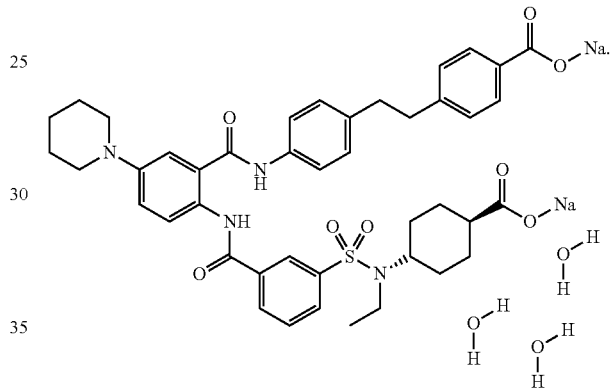

5. A method for the prevention or treatment of hyperphosphatemia comprising administering to a patient a compound according to claim 4.

6. A pharmaceutical composition comprising the compound according to claim 4.

7. The pharmaceutical composition according to claim 6, wherein administration of an effective amount of the pharmaceutical composition to a patient inhibits the uptake of phosphorus in the patient.

8. A method for the prevention or treatment of hyperphosphatemia comprising administering to a patient a compound or pharmacologically acceptable salt thereof, or the hydrate of the compound or pharmacologically acceptable salt thereof, according to claim 1.

9. A pharmaceutical composition comprising the compound or pharmacologically acceptable salt thereof, or the hydrate of the compound or pharmacologically acceptable salt thereof, according to claim 1.

10. The pharmaceutical composition according to claim 9, wherein administration of an effective amount of the pharmaceutical composition to a patient inhibits the uptake of phosphorus in the patient.

* * * * *

UNITED STATES PATENT AND TRADEMARK OFFICE
CERTIFICATE OF CORRECTION

PATENT NO.       : 9,670,173 B2
APPLICATION NO.  : 15/282384
DATED            : June 6, 2017
INVENTOR(S)      : Yoshikazu Uto et al.

Page 1 of 1

It is certified that error appears in the above-identified patent and that said Letters Patent is hereby corrected as shown below:

In the Claims

Column 85, Line 30:
Claim 1 please replace the formula:

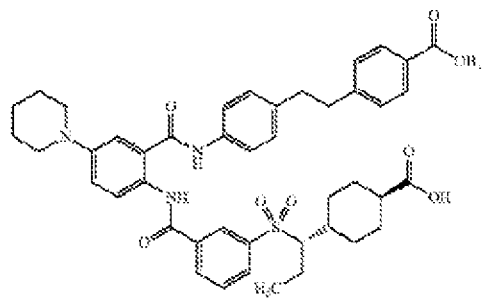

With the correct formula as shown below:

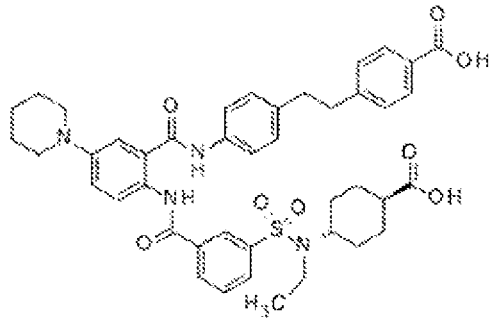

Signed and Sealed this
Twelfth Day of September, 2017

Joseph Matal
*Performing the Functions and Duties of the
Under Secretary of Commerce for Intellectual Property and
Director of the United States Patent and Trademark Office*